(12) United States Patent
Chao et al.

(10) Patent No.: US 7,326,729 B2
(45) Date of Patent: Feb. 5, 2008

(54) CXCR1 AND CXCR2 CHEMOKINE ANTAGONISTS

(75) Inventors: Jianhua Chao, Pompton Lakes, NJ (US); Arthur G. Taveras, Southborough, MA (US); Cynthia J. Aki, Livingston, NJ (US)

(73) Assignee: Schering Corporation, Kenilworth, NJ (US)

( * ) Notice: Subject to any disclaimer, the term of this patent is extended or adjusted under 35 U.S.C. 154(b) by 1 day.

(21) Appl. No.: 11/126,977

(22) Filed: May 11, 2005

(65) Prior Publication Data

US 2006/0014794 A1  Jan. 19, 2006

Related U.S. Application Data

(60) Provisional application No. 60/570,326, filed on May 12, 2004.

(51) Int. Cl.
 *A61K 31/4025* (2006.01)
 *A61K 31/381* (2006.01)
 *C07D 409/12* (2006.01)
 *C07D 207/34* (2006.01)
 *C07D 333/36* (2006.01)

(52) U.S. Cl. .................... 514/422; 514/426; 514/444; 514/447; 548/527; 548/557; 549/59; 549/69

(58) Field of Classification Search ............... 549/63, 549/59, 69; 514/422, 426, 444, 447; 548/527, 548/557
See application file for complete search history.

(56) References Cited

U.S. PATENT DOCUMENTS

| 5,780,483 | A | 7/1998 | Widdowson et al. |
|---|---|---|---|
| 6,525,069 | B1 | 2/2003 | Ko et al. |
| 6,649,636 | B1 | 11/2003 | Ando et al. |
| 6,878,709 | B2 | 4/2005 | Taveras et al. |
| 6,903,131 | B2 | 6/2005 | Taveras et al. |
| 7,132,445 | B2 | 11/2006 | Taveras et al. |

FOREIGN PATENT DOCUMENTS

| EP | 0 255 297 | 2/1988 |
|---|---|---|
| EP | 0202538 B1 * | 12/1988 |
| EP | 1 270 551 | 1/2003 |
| WO | WO96/25157 | 8/1996 |
| WO | WO97/29743 | 8/1997 |
| WO | WO97/49286 | 12/1997 |
| WO | WO97/49287 | 12/1997 |
| WO | WO97/49399 | 12/1997 |
| WO | WO97/49400 | 12/1997 |
| WO | WO97/49680 | 12/1997 |
| WO | WO98/05317 | 2/1998 |
| WO | WO98/05328 | 2/1998 |
| WO | WO98/05329 | 2/1998 |
| WO | WO98/06262 | 2/1998 |
| WO | WO98/06397 | 2/1998 |
| WO | WO98/06398 | 2/1998 |
| WO | WO98/06399 | 2/1998 |
| WO | WO98/07418 | 2/1998 |
| WO | WO98/32438 | 7/1998 |
| WO | WO98/32439 | 7/1998 |
| WO | WO99/11253 | 3/1999 |
| WO | WO 99/11264 | 3/1999 |
| WO | WO99/11264 | 3/1999 |
| WO | WO99/36070 | 7/1999 |
| WO | WO 00/76517 | 12/2000 |
| WO | WO 01/64165 | 9/2001 |
| WO | WO 01/64691 | 9/2001 |
| WO | WO 01/68084 | 9/2001 |
| WO | WO 01/72960 | 10/2001 |
| WO | WO 01/98270 | 12/2001 |
| WO | WO 02/076926 | 10/2002 |
| WO | WO 03/031440 | 4/2003 |
| WO | WO 03/057676 | 7/2003 |
| WO | WO 03/080053 | 10/2003 |
| WO | WO 04/033440 | 4/2004 |
| WO | WO 05/066147 | 7/2005 |
| WO | WO 05/068460 | 7/2005 |
| WO | WO 07/002764 | 1/2007 |

OTHER PUBLICATIONS

Co-pending U.S. Appl. No. 11/651,128, filed Jan. 09, 2007.
Co-pending U.S. Appl. No. 10/390,078, filed Mar. 17, 2003.
Co-pending U.S. Appl. No. 11/013,753, filed Dec. 16, 2004.
Co-pending U.S. Appl. No. 11/017,505, filed Dec. 20, 2003.
Co-pending U.S. Appl. No. 11/475,789, filed Jun. 27, 2006.
Co-pending U.S. Appl. No. 11/500,739, filed Aug. 08, 2006.
Co-pending U.S. Appl. No. 11/475,811, filed Jun. 27, 2006.
PCT International Search Report for PCT counterpart Application No. PCT/US2005/016507 of the above identified application.

* cited by examiner

*Primary Examiner*—Joseph K. McKane
*Assistant Examiner*—Joseph R. Kosack
(74) *Attorney, Agent, or Firm*—Henry C. Jeanette

(57) ABSTRACT

The present invention is directed to a compound having the general structure of formula (1):

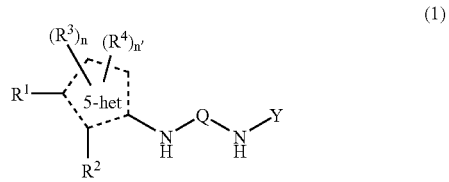

(1)

useful for the treatment, prevention or amelioration of a CXCR1 or CXCR2 chemokine-mediated disease.

13 Claims, No Drawings

CXCR1 AND CXCR2 CHEMOKINE ANTAGONISTS

REFERENCE TO RELATED APPLICATION

This application claims the benefit of U.S. Provisional Application Ser. No. 60/570326 filed May 12, 2004, the disclosure of which is incorporated herein by reference thereto.

FIELD OF THE INVENTION

The present invention relates to novel CXCR1 and CXCR2 chemokine antagonists, pharmaceutical compositions containing the compounds and methods of treatment using the compounds, compositions and formulations to treat CXCR1 and/or CXCR2 chemokine-mediated diseases such as acute and chronic inflammatory disorders, psoriasis, stroke, multiple sclerosis and cancer.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include, but are not limited to, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include, but are not limited to, RANTES, MIP-1α, MIP-2β, monocyte chemotactic protein-1 (MCP-1), MCP-2, MCP-3, CCL19, CCL21 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Lett. 307, 97 (1992); Miller et al., Crit. Rev. Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines including IL-8, GROα, GROβ, GROγ, NAP-2, and ENA-78 (Strieter et al. 1995 JBC 270 p. 27348-57) have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possible CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin Cancer Res 6 p. 2104-2119) and poor prognosis (Yoneda et. al. 1998 J Nat Cancer Inst 90 p. 447-454). Chemokines are potent chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J Clin Invest 97 p. 2792-2802), ENA-78 (Arenberg et al. 1998 J Clin Invest 102 p.465-72), and GROα (Haghnegahdar et al. J. Leukoc Biology 2000 67 p. 53-62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

SUMMARY OF THE INVENTION

In its many embodiments, the invention provides a novel class of CXC chemokine-mediators, pharmaceutical compositions comprising one or more of such compounds, and methods of treatment, prevention, inhibition, or amelioration of one or more diseases associated with CXC chemokine mediation using the compounds and compositions claimed herein.

This invention provides novel compounds of the formula (1):

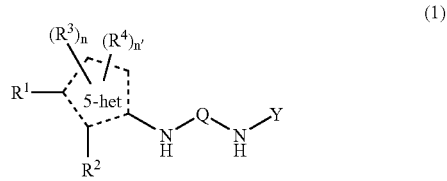

and the pharmaceutically acceptable salts, (e.g., sodium or calcium) and solvates thereof, wherein $R^1$, $R^2$, $R^3$, $R^4$, Q, Y, 5-het, n and n' are defined below.

Compounds of formula (1) have CXCR1 and/or CXCR2 activity.

This invention also provides a pharmaceutical composition comprising at least one compound (e.g., one) of the formula (1) or a pharmaceutically acceptable salt or solvate thereof and a pharmaceutically acceptable carrier.

This invention also provides a method of treating a CXCR1 and/or CXCR2 chemokine mediated disease in a patient in need of such a treatment comprising administering to said patient an effective amount of at least one compound (e.g., one) of the formula (1) or a pharmaceutically acceptable salt or solvate thereof.

This invention also provides a method of treating a CXCR1 and/or CXCR2 chemokine mediated disease in a patient in need of such treatment comprising administering to said patient an effective amount of at least one compound (e.g. one) of formula (1) or a pharmaceutically acceptable salt or solvate thereof, and administering an effective amount of at least one (e.g., one) additional agent, drug, medicament, antibody and/or inhibitor for treating a chemokine mediated disease or drug or agent useful for the treatment of CXCR1 and/or CXCR2 chemokine mediated diseases.

This invention also provides a method wherein the compounds bind to a CXCR1 receptor (e.g., a method of treating a chemokine mediated disease comprising administering an effective amount of at least one (e.g., one) compound of formula 1 wherein said compound binds to a CXCR1 receptor).

This invention also provides a method wherein the compounds bind to a CXCR2 receptor (e.g., a method of treating a chemokine mediated disease comprising administering an effective amount of at least one (e.g., one) compound of formula 1 wherein said compound binds to a CXCR2 receptor).

This invention also provides a method of treating a chemokine mediated disease or condition in a patient in need of such treatment comprising administering: (a) a therapeutically effective amount of at least one compound of formula (1), or a pharmaceutically acceptable salt or solvate thereof, concurrently or sequentially with (b) at least one medicament selected from the group consisting of: disease modifying antirheumatic drugs; nonsteroidal anitinflammatory drugs; COX-2 selective inhibitors; COX-1 inhibitors; immunosuppressives; steroids; biological response modifiers; and other anti-inflammatory agents or therapeutics useful for the treatment of chemokine mediated diseases.

This invention also provides a method comprising treating an inflammatory disease in a patient in need of such treatment.

This invention also provides a method of treating cancer in a patient in need of such treatment which method comprises administering to said patient a therapeutically effective amount of a compound of formula (1) or a pharmaceutically acceptable salt or solvate thereof.

This invention also provides a method of treating cancer in a patient in need of such treatment which method comprises administering to said patient a therapeutically effective amount of at least one compound of formula (1) or a pharmaceutically acceptable salt or solvate thereof.

This invention also provides a method of treating cancer in a patient in need of such treatment which method comprises administering to said patient a therapeutic amount of at least one compound of formula (1), or a pharmaceutically acceptable salt or solvate thereof concurrently or sequentially with (a) at least one antineoplastic agent selected from the group consisting of: (1) gemcitabine, (2) paclitaxel (Taxol®), (3) 5-Fluorouracil (5-FU), (4) cyclo-phosphamide (Cytoxan®), (5) temozolomide and (6) Vincristine.

This invention also provides a method of treating cancer in a patient in need of such treatment which method comprises at least one compound of formula (1), or a pharmaceutically acceptable salt or solvate thereof and at least one agent selected from the group consisting of microtubule affecting agents, antineoplastic agents, anti-angiogenesis agents, VEGF receptor kinase inhibitors, antibodies against the VEGF receptor, interferon, and radiation.

This invention also provides a method of inhibiting angiogenesis in a patient in need of such inhibition said method comprising administering to said patient an effective amount of at least one compound of formula (1).

This invention also provides a method of treating an angiogenic ocular disease in a patient in need of such treatment said method comprising administering to said patient an effective amount of at least one compound of formula (1) or a pharmaceutically acceptable salt or solvate thereof.

This invention also provides a method of treating asthma in a patient in need of such treatment said method comprising administering to the patient a therapeutically effective amount of at least one compound of formula (1) or a pharmaceutically acceptable salt or solvate thereof.

This invention also provides a method of treating a pulmonary disease in a patient in need of such treatment said method comprising administering to said patient a therapeutically effective amount of: (a) at least one compound of formula (1), or a pharmaceutically acceptable salt or solvate thereof concurrently or sequentially with (b) at least one compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones.

This invention also provides a method of treating multiple sclerosis in a patient in need of such treatment said method comprising administering to said patient a therapeutically effective amount of: (a) a therapeutically effective amount of at least one compound of formula (1), or a pharmaceutically acceptable salt or solvate thereof concurrently or sequentially with (b) at least one compound selected from the group consisting of: glatiramer acetate, glucocorticoids, methotrexate, azothioprine, mitoxantrone, and CB2-selective inhibitors.

This invention also provides a method of treating multiple sclerosis in a patient in need of such treatment the method comprising administering to said patient a therapeutically effective amount of: a) at least one compound of formula (1), or a pharmaceutically acceptable salt or solvate thereof concurrently or sequentially with (b) at least one compound selected from the group consisting of: methotrexate, cyclosporin, leflunimide, sulfasalazine, β-methasone, β-interferon, glatiramer acetate, prednisone, etonercept, and infliximab.

This invention also provides a method of treating rheumatoid arthritis in a patient in need of such treatment comprising administering to said patient a therapeutically effective amount of at least one (usually one) compound of formula 1, or a pharmaceutically acceptable salt or solvate thereof.

This invention also provides a method of treating rheumatoid arthritis in a patient in need of such treatment comprising administering to said patient a therapeutically effective amount of at least one (usually 1) compound of formula 1, or a pharmaceutically acceptable salt or solvate thereof, in combination with at least one compound selected from the group consisting of COX-1 inhibitors, COX-2 inhibitors, immunosuppressives (e.g., methotrexate, cyclosporin, leflunimide and sulfasalazine), steroids (e.g., betamethasone, cortisone and dexamethasone), PDE 4 inhibitors, anti-TNF-α compounds, MMP inhibitors, glucocorticoids, chemokine inhibitors, CB2-selective agents, and other classes of compounds indicated for the treatment of rheumatoid arthritis.

This invention also provides a method of treating stroke and ischemia reperfusion injury in a patient in need of such treatment said method comprising administering to said patient a therapeutically effective amount of: (a) at least one compound of formula (1), or a pharmaceutically acceptable salt or solvate thereof concurrently or sequentially with (b) at least one compound selected from the group consisting of: thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of rheumatoid arthritis.

This invention also provides a method of treating stroke and ischemia 10 reperfusion injury in a patient in need of such treatment said method comprising administering to said patient a therapeutically effective amount of: (a) at least one compound of formula (1), or a pharmaceutically acceptable salt or solvate thereof concurrently or sequentially with (b) at least one compound selected from the group consisting of: tenecteplase, TPA, alteplase, abciximab, eftiifbatide, and heparin.

This invention also provides a method of treating psoriasis in a patient in need of such treatment said method comprising administering to said patient a therapeutically effective amount of: a) at least one compound of formula (1), or a pharmaceutically acceptable salt or solvate thereof concurrently or sequentially with (b) at least one compound selected from the group consisting of: immunosuppressives (e.g., methotrexate, cyclosporin, efalizumab, alefacept, leflunimide and sulfasalazine), steroids (e.g., β-methasone) and anti-TNF-α compounds (e.g., etonercept and infliximab).

This invention also provides a method of treating a CXCR1 and/or a CXCR2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one compound (usually 1) of formula 1, or a pharmaceutically acceptable salt or solvate thereof.

This invention also provides a method of treating diseases such as allograft rejections, early transplantation rejections, autoimmune deafness, myocarditis, neuropathies, autoimmune diseases and vasculitis syndromes wherein said (a) Allograft rejections are selected from the group consisting of acute allograft rejections and chronic allograft rejections, (b) Early transplantation rejection is an acute allograft rejection, (c) Autoimmune deafness is Meniere's disease, (d) Myocarditis is viral myocarditis, (e) Neuropathies are selected from the group consisting of IgA neuropathy, membranous neuropathy and idiopathic neuropathy, (f) Autoimmune diseases are anemias, and (g) Vasculitis syndromes are selected from the group consisting of giant cell arteritis, Behcet's disease and Wegener's granulomatosis.

Prodrugs of the compounds of formula (1) or pharmaceutically acceptable salts or solvates thereof are within the scope of the claimed invention.

This invention also provides a method of treating COPD in a patient in need of such treatment comprising administering to said patient a therapeutically effective amount of at least one (usually one) compound of formula 1, or a pharmaceutically acceptable salt or solvate thereof.

This invention also provides a method of treating arthritis in a patient in need of such treatment comprising administering to said patient a therapeutically effective amount of at least one (usually one) compound of formula 1, or a pharmaceutically acceptable salt or solvate thereof.

This invention also provides a method of treating osteoarthritis in a patient in need of such treatment comprising administering to said patient a therapeutically effective amount of at least one (usually one) compound of formula 1, or a pharmaceutically acceptable salt or solvate thereof.

This invention also provides a method of treating pain in a patient in need of such treatment comprising administering to said patient a therapeutically effective amount of at least one (usually one) compound of formula 1, or a pharmaceutically acceptable salt or solvate thereof.

This invention also provides a method of treating pain in a patient in need of such treatment comprising administering to said patient a therapeutically effective amount of at least one (usually one) compound of formula 1, or a pharmaceutically acceptable salt or solvate thereof, and administering a therapeutically effective amount of at least one medicament selected from the group consisting of: NSAIDs, COXIB inhibitors (e.g., COX-1 and COX-2 inhibitors), anti-depressants, and anti-convulsants.

This invention also provides a method of treating acute pain in a patient in need of such treatment comprising administering to said patient a therapeutically effective amount of at least one (usually one) compound of formula 1, or a pharmaceutically acceptable salt or solvate thereof.

This invention also provides a method of treating acute inflammatory pain in a patient in need of such treatment comprising administering to said patient a therapeutically effective amount of at least one (usually one) compound of formula 1, or a pharmaceutically acceptable salt or solvate thereof.

This invention also provides a method of treating chronic inflammatory pain in a patient in need of such treatment comprising administering to said patient a therapeutically effective amount of at least one (usually one) compound of formula 1, or a pharmaceutically acceptable salt or solvate thereof.

This invention also provides a method of treating neropathic pain in a patient in need of such treatment comprising administering to said patient a therapeutically effective amount of at least one (usually one) compound of formula 1, or a pharmaceutically acceptable salt or solvate thereof.

This invention also provides a pharmaceutical composition comprising at least one (e.g., 1-3, usually 1) compound of formula 1, or a pharmaceutically acceptable salt or solvate thereof, and a pharmaceutically acceptable carrier.

This invention also provides a pharmaceutical composition comprising at least one (e.g., 1-3, usually 1) compound of formula 1, or a pharmaceutically acceptable salt or solvate thereof, and at least one (e.g., 1-3, usually 1) other agent, medicament, antibody and/or inhibitor disclosed above, and a pharmaceutically acceptable carrier.

DETAILED DESCRIPTION OF THE INVENTION

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term"alkoxy".

"An effective amount" or a "therapeutically effective amount" means to describe an amount of compound of the present invention or another agent effective to treat a mammal (e.g., human) having a disease or CXC chemokine mediated condition, and thus producing the desired therapeutic effect.

"At least one" means one or more (e.g., 1-3,1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formula (1) with other medicaments in the methods of treatment of this invention, means-that the compounds of formula (1) and the other medicaments are administered sequentially or concurrently in separate dosage forms, or are administered concurrently in the same dosage form.

"Mammal" means a human and other mammals, or means a human being.

"Patient" includes both human and other mammals, preferably human.

"Bn" means benzyl.

"DCC" means dicyclohexylcarbodiimide.

"Et" means ethyl.

"Me" means methyl.

"Ph" means phenyl.

"Prodrug" denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems*, Volume 14 of the A.C.S. Symposium Series, and in *Bioreversible Carriers in Drug Design*, Edward B. Roche, ed., American Pharmaceutical Association and Pergamon Press, 1987, both of which are incorporated herein by reference thereto.

"Alkyl" means an aliphatic hydrocarbon group that may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl, or propyl, are attached to a linear alkyl chain. "Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, heptyl, nonyl, and decyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously desribed. Preferred alkoxyalkyl comprise a lower alkyl group. The bond to the parent moiety is through the alkyl.

"Aryl" (sometimes abbreviated "ar") means an aromatic monocyclic or multicyclic ring system, wherein at least one ring is aromatic, comprising about 6 to about 14 carbon atoms, preferably about 6 to about 10 carbon atoms. Non-limiting examples of suitable aryl groups include: phenyl, naphthyl, indenyl, tetrahydronaphthyl, indanyl, anthracenyl, and fluorenyl.

"Arylalkyl" means an aryl-alkyl-group in which the aryl and alkyl are as previously desribed. Preferred arylalkyls comprise a lower alkyl group. Non-limiting examples of suitable aralkyl groups include benzyl, 2-phenethyl and napthalenylmethyl. The bond to the parent moiety is through the alkyl.

"Alkylaryl" means an alkyl-aryl-group in which the alkyl and aryl are as previously desribed. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aminosulfonyl" means $NH_2S(O)$—, $NH_2S(O)_2$—, $(H)(R^{11})NS(O)$—, $(H)(R^{11})NS(O)_2$—, $(R^{11})(R^{12})NS(O)$—, or $(R^{11})(R^{12})NS(O)_2$—.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a cytokine involved in chemotaxis.

"Chemokine-mediated disease" means a disease of which at least one element or cause is related to the regulation of a CXC chemokine.

"Cycloalkyl" means a non-aromatic mono-or multicyclic ring system comprising about 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the present invention effective in inhibiting the binding by CXC chemokine receptor of CXC chemokine and thus producing the desired therapeutic effect in a suitable patient.

"Fluoroalkoxy" means an alkoxy group as defined above wherein one or more hydrogen atoms on the alkoxy is replaced by a fluoro group.

"Fluoroalkyl" means an alkyl group as defined above wherein one or more hydrogen atoms on the alkyl is replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

"Heteroaralkyl" or "heteroarylalkyl" means a heteroaryl-alkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties or radicals which can be the same or different, with each, for example, being independently selected.

The moiety labeled as "5-het" in formula (1) represents the ring with the indicated substituents, i.e., the moiety "5-het" is

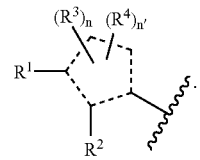

Examples of disease-modifying antirheumatic drugs include, for example, methotrexate, sulfasalzine, leflunomide, TNFα directed agents (e.g., infliximab, etanercept, and adalimumab), IL-1 directed agents (e.g., anakinra) B cell directed agents (e.g., rituximab), T cell directed agents (e.g., alefacept, efalizumab, and CTLA4-lg), TNFα-converting enzyme inhibitors, interleukin-1 converting enzyme is inhibitors, and p38 kinase inhibitors.

The term "other classes of compounds indicated for the treatment of rheumatoid arthritis", as used herein, unless indicated otherwise, means: compounds selected from the group consisting of: IL-1 directed agents (e.g., anakinra); B cell directed agents (e.g., rituximab); T cell directed agents (e.g., alefacept, efalizumab, and CTLA4-lg), TNFα-converting enzyme inhibitors, interleukin-1 converting enzyme inhibitors, and p38 kinase inhibitors.

As well known in the art, a bond drawn from a particular atom wherein no moiety is depicted at the terminal end of the bond indicates a methyl group bound through that bond to the atom. For example:

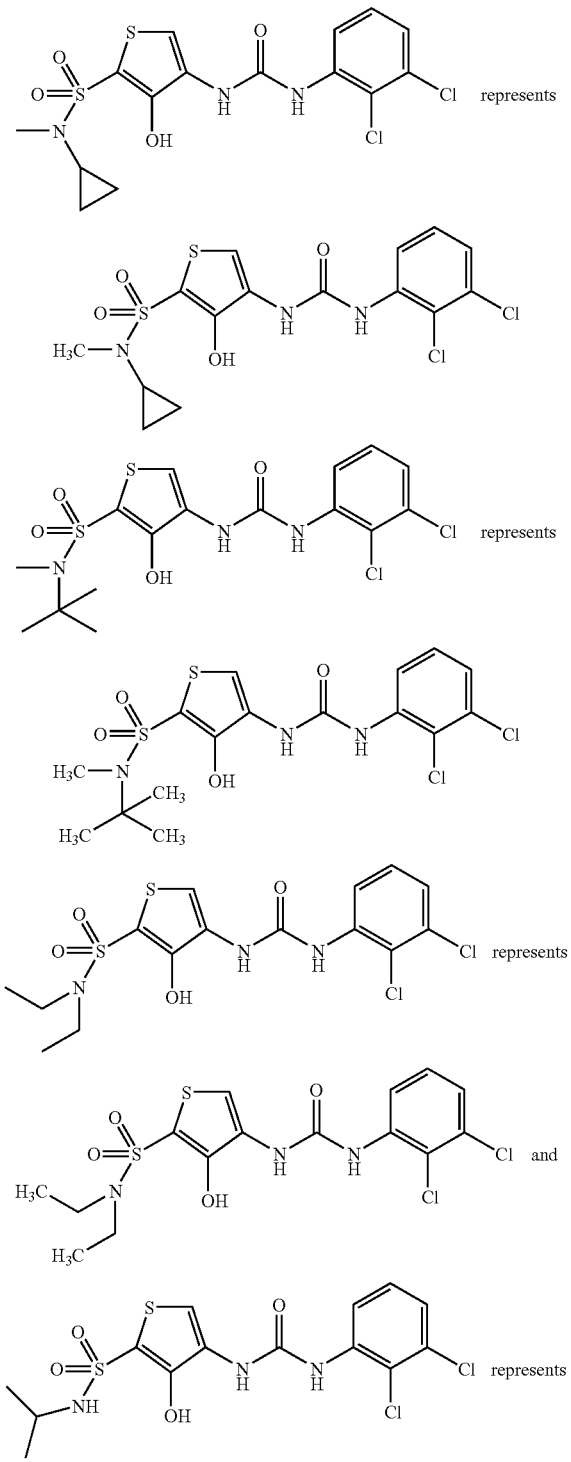

It should also be noted that throughout the specification and Claims appended here to any formula, compound, moiety or chemical illustration with unsatisfied valences is assumed to have the hydrogen atom to satisfy the valences unless the context indicates a bond.

The compounds of formula (1) form salts that are also within the scope of this invention. Reference to a compound of formula (1) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (1) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula (1) may be formed, for example, by reacting a compound of formula (1) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acid which are generally considered suitable for the formation of pharmaceutically useful salts from basic pharmaceutical compounds are discussed, for example, by S. Berge et al, *Journal of Pharmaceutical Sciences* (1977) 66(1)1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), araalkyl halides (e.g., benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula (1) can exist in unsolvated and solvated forms, including hydrated forms. In general, the solvated forms, with pharmaceutically acceptable solvents such as water, ethanol and the like, are equivalent to the unsolvated forms for the purposes of this invention.

Compounds of formula (1) and salts, solvates and prodrugs thereof, may exist in their tautomeric form (for example, as an amide or imino ether). All such tautomeric forms are contemplated herein as part of the present invention.

Also within the scope of the present invention are polymorphs of the compounds of this invention (i.e., polymorphs of the compounds of formula 1 are within the scope of this invention).

Prodrugs of the compounds of formula (1) or pharmaceutically acceptable salts or solvates thereof are within the scope of the claimed invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below), Mithramycin, Deoxyco-formycin, Mitomycin-C, L-Asparaginase, Interferons (especially IFN-a), Etoposide, and Teniposide.

Hormones and steroids (including synthetic analogs): 17β-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2003 edition (Thomson P D R, Montvale, N.J. 07645-1742, USA); the disclosure of which is incorporated herein by reference thereto.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skilled in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science*, 274:2009) estramustine, nocodazole, MAP4, and the like. Examples of such agents are also described in the scientific and patent literature, see, e.g., Bulinski (1997) *J. Cell Sci.* 110:3055-3064; Panda (1997) *Proc. Natl. Acad. Sci. USA* 94:10560-10564; Muhlradt (1997) Cancer Res. 57,3344-3346; Nicolaou (1997) *Nature* 387:268-272; Vasquez (1997) *Mol. Biol. Cell.* 8:973-985; Panda (1996) *J. Biol. Chem.* 271:29807-29812.

Particularly, agents can be compounds with paclitaxel-like activity. These include, but are not limited to paclitaxel (e.g., TAXOL® NSC number 125973) and paclitaxel derivatives (paclitaxel-like compounds) and analogues. Paclitaxel and its derivatives are available commercially. In addition, methods of making paclitaxel and paclitaxel derivatives and analogues are well known to those of skilled in the art (see, e.g., U.S. Pat. Nos. 5,569,729; 5,565,478; 5,530,020; 5,527, 924; 5,508,447; 5,489,589; 5,488,116; 5,484,809; 5,478, 854; 5,478,736; 5,475,120; 5,468,769; 5,461,169; 5,440, 057; 5,422,364; 5,411,984; 5,405,972; and 5,296,506).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41:37-47).

This invention provides novel compounds of the formula (1):

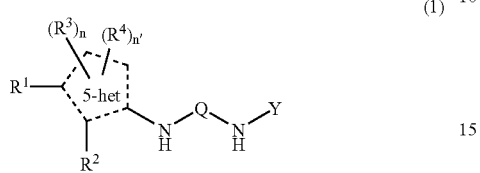

and the pharmaceutically acceptable salts (e.g., sodium or calcium salt) and solvates thereof, wherein:

Y is selected from the group consisting of: unsubstituted phenyl, substituted phenyl, unsubstituted pyridinyl, substituted pyridinyl, unsubstituted pyrazinyl, substituted pyrazinyl, unsubstituted pyrimidinyl substituted pyrimidinyl, unsubstituted thiophene-yl, substituted thiophene-yl, unsubstituted thiazolyl, substituted thiazolyl, unsubstituted furanyl, substituted furanyl, unsubstituted isoxazolyl, substituted isoxazolyl, unsubstituted oxazolyl, substituted oxazolyl, unsubstituted naphthyl, substituted naphthyl, unsubstituted indolyl, substituted indolyl, unsubstituted benzoimidazolyl, substituted benzoimidazolyl, unsubstituted benzodioxolyl, substituted benzodioxolyl, unsubstituted quinolinyl, substituted quinolinyl, unsubstituted benzofuranyl, substituted benzofuranyl, substituted benzothiophene-yl, unsubstituted benzothiophene-yl, unsubstituted pyrrolyl, substituted pyrrolyl, unsubstituted isothiazolyl, substituted isothiazolyl, unsubstituted pyrazolyl, substituted pyrazolyl, unsubstituted pyridazinyl, substituted pyridazinyl, unsubstituted isoquinolinyl, substituted isoquinolinyl, unsubstituted pyridopyrazinyl, substituted pyridopyrazinyl, unsubstituted napthyridinyl, substituted napthyridinyl, unsubstituted triazolyl (e.g. 1,2,4-triazolyl), substituted triazolyl (e.g. substituted 1,2,4-triazolyl), unsubstituted tetrazolyl, substituted tetrazolyl, unsubstituted triazinyl, substituted triazinyl, unsubstituted chromenyl, substituted chromenyl, unsubstituted pteridinyl, substituted pteridinyl, unsubstituted purinyl, and substituted purinyl; said substituted Y groups being substituted with 1 to 5 substituents independently selected from the group consisting of: —OH, halogen, cyano, —CF$_3$, —OCF$_3$, —NR$^{11}$R$^{12}$, —NR$^{11}$—(CO)NR$^{11}$R$^{12}$, —C(O) NR$^{11}$R$^{12}$, —CO$_2$R$^{11}$, —OR$^{11}$, —SO$_{(t)}$NR$^{11}$R$^{12}$, —NR$^{11}$ SO$_{(t)}$R$^{12}$, —COR$^{11}$, substituted aryl, unsubstituted aryl, substituted alkyl, unsubstituted alkyl, substituted alkoxy, unsubstituted alkoxy, substituted arylalkyl, unsubstituted arylalkyl, substituted heteroaryl, unsubstituted heteroaryl, substituted aryloxy, unsubstituted aryloxy, substituted heteroarylalkyl, unsubstituted heteroarylalkyl, substituted heteroarylalkoxy, unsubstituted heteroarylalkoxy, substituted heterocycloalkyl, unsubstituted heterocycloalkyl, substituted hydroxyalkyl, unsubstituted hydroxyalkyl; wherein the substituted substituent groups bound to Y are substituted with 1 to 6 (e.g., 1, or 1-2, or 1-3, or 1-4, or 1-5, or 1-6) substituents independently selected from the group consisting of halogen, —CF$_3$, —COR$^{11}$, —OR$^{11}$, —NR$^{11}$R$^{12}$, —NO$_2$, —CN, —SO$_2$R$^{11}$, —SO$_2$NR$^{11}$R$^{12}$, —NR$^{11}$C(O) R$^{12}$, —C(O)NR$^{11}$R$^{12}$, —NR$^{11}$CO$_2$R$^{12}$ and —CO$_2$R$^{11}$;

Q is selected from the group consisting of:

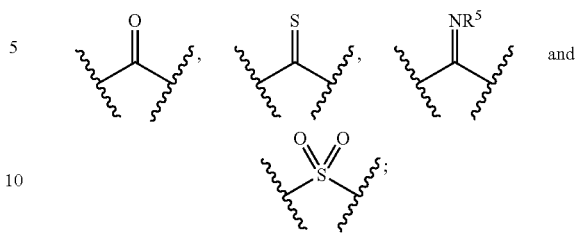

the ring (represented by the dashed lines) of the 5-het moiety is a heteroaryl ring selected from the group consisting of: thiophene-yl, isothiazolyl, pyrrolyl and pyrazolyl;

R$^1$ is bonded to a carbon atom of said 5-het and R$^1$ is selected from the group consisting of: hydrogen, halogen, unsubstituted alkyl, substituted alkyl, unsubstituted alkoxy, substituted alkoxy, —OH, —OCF$_3$, —CF$_3$, —CN, —NO$_2$, —C(O)R$^{11}$, —C(O)OR$^{11}$, —C(O)NR$^{11}$R$^{12}$, —SO$_{(t)}$NR$^{11}$R$^{12}$, —SO$_{(t)}$R$^{11}$, —C(O)NR$^{11}$OR$^{12}$, unsubstituted aryl, substituted aryl, unsubstituted heteroaryl, and substituted heteroaryl;

R$^2$ is bound to a carbon atom of said 5-het and R$^2$ is selected from the group consisting of: —OH, —OC(O)NH R$^{16}$, —NHC(O)R$^{16}$ and —NHS(O)$_2$R$^{16}$;

n=0 or 1;

n'=0 or 1;

R$^3$, when n is 1, is bonded to a carbon atom in said 5-het, and R$^3$ is selected from the group consisting of: halogen, cyano, —CF$_3$, substituted alkyl, unsubstituted alkyl, substituted aryl, unsubstituted aryl, substituted heteroaryl and unsubstituted heteroaryl;

R$^4$, when n' is 1, is bonded to a nitrogen atom in said 5-het and R$^4$ is selected from the group consisting of: substituted alkyl, unsubstituted alkyl, substituted aryl, unsubstituted aryl, substituted heteroaryl, unsubstituted heteroaryl, —COOR$^{17}$ and —OR$^{17}$;

R$^5$ is selected from the group consisting of: hydrogen, cyano, substituted alkyl, unsubstituted alkyl, substituted alkoxy, unsubstituted alkoxy, substituted aryl or unsubstituted aryl, substituted heteroaryl, unsubstituted heteroaryl, substituted arylalkyl, unsubstituted arylalkyl, —S(O)$_t$ NR$^{13}$R$^{14}$, —S(O)$_t$R$^{13}$ (e.g., —SO$_2$aryl (such as —SO$_2$phenyl), —SO$_2$cycloalkyl (such as —SO$_2$cyclopropyl), —SO$_2$alkyl (such as —SO$_2$isopropyl)), —SO$_2$fluoroalkyl (such as —SO$_2$CF$_3$), —C(O)$_2$R$^{13}$, —C(O)NR$^{13}$R$^{14}$ and —C(O)R$^{13}$;

R$^{11}$ and R$^{12}$ are independently selected from the group consisting of: hydrogen, unsubstituted alkyl, substituted alkyl, unsubstituted aryl, substituted aryl, unsubstituted alkylaryl, substituted alkylaryl, unsubstituted arylalkyl, substituted arylalkyl, unsubstituted cycloalkyl, substituted cycloalkyl, carboxyalkyl (e.g., -alkylCOOH, such as CH$_2$COOH), aminoalkyl, unsubstituted heteroaryl, substituted heteroaryl, unsubstituted heteroarylalkyl, substituted heteroarylalkyl, unsubstituted heterocycloalkylalkyl, substituted heterocycloalkylalkyl, unsubstituted cycloalkylalkyl, substituted cycloalkylalkyl, unsubstituted heterocyclic, substituted heterocyclic, unsubstituted fluoroalkyl, and substituted fluoroalkyl; or R$^{11}$ and R$^{12}$, together with the nitrogen atom to which they are bound to in the groups —C(O)NR$^{11}$R$^{12}$ and —SO$_{(t)}$ NR$^{11}$R$^{12}$, form an unsubstituted or substituted saturated heterocyclic ring, said ring optionally containing 1 to 3 additional heteroatoms wherein said optional heteroatoms are selected from the group consisting of O, S and —N(R$^{15}$), wherein there are optionally 1 to 3 substituents on the substituted cyclized R$^{11}$ and R$^{12}$ groups and each substituent is independently selected from the group consisting of alkyl, aryl, hydroxy, cyano, hydroxyalkyl, alkoxy, alkoxyalkyl, arylalkyl, fluoroalkyl, cycloalkyl, cycloalkylalkyl, heteroaryl, heteroarylalkyl, amino, aminoalkyl, —C(O)OR$^{13}$, —C(O)NR$^{13}$R$^{14}$, —S(O)$_t$NR$^{13}$R$^{14}$, —C(O)R$^{13}$, —SO$_2$R$^{13}$, —NHC(O)NR$^{13}$R$^{14}$, —NHC(O)OR$^{13}$, halogen, and —N(R$^{15}$)$_2$ wherein each R$^{15}$ is independently selected;

R$^{13}$ and R$^{14}$ independently selected from the group consisting of: H, unsubstituted alkyl, substituted alkyl, unsubstituted aryl, substituted aryl, unsubstituted arylalkyl, substituted arylalkyl, unsubstituted heteroaryl, substituted heteroaryl, unsubstituted cycloalkyl, substituted cycloalkyl, unsubstituted heteroarylalkyl, and substituted heteroarylalkyl;

R$^{15}$ is selected from the group consisting of: H, unsubstituted alkyl, substituted alkyl, unsubstituted fluoroalkyl, substituted fluoroalkyl, unsubstituted aryl, substituted aryl, unsubstituted heteroaryl, substituted heteroaryl, unsubstituted arylalkyl, substituted arylalkyl, —C(O)$_2$R$^{13}$, —C(O)NR$^{13}$R$^{14}$, —S(O)$_t$NR$^{13}$R$^{14}$, —C(O)R$^{13}$ and —SO$_2$R$^{13}$;

R$^{16}$ is selected from the group consisting of: substituted alkyl, unsubstituted alkyl, substituted fluoroalkyl, unsubstituted fluoroalkyl, substituted aryl, unsubstituted aryl, substituted heteroaryl and unsubstituted heteroaryl;

R$^{17}$ is selected from the group consisting of: alkyl, substituted alkyl, unsubstituted alkyl, substituted aryl, unsubstituted aryl, substituted heteroaryl, unsubstituted heteroaryl, unsubstituted fluoroalkyl, substituted fluoroalkyl, unsubstituted arylalkyl, substituted arylalkyl, unsubstituted heteroarylalkyl, substituted heteroarylalkyl, substituted cycloalkyl and unsubstituted cycloalkyl;

wherein when said substituted R$^1$, R$^3$, R$^4$, R$^5$, R$^{11}$, R$^{12}$, R$^{13}$, R$^{14}$, R$^{15}$, R$^{16}$, and R$^{17}$ groups are other than substituted alkyl, then the substituents for said substituted R$^1$, R$^3$, R$^4$, R$^5$, R$^{11}$, R$^{12}$, R$^{13}$, R$^{14}$, R$^{15}$, R$^{16}$, and R$^{17}$ groups are independently selected from the group consisting of: alkyl, —CF$_3$, —OH, alkoxy, hydroxyalkyl (e.g., —CH$_2$OH), aryl, arylalkyl, aminoalkyl (e.g., —CH$_2$N(R$^{15}$)$_2$, wherein each R$^{15}$ is as defined above and each R$^{15}$ is the same or different), fluoroalkyl, fluoroalkoxy, cycloalkyl, cycloalkylaryl, heteroaryl, heteroarylalkyl, halogen, —C(O)$_2$R$^{13a}$, —C(O)NR$^{13a}$R$^{14a}$, —S(O)$_t$NR$^{13a}$R$^{14a}$, —C(O)R$^{13a}$, SO$_2$R$^{13a}$, and —N(R$^{15a}$)$_2$, wherein each R$^{13a}$, R$^{14a}$, an R$^{15a}$ is independently selected from the group consisting of unsubstituted alkyl (e.g., methyl, ethyl and isopropyl), unsubstituted aryl (e.g., phenyl), halo substituted aryl (e.g., chlorophenyl (e.g., 3-chlorophenyl) and fluorophenyl (e.g., 3-fluorophenyl)), unsubstituted arylalkyl (e.g., benzyl), halo substituted arylalkyl (e.g., fluorobenzyl (e.g., 3-fluorobenzyl), and chlorobenzyl (e.g., 3-chlorobenzyl)), and unsubstituted cycloalkyl (e.g., cyclohexyl and cyclopropyl), except that the cyclized R$^{11}$ and R$^{12}$ are optionally substituted as provided above;

wherein when said substituted R$^1$, R$^3$, R$^4$, R$^5$, R$^{11}$, R$^{12}$, R$^{13}$, R$^{14}$, R$^{15}$, R$^{16}$, and R$^{17}$ groups are substituted alkyl, then the substituents for said substituted R$^1$, R$^3$, R$^4$, R$^5$, R$^{11}$, R$^{12}$, R$^{13}$, R$^{14}$, R$^{15}$, R$^{16}$, and R$^{17}$ groups are independently selected from the group consisting of: —CF$_3$, —OH, alkoxy, hydroxyalkyl (e.g., —CH$_2$OH), aryl, arylalkyl, aminoalkyl (e.g., —CH$_2$N(R$^{15}$)$_2$, wherein each R$^{15}$ is as defined above and each R$^{15}$ is the same or different), fluoroalkyl, fluoroalkoxy, cycloalkyl, cycloalkylaryl, heteroaryl, heteroarylalkyl, halogen, —C(O)$_2$R$^{13a}$, —C(O)NR$^{13a}$R$^{14a}$, —S(O)$_t$NR$^{13a}$R$^{14a}$, —C(O)R$^{13a}$, —SO$_2$R$^{13a}$, and —N(R$^{15a}$)$_2$, wherein each R$^{13a}$, R$^{14a}$, and R$^{15a}$ is independently selected from the group consisting of unsubstituted alkyl (e.g., methyl, ethyl and isopropyl), unsubstituted aryl (e.g., phenyl), halo substituted aryl (e.g., chlorophenyl (e.g., 3-chlorophenyl) and fluorophenyl (e.g., 3-fluorophenyl)), unsubstituted arylalkyl (e.g., benzyl), halo substituted arylalkyl (e.g., fluorobenzyl (e.g., 3-fluorobenzyl), and chlorobenzyl (e.g., 3-chlorobenzyl)), and unsubstituted cycloalkyl (e.g., cyclohexyl and cyclopropyl), except that the cyclized R$^{11}$ and R$^{12}$ are optionally substituted as provided above; and t is 1 or 2.

In one embodiment of the compound of formula (1), the substituted Y groups are substituted with 1-5, or 1-3 (e.g., 1, or 1-2, or 1-3) substituents independently selected from the group consisting of (a) alkyl, (b) alkyl substituted with 1-3 (e.g., 1, 1-2, or 1-3) substituents selected from the group consisting at —OH and —N(R$^{15}$)$_2$ wherein each R$^{15}$ is independently selected, (c) alkoxy, (d) fluoroalkyl, (e) fluoroalkoxy, (f) halo (e.g., Br, F, I), (g) —CN and (h) —OH.

In another embodiment of the compounds of formula (1), Y is selected from the group consisting of:

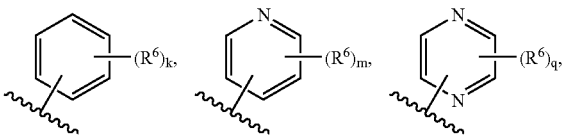

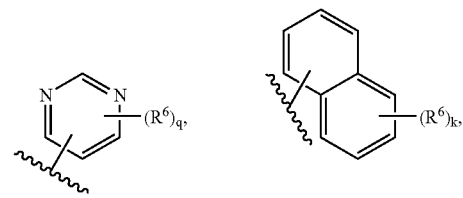

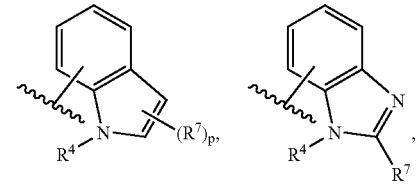

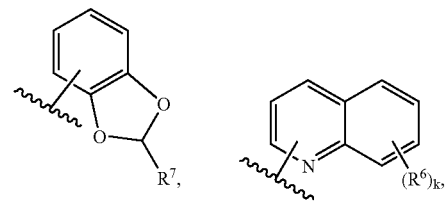

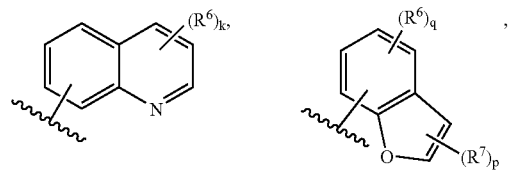

-continued

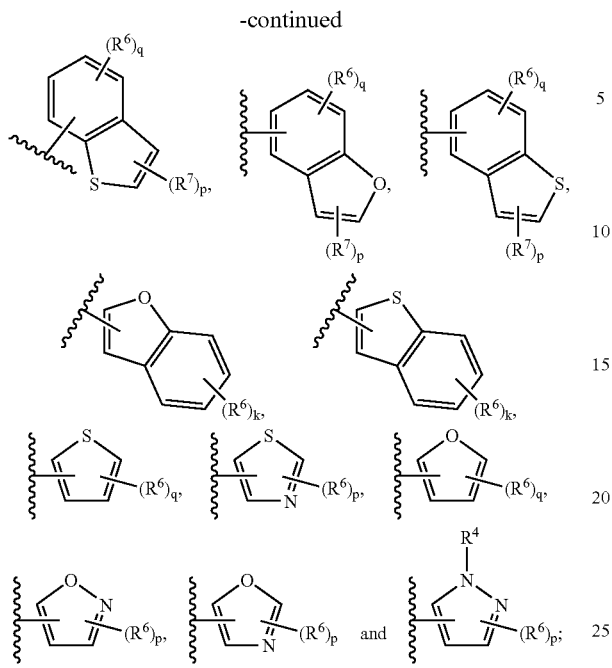

wherein:
k=0 to 5;
m=0 to 4;
q=0 to 3;
p=0 to 2;
$R^6$ and $R^7$ are independently selected from the group consisting of: —OH, halogen, cyano, —$CF_3$, —$OCF_3$, —$NR^{11}R^{12}$, —$NR^{11}(CO)NR^{11}R^{12}$, —$C(O)NR^{11}R^{R12}$, —$CO_2R^{11}$, —$OR^{11}$, —$SO_{(t)}NR^{11}R^{12}$, —$NR^{11}S_{(t)}R^{12}$, —$COR^{11}$, substituted aryl, unsubstituted aryl, substituted alkyl, unsubstituted alkyl, substituted alkoxy, unsubstituted alkoxy, substituted arylalkyl, unsubstituted arylalkyl, substituted heteroaryl, unsubstituted heteroaryl, substituted aryloxy, unsubstituted aryloxy, substituted heteroarylalkyl, unsubstituted heteroarylalkyl, substituted heteroarylalkoxy, unsubstituted heteroarylalkoxy, substituted heterocycloalkyl, unsubstituted heterocycloalkyl, substituted hydroxyalkyl, and unsubstituted hydroxyalkyl;
wherein the $R^6$ groups are substituted with 1-6 substituents (e.g., 1, or 1-2, or 1-3, or 1-4, or 1-5, or 1-6), and the substituted $R^7$ groups are optionally substituted with 1 to 6 substituents, and each substituent on said substituted $R^6$ group and each substituent on said substituted $R^7$ group is independently selected from the group consisting of: $R^{11}$, halogen, —$CF_3$, —$COR^{11}$, —$OR^{11}$, —$NR^{11}R^{12}$, —$NO_2$, —CN, —$SO_2R^{11}$, —$SO_2NR^{11}R^{12}$, —$NR^{11}C(O)R^{12}$, —$C(O)NR^{11}R^{12}$, —$NR^{11}CO_2R^{12}$ and —$CO_2R^{11}$.

In still another embodiment of the compounds of formula (1), 5-het is selected from the group consisting of:

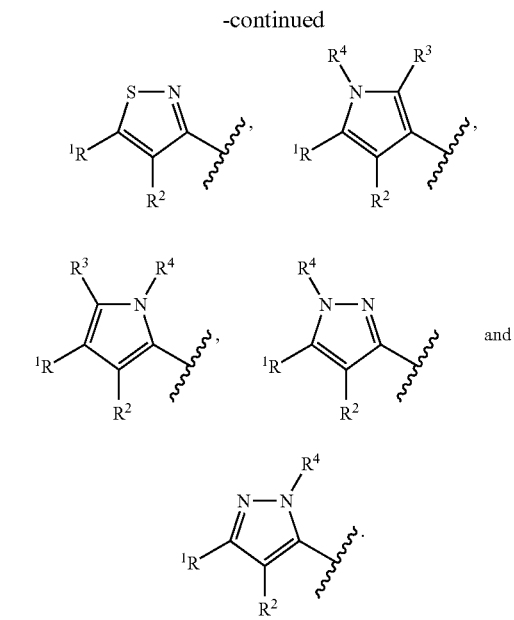

In still another embodiment of the compounds of formula (1), 5-het is selected from the group consisting of:

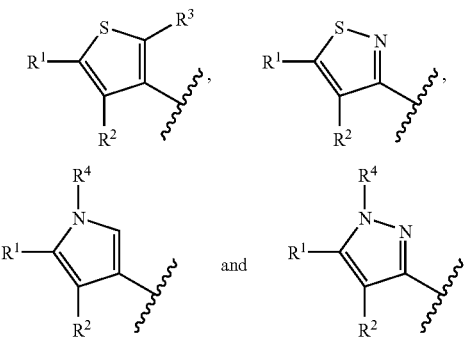

Q is selected from the group consisting of:

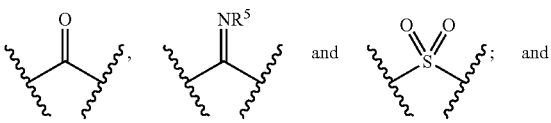

Y is selected from the group consisting of:

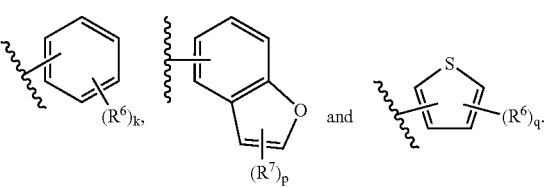

In still yet another embodiment of the compounds of formula (1), 5-het is selected from the group consisting of:

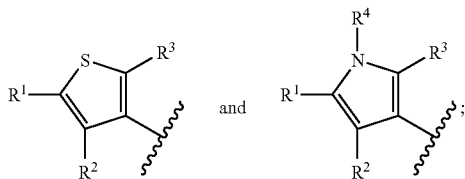

Q is selected from the group consisting of:

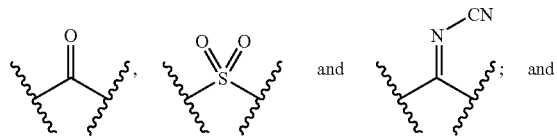

Y is selected from the group consisting of:

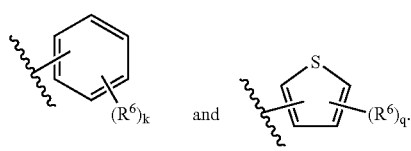

In another aspect of the compounds of formula (1), 5-het is:

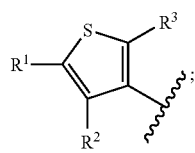

Q is selected from the group consisting of:

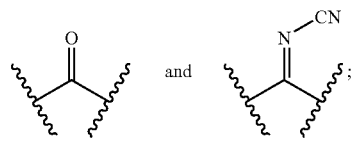

Y is:

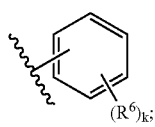

(e.g., k is 2 and each $R^6$ is independently selected)
$R^1$ is selected from the group consisting of —SO$^{(t)}$NR$^{11}$R$^{12}$ and —SO$_{(t)}$R$^{11}$;
$R^2$ is —OH or —OC(O)NHR$^{16}$;
$R^3$ is selected from the group consisting of: H, alkyl, halogen and —CF$_3$; and $R^6$ is halogen or alkyl.

In still another aspect of the compounds of the formula (1):

$R^1$ is —SO$_2$NR$^{11}$R$^{12}$;

$R^3$ is selected from the group consisting of: H, Cl and —CF$_3$;

$R^{11}$ is selected from the group consisting of: H, unsubstituted alkyl, substituted alkyl, unsubstituted cycloalkyl and substituted cycloalkyl;

$R^{12}$ is selected from the group consisting of: H, unsubstituted alkyl, substituted alkyl, unsubstituted cycloalkyl and substituted cycloalkyl;

$R^2$ is —OH or —OC(O)NHR$^{16}$;

$R^{16}$ is selected from the group consisting of: alkyl, aryl and heteroaryl; and Y is

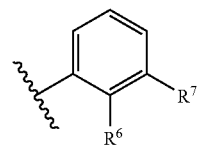

wherein $R^6$ and $R^7$ are as defined above.

In still yet another aspect of the compounds of formula (1), 5-het is selected from the group consisting of:

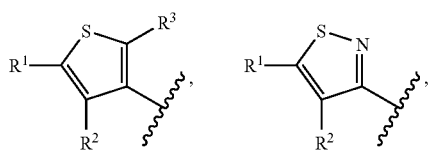

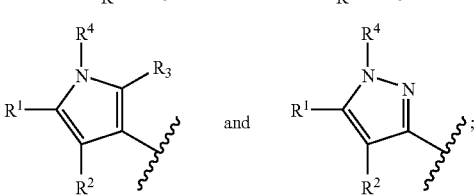

$R^1$ is selected from the group consisting of:

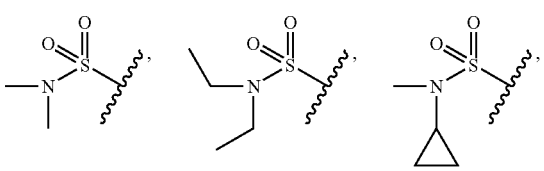

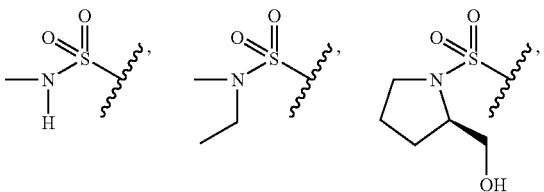

-continued

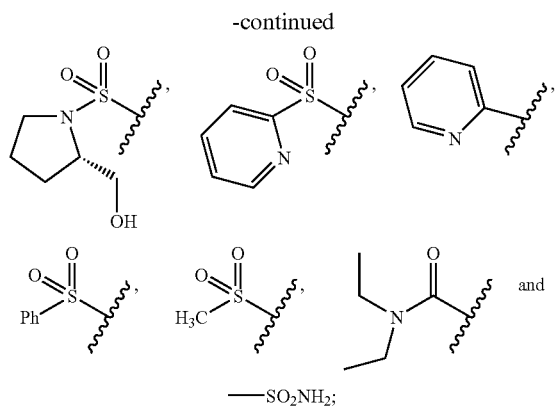

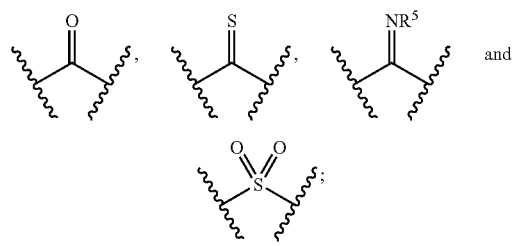

—SO₂NH₂;

R² is selected from the group consisting of: —OH, —OC(O)NHCH₂CH₃, —OC(O)NHCH(CH₃)₂, and —NH-COCF₃;

R³, when n is 1, is selected from the group consisting of: H, Cl, —CF₃ and —CH₃;

R⁴, when n' is 1, is CH₃;

Q is selected from the group consisting of:

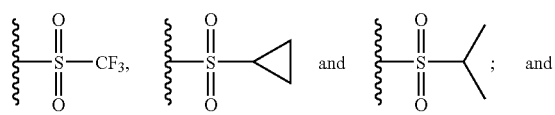

R⁵ is selected from the group consisting of: H, —CN, —SO₂Ph,

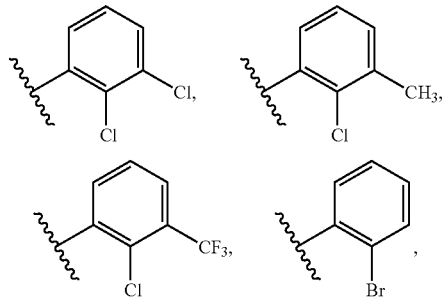

Y is selected from the group consisting of:

-continued

Thus, in one embodiment of the compounds of formula (1), 5-het is selected from the group consisting of:

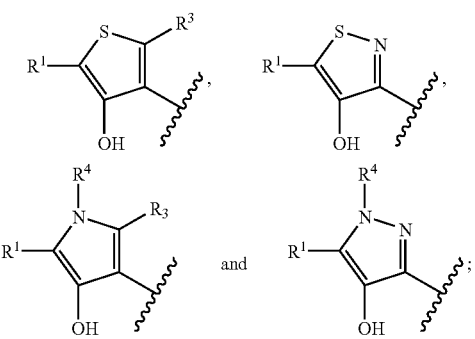

R¹ is selected from the group consisting of:

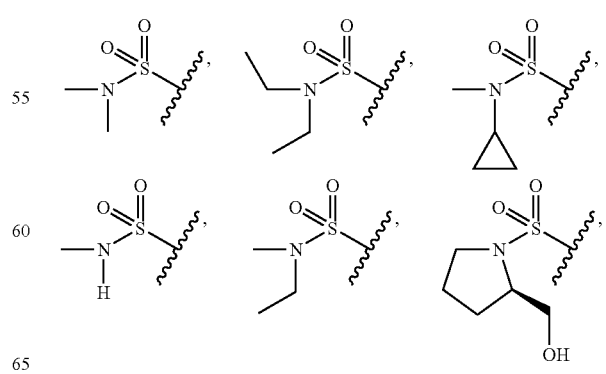

-continued

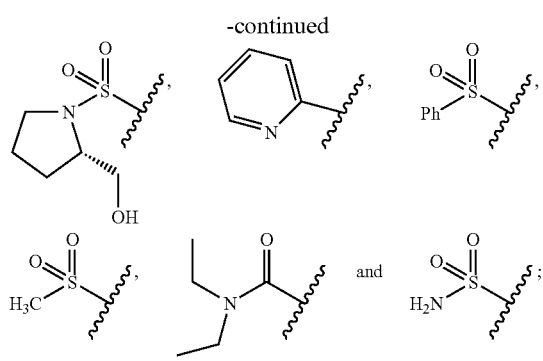

$R^5$ is —CN or

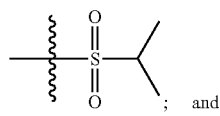
; and

Y is selected from the group consisting of:

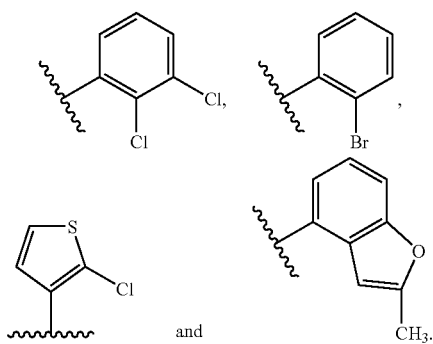

One embodiment of the compounds of this invention is directed to the compounds of formula 1 wherein $R^2$ is —OH, i.e., the compounds of formula:

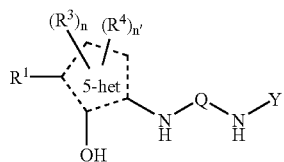

and the pharmaceutically acceptable salts (e.g., sodium or calcium salt) and solvates thereof, wherein $R^1$, $R^3$, $R^4$, n, n', Q and Y are as defined for formula 1 and the embodiments thereof.

Another embodiment of this invention is directed to the compounds of formula (2) wherein $R^1$ is selected from the group consisting of heteroaryl and aminosulfonyl (e.g., —S(O)$_2$NR$^{11}$R$^{12}$ wherein $R^{11}$ and $R^{12}$ are defined above, such as for example, —S(O)$_2$(CH$_2$CH$_3$)$_2$), and all other substituents are as defined above for formula 1.

Another embodiment of this invention is directed to the compounds of formula (2) wherein $R^1$ is —S(O)$_2$NR$^{11}$R$^{12}$, and all other substituents are as defined above for formula 1.

Another embodiment of this invention is directed to the compounds of formula (2) wherein $R^1$ is —S(O)$_2$NR$^{11}$R$^{12}$ and $R^{11}$ and $R^{12}$ are selected from the group consisting of: H, unsubstituted alkyl, substituted alkyl, unsubstituted cycloalkyl, substituted cycloalkyl, and the unsubstituted or substituted saturated heterocyclic ring formed when $R^{11}$ and $R^{12}$ are taken together with the nitrogen atom to which they are bound, and all other substituents are as defined above for formula 1.

Another embodiment of this invention is directed to the compounds of formula (2) wherein $R^1$ is —S(O)$_2$NR$^{11}$R$^{12}$ and $R^{11}$ and $R^{12}$ are selected from the group consisting of: unsubstituted alkyl, substituted alkyl, unsubstituted cycloalkyl, substituted cycloalkyl, and the unsubstituted or substituted saturated heterocyclic ring formed when $R^{11}$ and $R^{12}$ are taken together with the nitrogen atom to which they are bound, and all other substituents are as defined above for formula 1.

Another embodiment of this invention is directed to the compounds of formula (2) wherein $R^1$ is —S(O)$_2$NR$^{11}$R$^{12}$ and $R^{11}$ and $R^{12}$ are selected from the group consisting of: unsubstituted alkyl (e.g., methyl) and unsubstituted cycloalkyl, and all other substituents are as defined above for formula 1.

Additional embodiments are described below. The embodiments have been numbered for purposes of reference Embodiment No. 1 is directed to a compound of the formula (1) wherein 5-het is selected from the group consisting of:

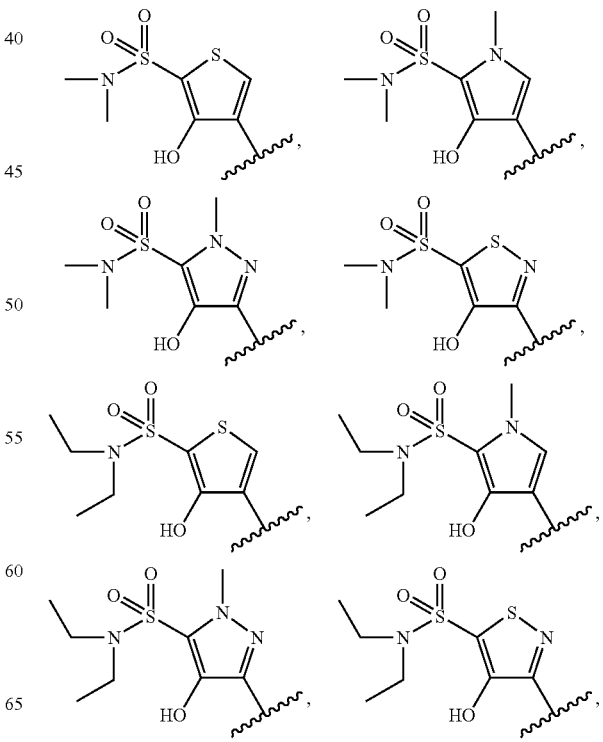

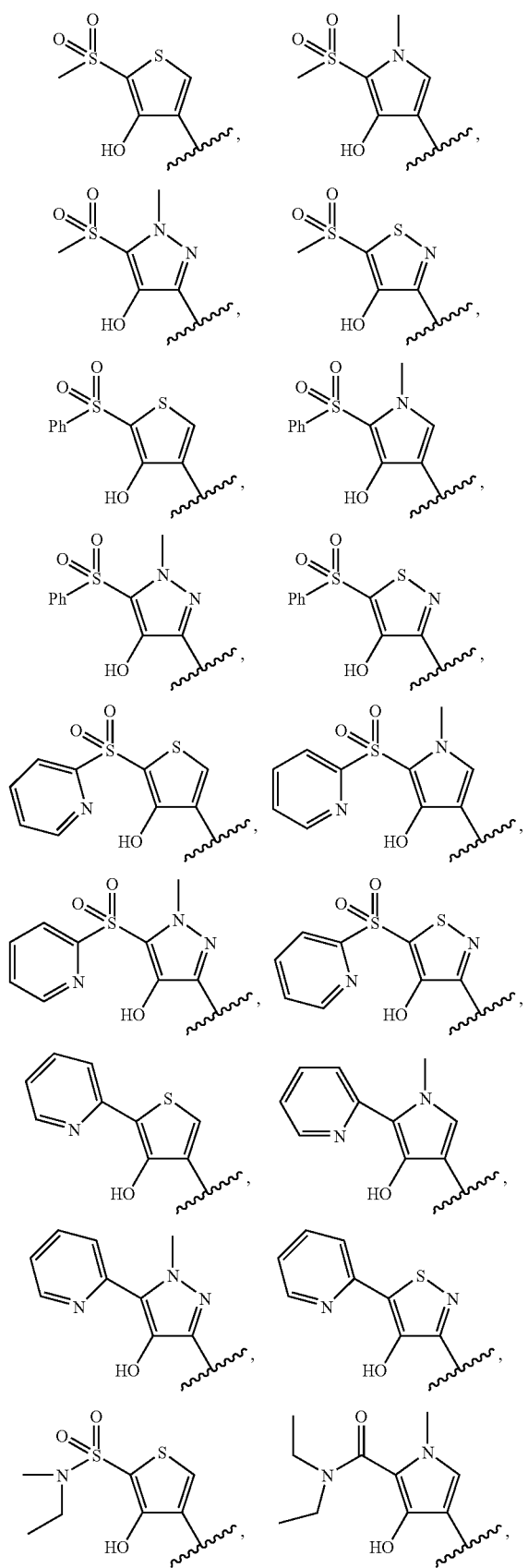
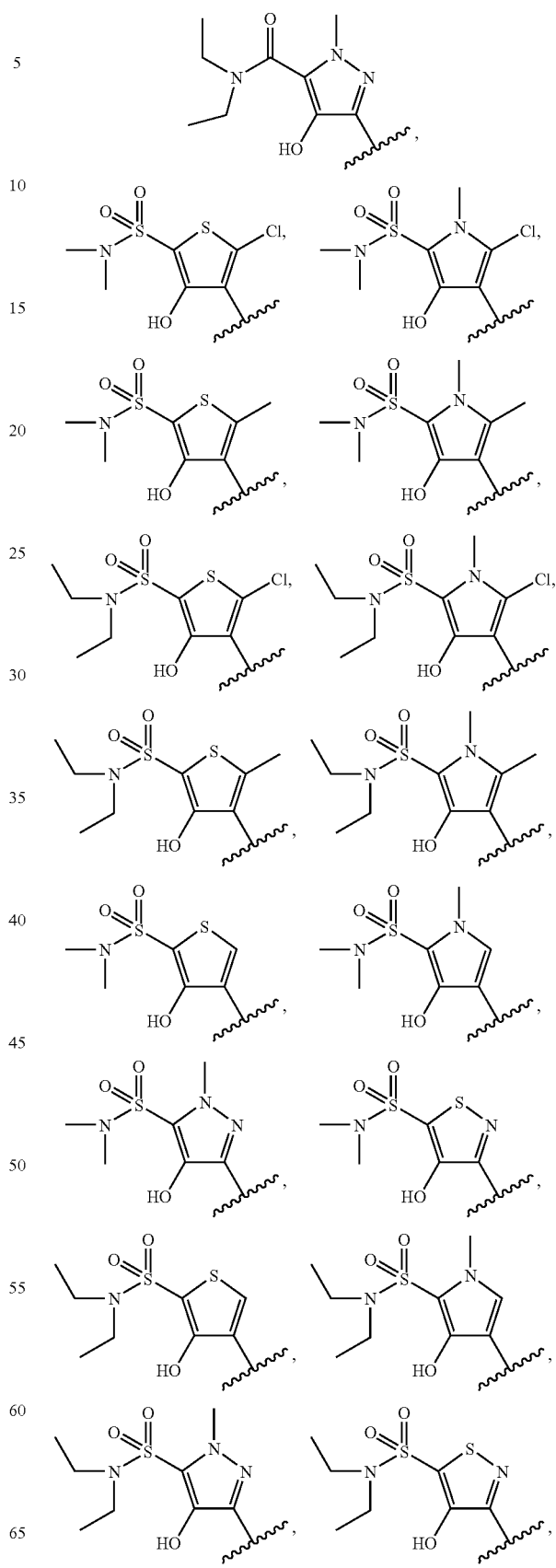

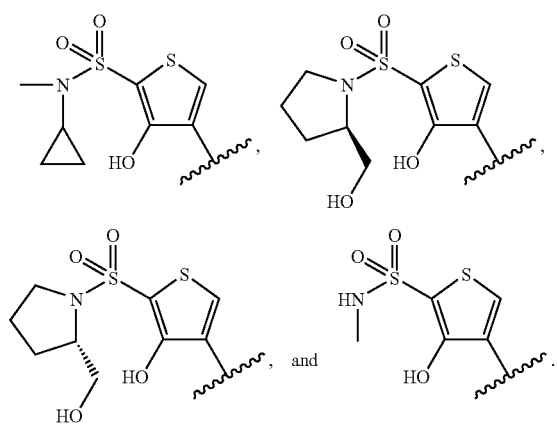
Embodiment No. 2 is directed to urea compounds of Embodiment No. 1 wherein 5-het is coupled to a moiety selected from the group consisting of:
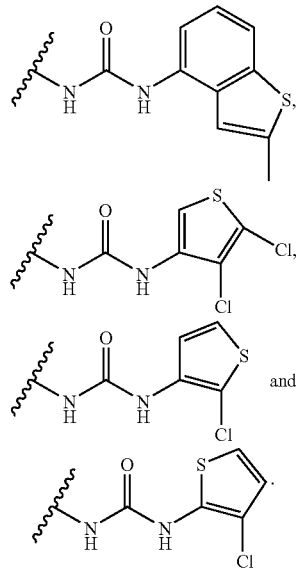
Embodiment No. 3 is directed to thiourea compounds of Embodiment No. 1 wherein 5-het is coupled to a moiety selected from the group consisting of:
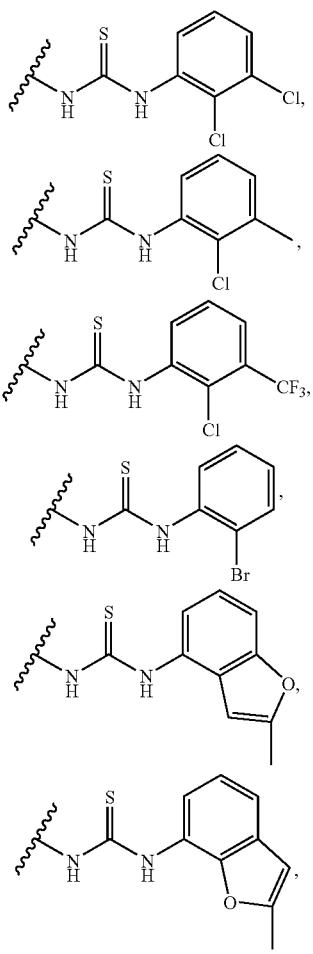

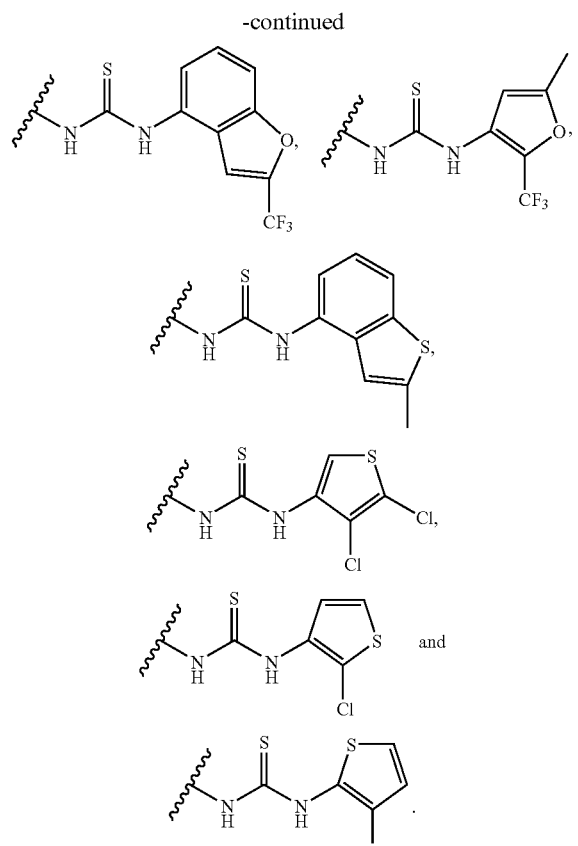
Embodiment No. 4 is directed to guanidine compounds of Embodiment No. 1 wherein 5-het is coupled to a moiety selected from the group consisting of:
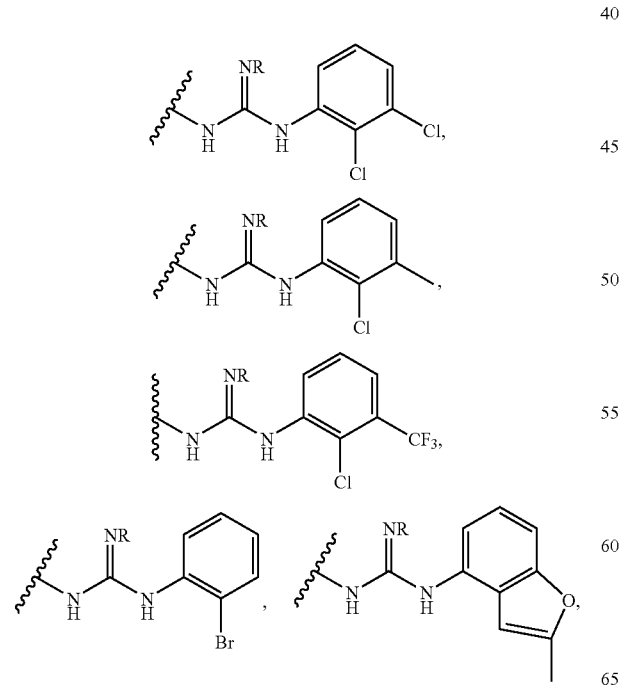
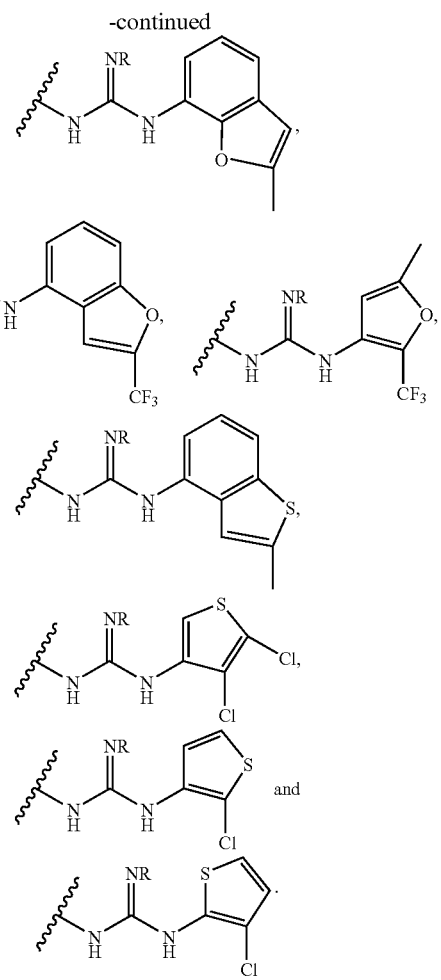
wherein R in Embodiment No. 4 is selected from the group consisting of:
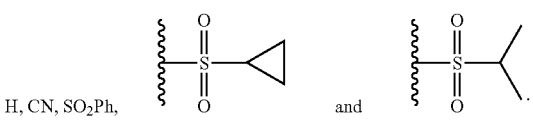
H, CN, SO₂Ph, and
Embodiment No. 5 is directed to sulfamide compounds of Embodiment No. 1 wherein 5-het is coupled to a moiety selected from the group consisting of:
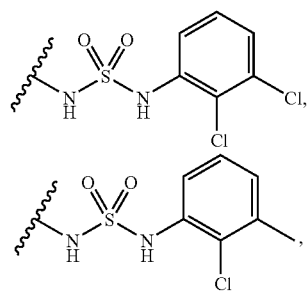

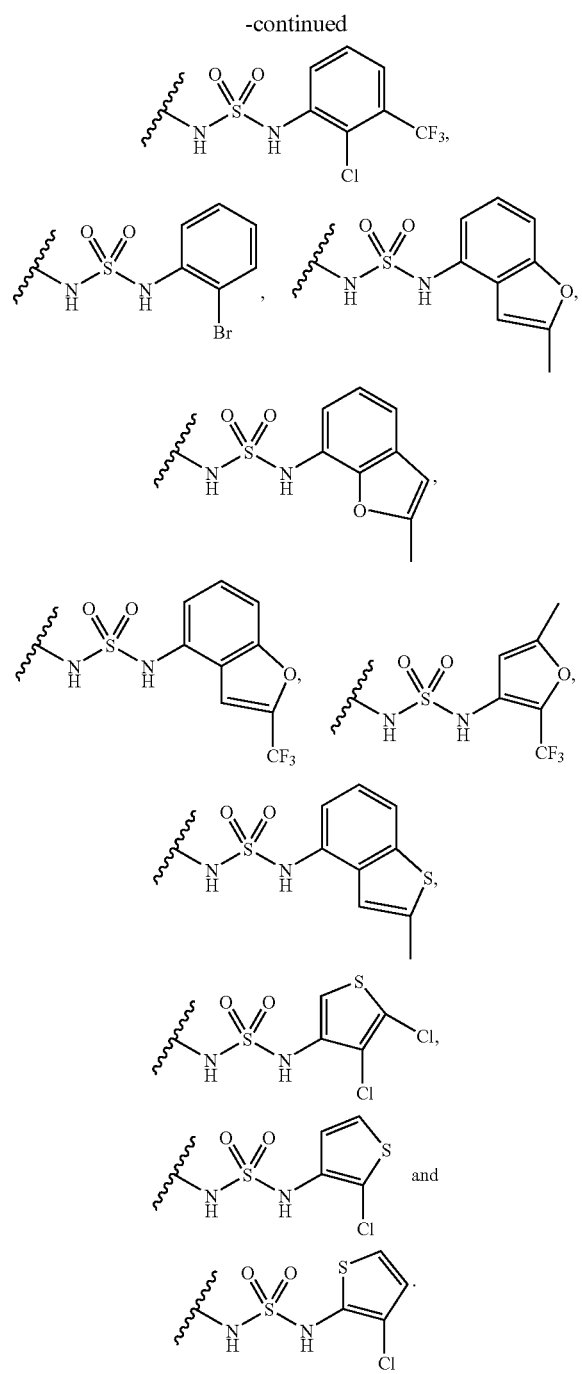
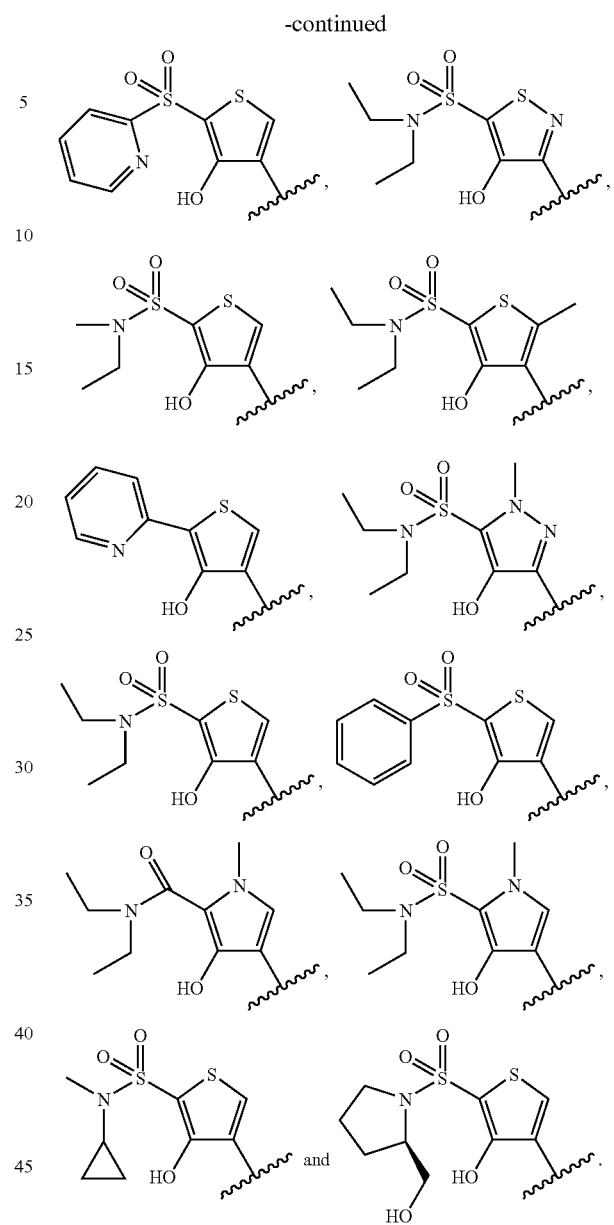
Embodiment No. 6 is directed to a compound of the formula (1) wherein 5-het is selected from the group consisting of:
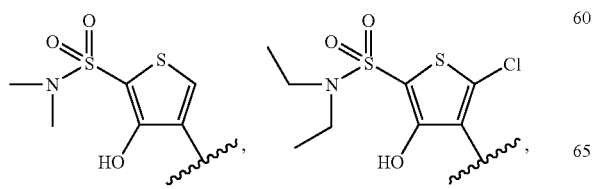
Embodiment No. 7 is directed to a compound of Embodiment No. 6 wherein 5-het is coupled to a moiety selected from the group consiting of:
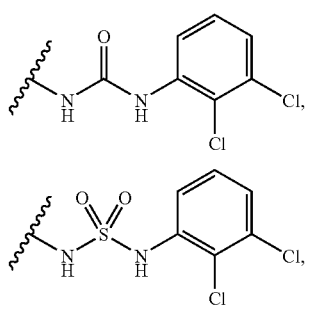

-continued
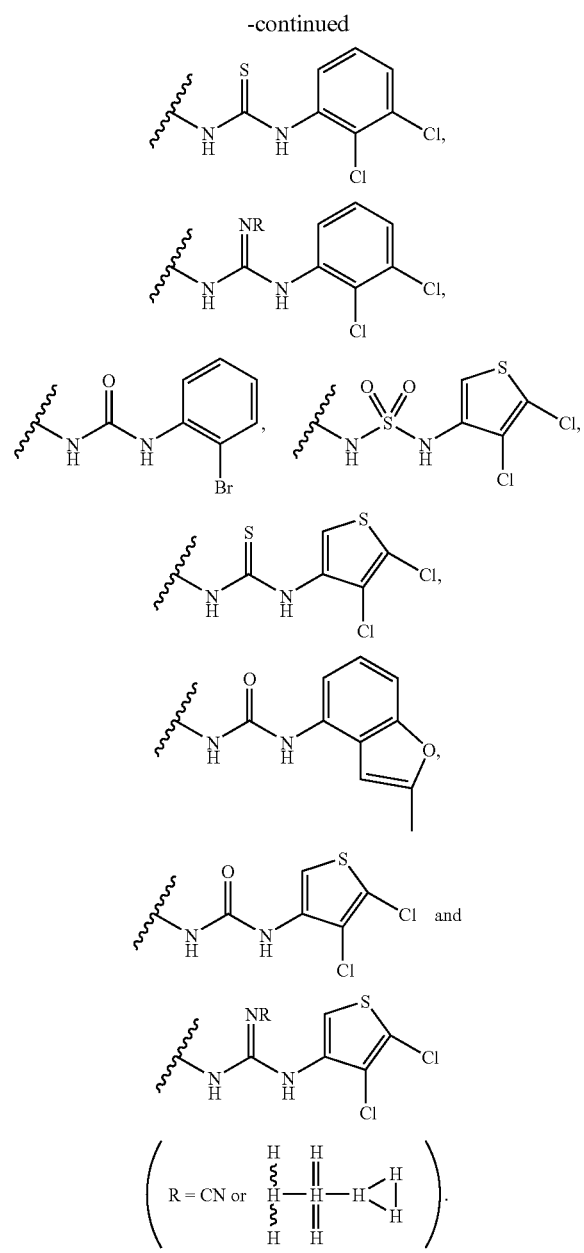
In another embodiment, the compounds of formula (1) are selected from the group consisting of:
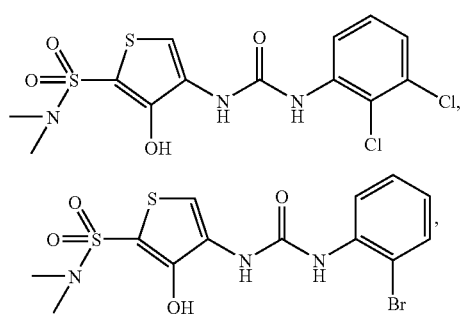
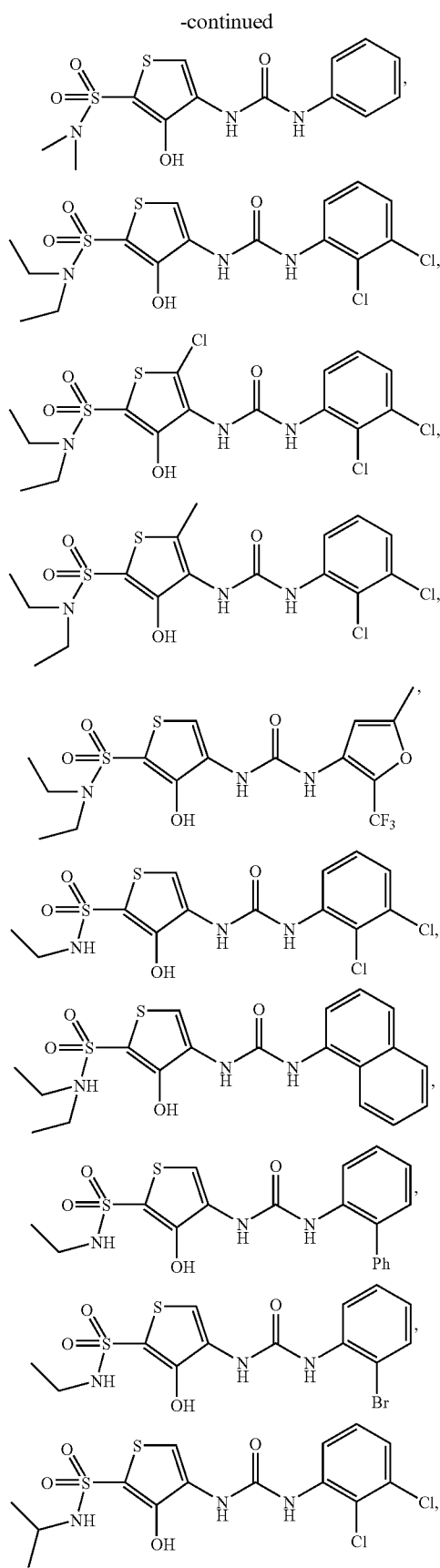

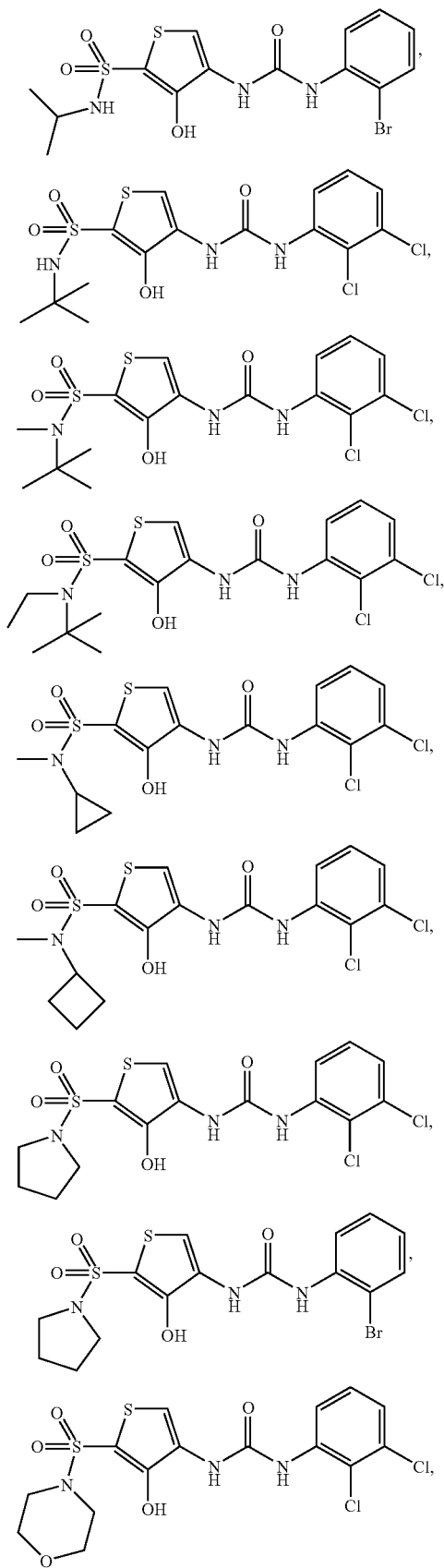
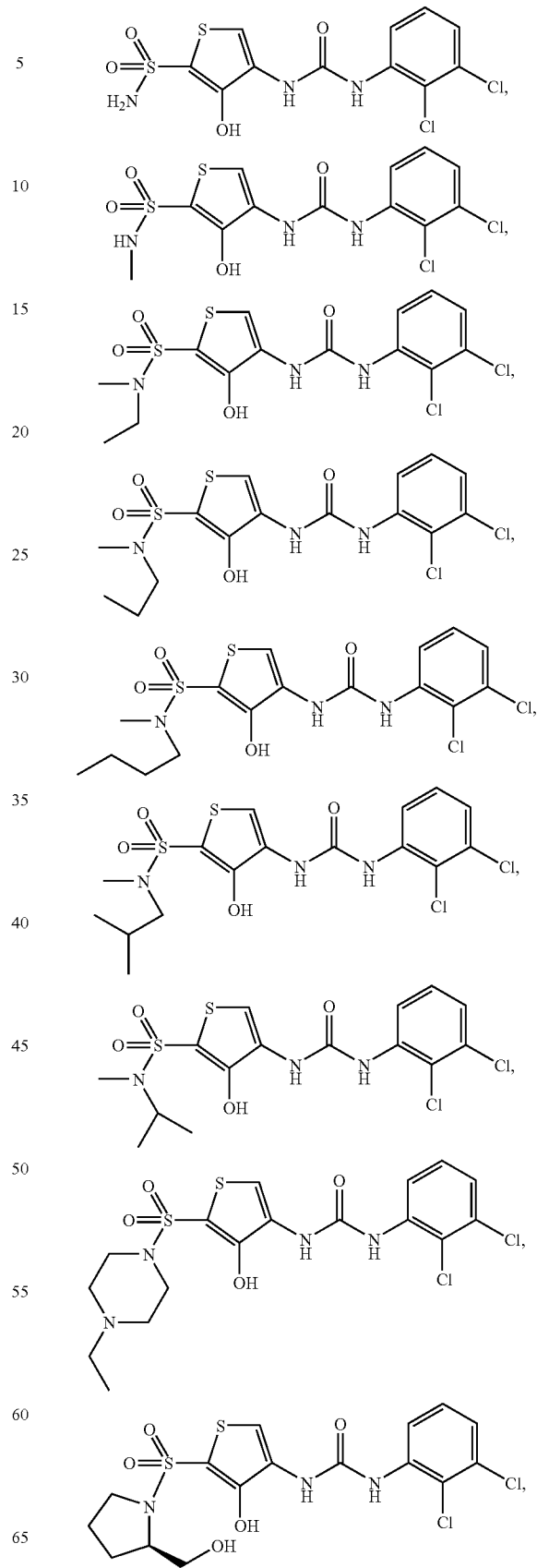

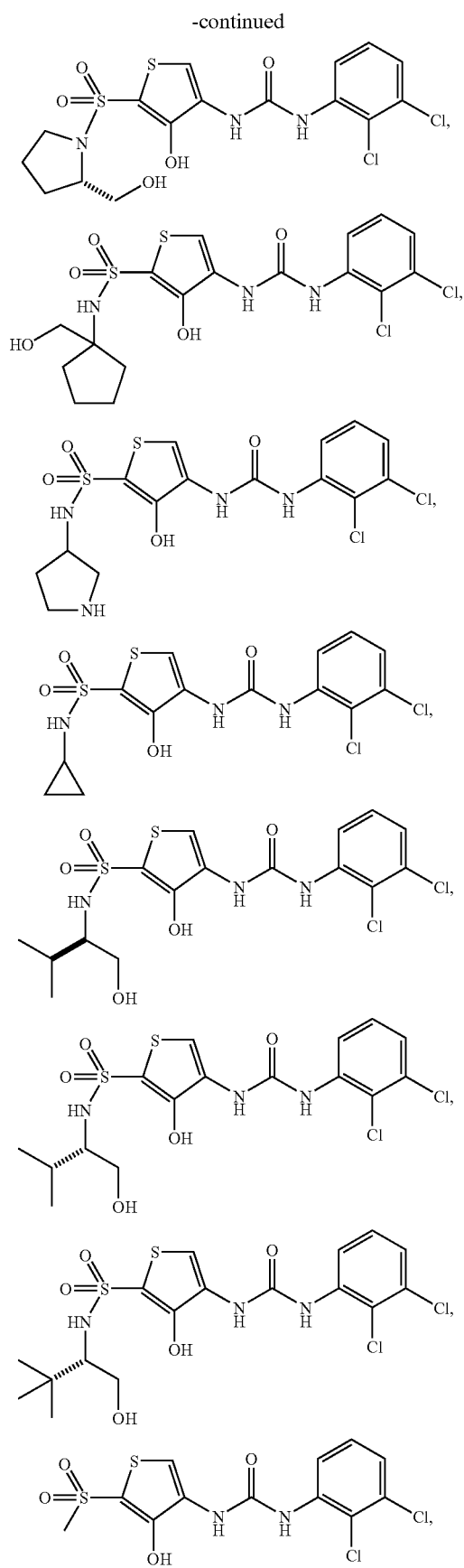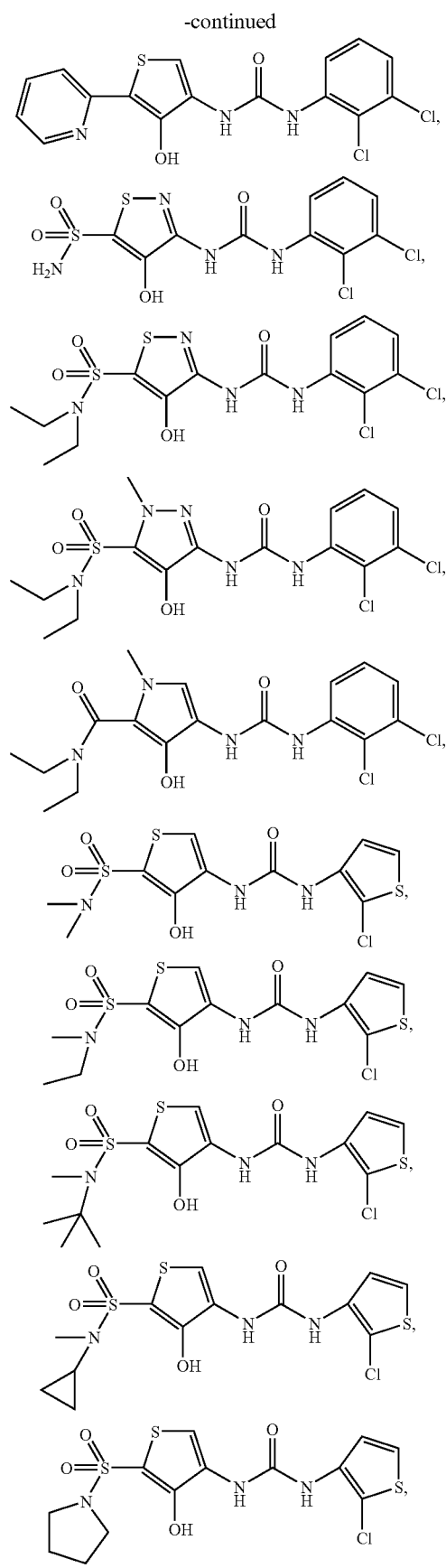

-continued
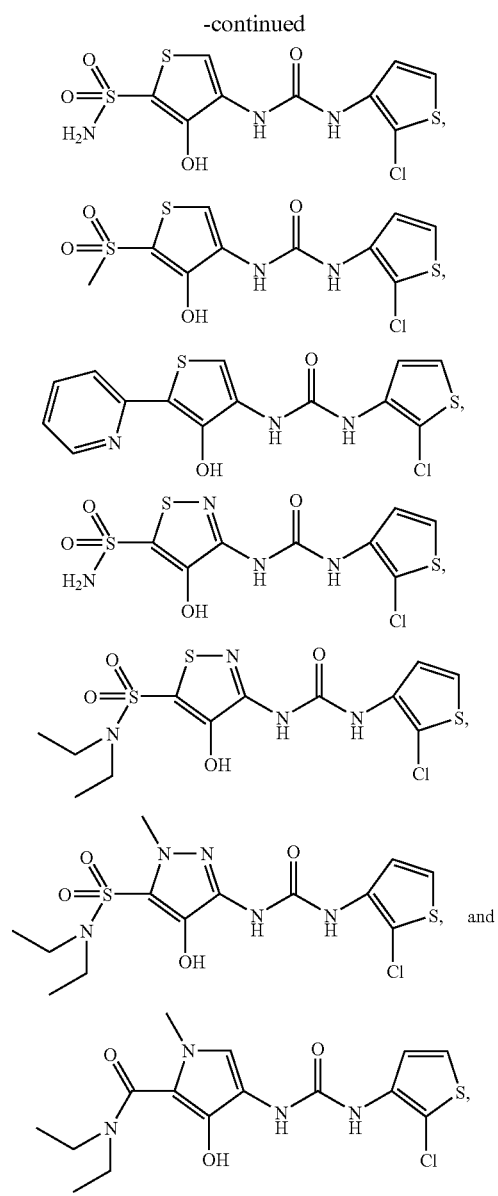
or a pharmaceutically acceptable salt, or solvate thereof.
In still another embodiment, the compounds of formula (1) are selected from the group consisting of:
-continued
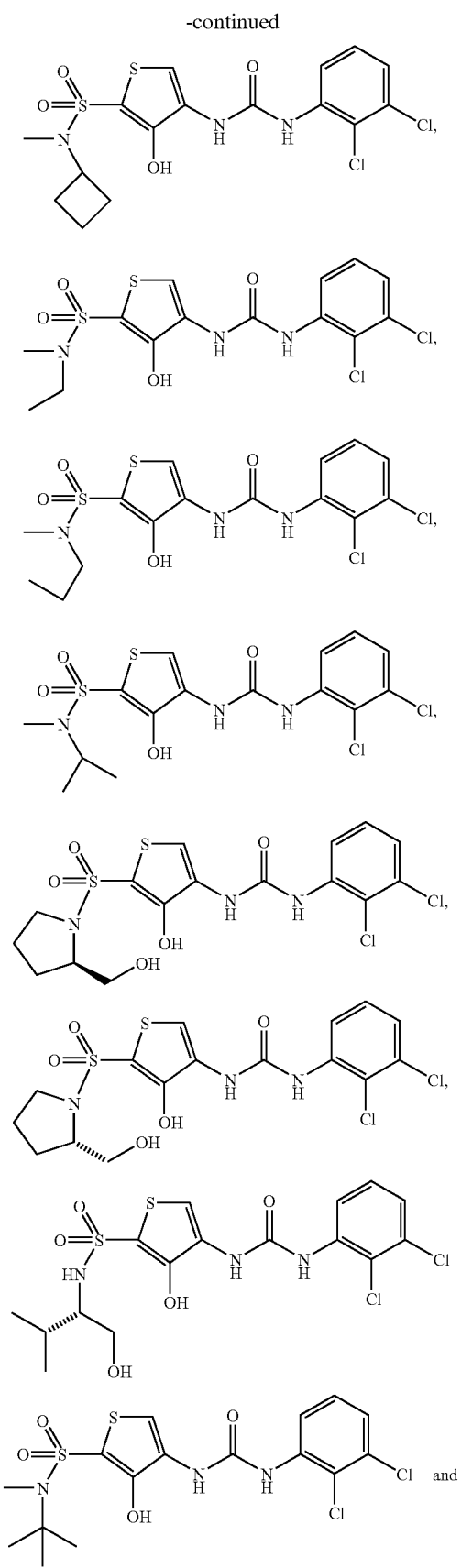

-continued

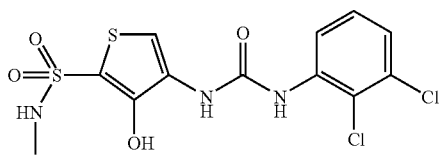

or a pharmaceutically acceptable salt, or solvate thereof.

In still another embodiment, the compound of formula (1) is:

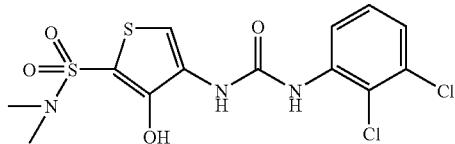

or a pharmaceutically acceptable salt, or solvate thereof.

In still another embodiment, the compound of formula (1) is:

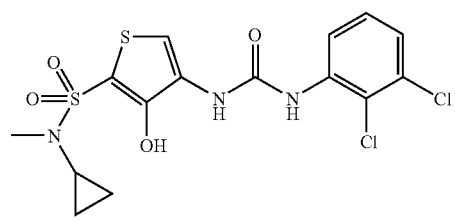

or a pharmaceutically acceptable salt, or solvate thereof.

In still another embodiment, the compound of formula (1) is:

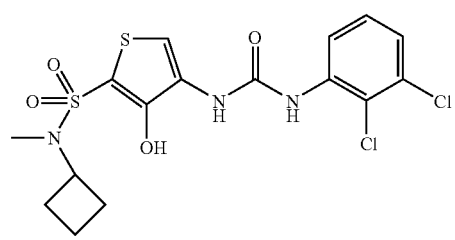

or a pharmaceutically acceptable salt, or solvate thereof.

In still another embodiment, the compound formula (1) is:

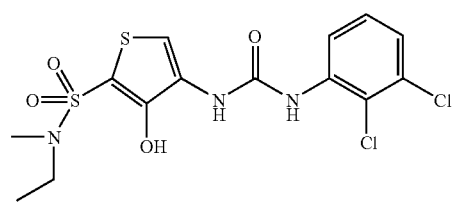

or a pharmaceutically salt, or solvent thereof.

In still another embodiment, the compound of formula (1) is:

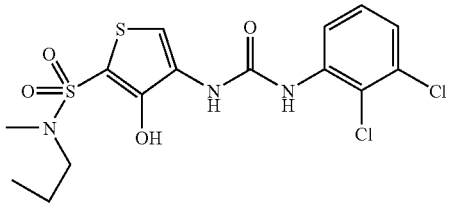

or a pharmaceutically acceptable salt, or solvate thereof.

In still another embodiment, the compound of formula (1) is:

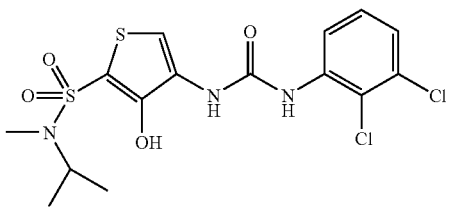

or a pharmaceutically acceptable salt, or solvate thereof.

In still another embodiment, the compound of formula (1) is:

or a pharmaceutically acceptable salt, or solvate thereof.

In still another embodiment, the compound of formula (1) is:

or a pharmaceutically acceptable salt, or solvate thereof.

In still another embodiment, the compound of formula (1) is:

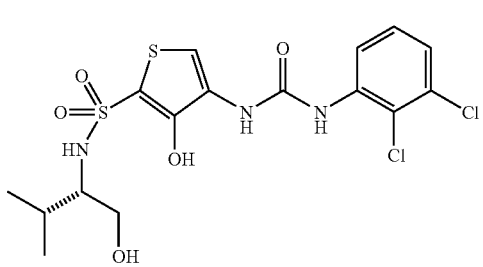

or a pharmaceutically acceptable salt, or solvate thereof.

In still another embodiment, the compound of formula (1) is:

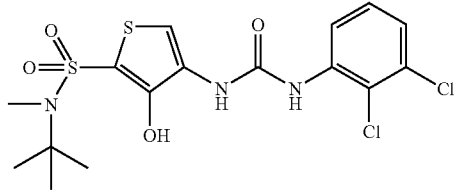

or a pharmaceutically acceptable salt, or solvate thereof.

In still another embodiment, the compound of formula (1) is:

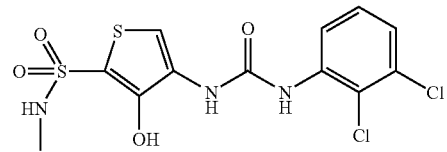

or a pharmaceutically acceptable salt, or solvate thereof.

In still another embodiment, the compounds of formula (1) are selected from the group consisting of:

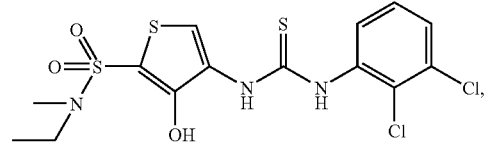

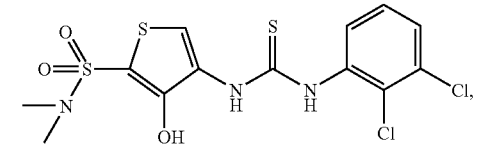

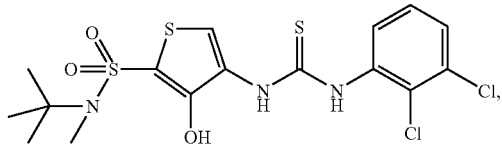

-continued

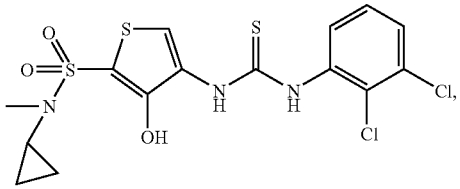

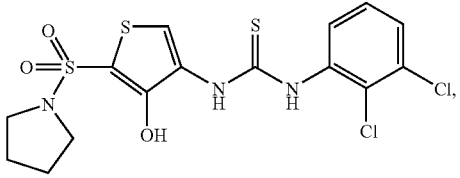

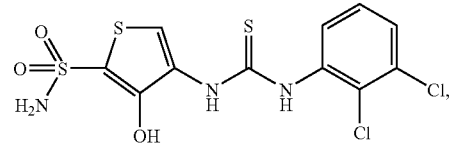

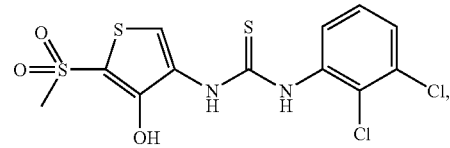

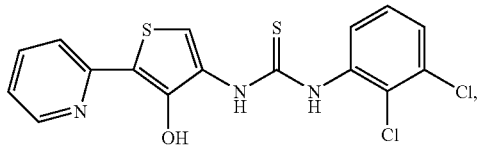

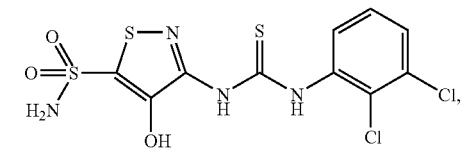

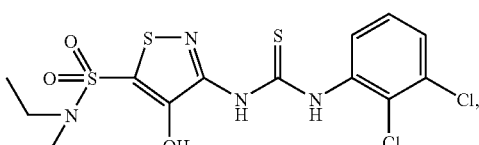

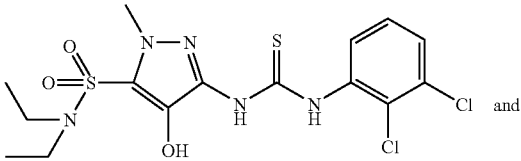

and

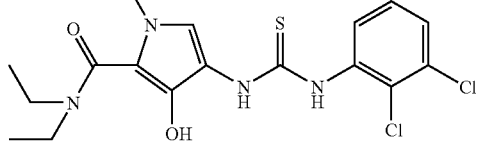

or a pharmaceutically acceptable salt, or solvate thereof.

In still another embodiment, the compounds of formula (1) are selected from the group consisting of:
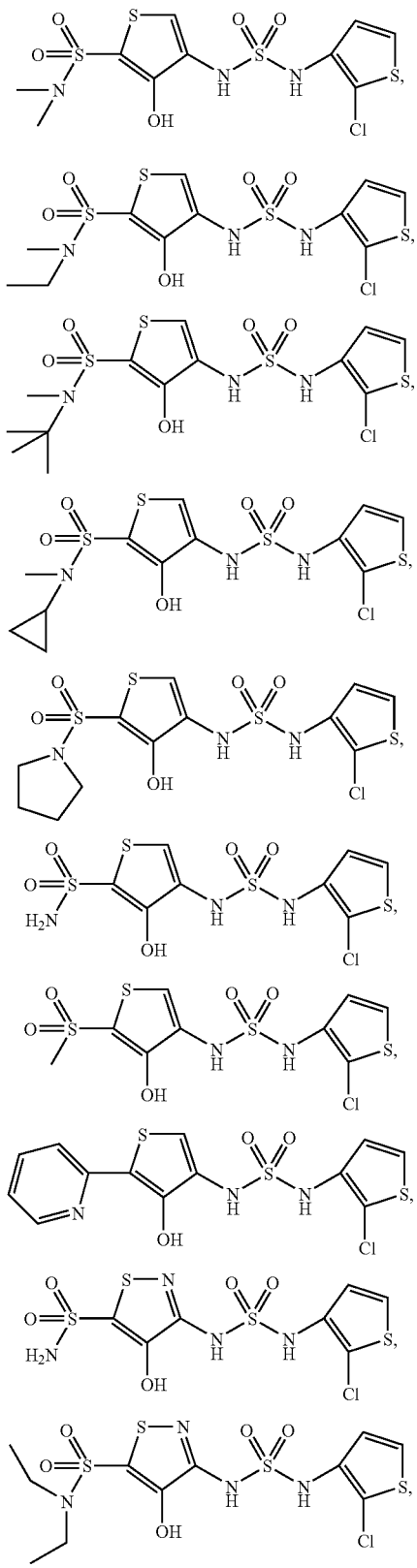
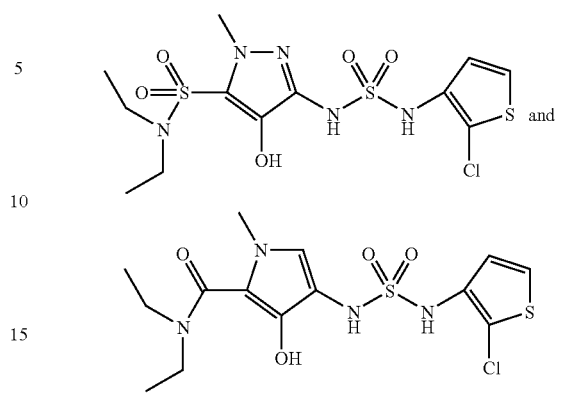
or a pharmaceutically acceptable salt, or solvate thereof.
In still another embodiment, the compounds of formula (1) are selected from the group consisting of:
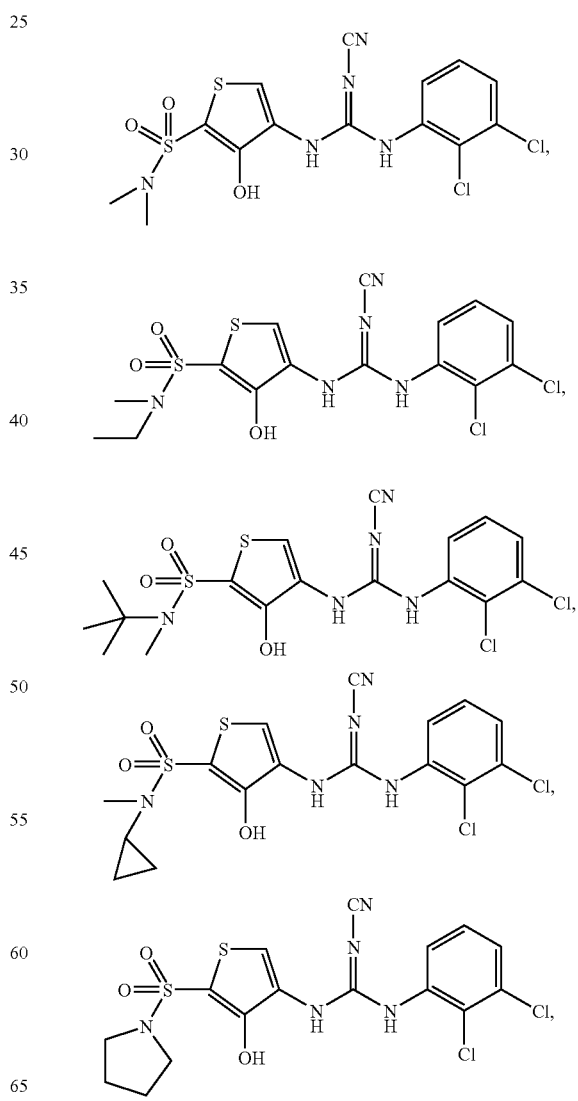

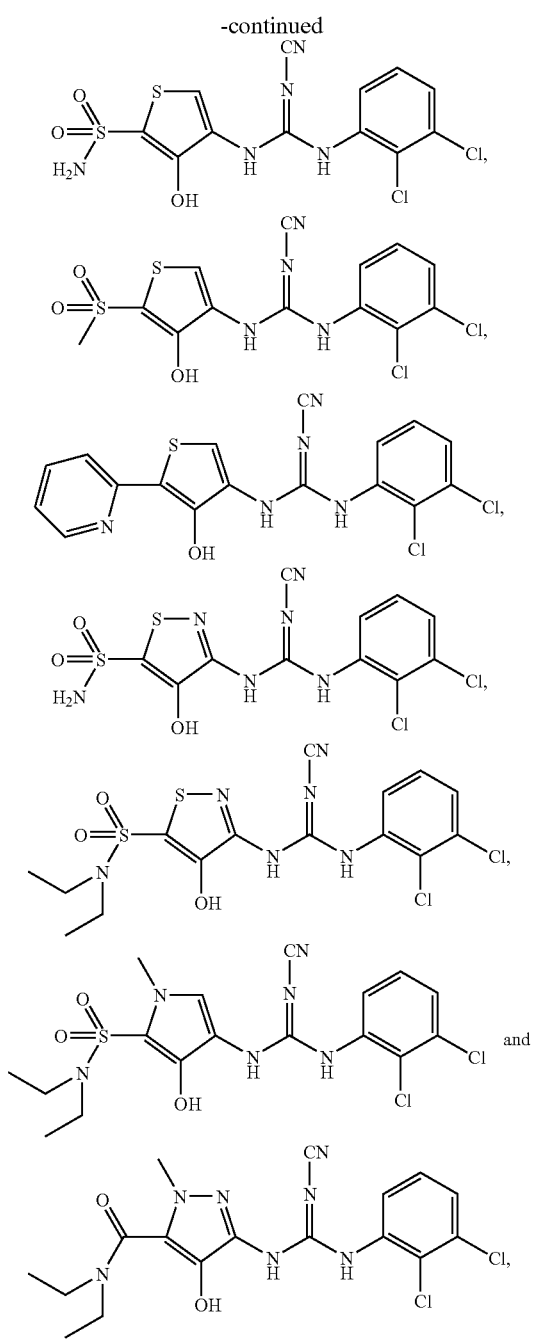

or a pharmaceutically acceptable salt, or solvate thereof.

Representative compounds of this invention are isolated in substantially pure form.

Another embodiment of this invention is directed to the compounds of formula (1) in isolated and pure form.

One embodiment of this invention is directed to a pharmaceutical composition comprising at least one (e.g, one) compound of formula (1), or a pharmaceutically acceptable salt or solvate thereof, in combination with a pharmaceutically acceptable carrier.

The methods of treatment of this invention are advantageous in treating diseases where the ELR-CXC chemokine binds to CXCR1 and/or CXCR2.

Another embodiment of the invention is directed to a method of treating CXCR1 and/or CXCR2 chemokine mediated diseases in a patient in need of such treatment comprising administering to the patient a therapeutically effective amount of at least one compound (e.g., one) of formula (1), or a pharmaceutically acceptable salt or solvate thereof.

Another embodiment of the invention is directed to a method of treating CXCR1 and/or CXCR2 chemokine mediated diseases in a patient in need thereof comprises administering to the patient (a) an effective amount of at least one (e.g., one) compound of formula (1), or a pharmaceutically acceptable salt or solvate thereof, concurrently or sequentially with (b) at least one additional agent, drug, medicament, antibody and/or inhibitor useful for the treatment of CXCR1 and/or CXCR2 chemokine mediated diseases. Examples of the additional medicament, drug or agent include, but are not limited to disease modifying antirheumatic drugs; nonsteroidal anitinflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of the method of treating a CXCR1 and/or CXCR2 chemokine mediated disease is directed to administering (a) a therapeutically effective amount of at least one compound of formula (1), or a pharmaceutically acceptable salt or solvate thereof, concurrently or sequentially with (b) at least one (e.g., one) medicament selected from the group consisting of: disease modifying antirheumatic drugs; nonsteroidal anitinflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of this invention is directed to a method of treating cancer in a patient in need of such treatment, the method comprises administering to said patient a therapeutically effective amount of a compound of formula (1), or a pharmaceutically acceptable salt or solvate thereof.

Another embodiment of this invention is directed to a method of treating cancer comprising administering to the patient a therapeutic amount of at least one (e.g., one) compound of formula (1), or a pharmaceutically acceptable salt or solvate thereof, concurrently or sequentially with (a) at least one antineoplastic agent selected from the group consisting of: (1) gemcitabine, (2) paclitaxel (Taxol®), (3) 5-Fluorouracil (5-FU), (4) cyclo-phosphamide (Cytoxan®), (5) temozolomide and (6) Vincristine or (b) at least one (e.g., one) agent selected from the group consisting of (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

Another embodiment of this invention is directed to a method of inhibiting angiogenesis in a patient in need of such inhibition comprising administering to the patient an effective amount of at least one compound of formula (1), or a pharmaceutically acceptable salt or solvate thereof.

Another embodiment of this invention is directed to a method of treating an angiogenic ocular disease in a patient in need of such treatment the method comprising administering to said patient an effective amount of at least one (e.g., one) compound of formula (1), or a pharmaceutically acceptable salt or solvate thereof.

Another embodiment of this invention is directed to a method of treating asthma in a patient in need of such treatment the method comprising administering to the patient a therapeutically effective amount of at least one compound of formula (1), or a pharmaceutically acceptable salt or solvate thereof.

Another embodiment of this invention is directed to a method of treating a pulmonary disease disease (e.g., COPD, asthma, or cystic fibrosis), in a patient in need of such treatment the method comprising administering to the patient a therapeutically effective amount of: (a) at least one compound of formula (1), or a pharmaceutically acceptable salt or solvate thereof, concurrently or sequentially with (b) at least one (e.g., one) compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones.

Another embodiment of this invention is directed to method of treating multiple sclerosis in a patient in need of such treatment the method comprising administering to the patient:(a) a therapeutically effective amount of at least one (e.g., one) compound of formula (1), or a pharmaceutically acceptable salt or solvate thereof, concurrently or sequentially with (b) a therapeutically effective amount of at least one (e.g., one) compound selected from the group consisting of: glatiramer acetate, glucocorticoids, methotrexate, azothioprine, mitoxantrone, and CB2-selective inhibitors.

Another embodiment of this invention is directed to a method of treating multiple sclerosis in a patient in need of such treatment in accordance with the invention may also include the concurrent or sequential administration to a patient a therapeutically effective amount of: (a) at least one compound of formula (1), or a pharmaceutically acceptable salt or solvate thereof, and (b) at least one compound selected from the group consisting of: methotrexate, cyclosporin, leflunimide, sulfasalazine, β-methasone, β-interferon, glatiramer acetate, prednisone, etonercept, and infliximab.

Another embodiment of this invention is directed to a method of treating rheumatoid arthritis in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating rheumatoid arthritis in a patient in need of such treatment comprising administering to said patient a therapeutically effective amount of at least one (usually 1) compound of formula 1, or a pharmaceutically acceptable salt or solvate thereof, in combination with at least one compound selected from the group consisting of COX-2 inhibitors, COX-1 inhibitors, immunosuppressives (e.g., methotrexate, cyclosporin, leflunimide and sulfasalazine), steroids (e.g., betamethasone, cortisone and dexamethasone), PDE 4 inhibitors, anti-TNF-α compounds, MMP inhibitors, glucocorticoids, chemokine inhibitors, CB2-selective agents, and other classes of compounds indicated for the treatment of rheumatoid arthritis.

Another embodiment of this invention is directed to a method of treating stroke and ischemia reperfusion injury in a patient in need of such treatment the method comprising administering to the patient a therapeutically effective amount of: (a) at least one compound of formula (1), or a pharmaceutically acceptable salt or solvate thereof, concurrently or sequentially with (b) at least one compound selected from the group consisting of: thrombolitics (e.g., tenecteplase, TPA, alteplase), antiplatelet agents (e.g., gpllb/llla), antagonists (e.g., abciximab and eftiifbatide), anticoagulants (e.g., heparin), and other compounds indicated for the treatment of rheumatoid arthritis.

Another embodiment of this invention is directed to a method of treating stroke and ischemia reperfusion injury in a patient in need of such treatment the method comprising administering to the patient a therapeutically effective amount of: (a) at least one compound of formula (1), or a pharmaceutically acceptable salt or solvate thereof concurrently or sequentially with (b) at least one compound selected from the group consisting of: tenecteplase, TPA, alteplase, abciximab, eftiifbatide, and heparin.

Another embodiment of this invention is directed to a method of treating psoriasis in a patient in need of such treatment the method comprising administering to the patient a therapeutically effective amount of: a) at least one compound of formula (1), or a pharmaceutically acceptable salt or solvate thereof, concurrently or sequentially with (b) at least one compound selected from the group consisting of: immunosuppressives (e.g., methotrexate, cyclosporin, efalizumab, alefacept, leflunimide and sulfasalazine), steroids (e.g., β-methasone) and anti-TNF-α compounds (e.g., etonercept and infliximab).

This invention also provides a method of treating a CXCR1 and/or a CXCR2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritus, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one compound (usually 1) of formula 1, or a pharmaceutically acceptable salt or solvate thereof.

Another embodiment of this invention is directed to a method of treating diseases such as allograft rejections, early transplantation rejections, autoimmune deafness, myocarditis, neuropathies, autoimmune diseases and vasculitis syndromes wherein said
  (a) Allograft rejections are selected from the group consisting of acute allograft rejections and chronic allograft rejections,
  (b) Early transplantation rejection is an acute allograft rejection,
  (c) Autoimmune deafness is Meniere's disease,
  (d) Myocarditis is viral myocarditis,
  (e) Neuropathies are selected from the group consisting of IgA neuropathy, membranous neuropathy and idiopathic neuropathy,
  (f) Autoimmune diseases are anemias, and
  (g) Vasculitis syndromes are selected from the group consisting of giant cell arteritis, Behcet's disease and Wegener's granulomatosis.

Another embodiment of this invention is directed to a method of treating COPD in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating arthritis in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating osteoarthritis in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating pain in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating pain in a patient in need of such treatment comprising administering to said patient a therapeutically effective amount of at least one (usually one) compound of formula 1, or a pharmaceutically acceptable salt or solvate thereof, and administering a therapeutically effective amount of at least one medicament selected from the group consisting of: NSAIDs, COXIB inhibitors (e.g., COX-1 and COX-2 inhibitors), anti-depressants, and anti-convulsants.

Another embodiment of this invention is directed to a method of treating acute pain in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating acute inflammatory pain in a patient in need of such treatment comprising administering to said patient a therapeutically effective amount of at least one (usually one) compound of formula 1, or a pharmaceutically acceptable salt or solvate thereof.

Another embodiment of this invention is directed to a method of treating chronic inflammatory pain in a patient in need of such treatment comprising administering to said-patient a therapeutically effective amount of at least one (usually one) compound of formula 1, or a pharmaceutically acceptable salt or solvate thereof.

Another embodiment of this invention is directed to a method of treating neropathic pain in a patient in need of such treatment comprising administering to said patient a therapeutically effective amount of at least one (usually one) compound of formula 1, or a pharmaceutically acceptable salt or solvate thereof.

Another embodiment of this invention is directed to a pharmaceutical composition comprising at least one (e.g., 1-3, usually 1) compound of formula 1, or a pharmaceutically acceptable salt or solvate thereof, and at least one (e.g., 1-3, usually 1) other agent, medicament, antibody and/or inhibitor disclosed above, and a pharmaceutically acceptable carrier.

In general the compounds of this invention used to treat pain will have CXCR2 antagonistic activity.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COXIB inhibitors include but are not limited to: rofecoxib and celecoxib.

Anti-depressants are well known to those skilled in the art and can be used in their known dosages and dosage regimens. Examples of anti-depressants include but are not limited to: amitriptyline and nortriptyline.

Anti-convulsants are well known to those skilled in the art and can be used in their known dosages and dosage regimens. Examples of Anti-convulsants include but are not limited to: gabapentin, carbamazepine, pregabalin, and lamotragine.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md. which is incorporated herein by reference.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The tansdermal composition can take the form of creams, lotions, aerosols and/or emulsions and can be included in a transdermal patch of the matrix or reservoir type as are conventional in the art for this purpose.

The compound can be administered orally.

A suitable pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, or from about 0.01 mg to about 750 mg, or from about 0.01 mg to about 500 mg, or from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 2003 edition (Thompson PDR, Montvale, N.J. 07645-1742, USA); the disclosure of which is incorporated herein by reference thereto.

The amount and frequency of administration of the compounds of formula (1) and the chemotherapeutic agents and/or radiation therapy will be regulated according to the judgment of the attending clinician (physician) considering such factors as age, condition and size of the patient as well as severity of the disease being treated. A dosage regimen of the compound of formula (1) can be oral administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

If the compound of formula (1), and the chemotherapeutic agent and/or radiation are not administered simultaneously or essentially simultaneously, then the initial order of administration of the compound of formula (1), and the chemotherapeutic agent and/or radiation, may not be important. Thus, the compound of formula (1) may be administered first, followed by the administration of the chemotherapeutic agent and/or radiation; or the chemotherapeutic agent and/or radiation may be administered first, followed by the administration of the compound of formula (1). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound of formula (1) followed, where determined advantageous, by the administration of the chemotherapeutic agent and/or radiation, and so on until the treatment protocol is complete.

The particular choice of a compound of formula (1), and chemotherapeutic agent and/or radiation will depend upon the diagnosis of the attending physicians and their judgment of the condition of the patient and the appropriate treatment protocol.

Also, in general, the compound of formula (1) and the chemotherapeutic agent do not have to be administered in the same pharmaceutical composition, and may, because of different physical and chemical characteristics, have to be administered by different routes. For example, the compound of formula (1) may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent—i.e., the compound of formula (1), chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Compounds of formula (1) may be produced by processes known to those skilled in the art, in the following reaction schemes, and in the preparations and examples below.

Alternatively, the amine

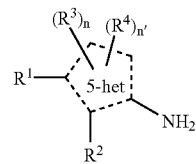

can be converted to the corresponding isocyanate

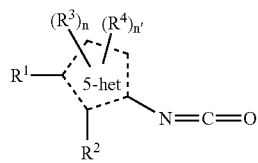

using procedures well known in the art. The coupling of this isocyanate and the amine Y—NH$_2$ can afford the compound of formula (1).

Scheme - 1

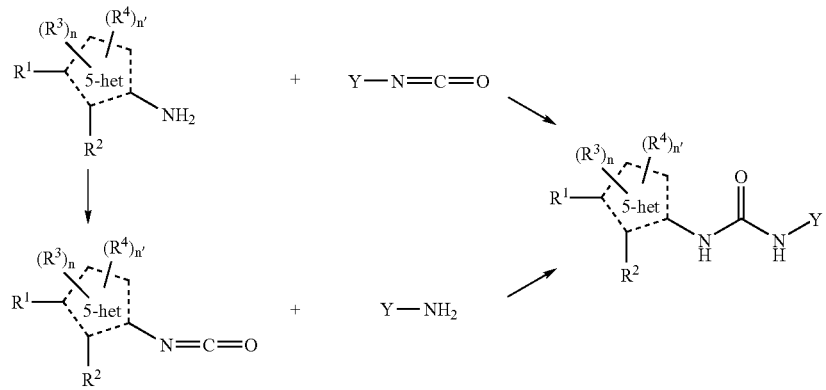

All substituents are as defined for formula (1).

Urea-type compounds of formula (1) can be prepared from the condensation of

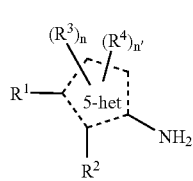

and isocyanate Y—N═C═O. The amine and the isocyanate are commercially available, or can be prepared according to the procedures described herein or can be prepared by procedures well known in the art (e.g., *Org. Syn.* Vol. 78, 220).

Scheme - 2

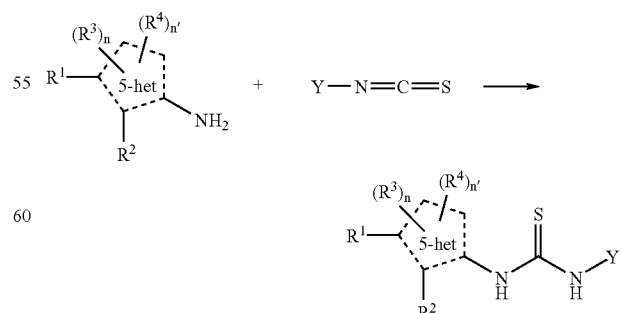

All substituents are as defined in formula (1)

Thiourea-type compounds of formula (1) (i.e., compounds of formula 1 wherein Q is =C=S) can be prepared from the condensation of the amine

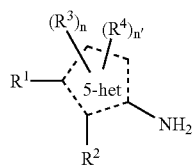

and the thioisocyanate Y—N=C=S using procedures well known in the art. The amine and the thioisocyante are commercially available, or can be prepared using the procedures described below, or can be prepared using techniques well know in the art.

Guanidine-type compounds of formula (1) (i.e., compounds of formula (1) wherein Q is =C=N—CN) can be prepared from the corresponding thiourea compound (wherein the thiourea compound can be obtained, for example, by following the procedures of Scheme 2) following the procedures of Scheme 3 and following procedures well known in the art. Procedures well known in the art can be used to provide functional group protection of the thiourea starting reactant, and to deprotect the desired product.

Scheme - 4

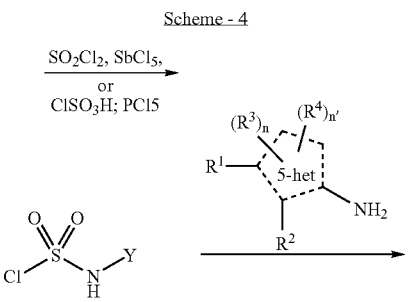

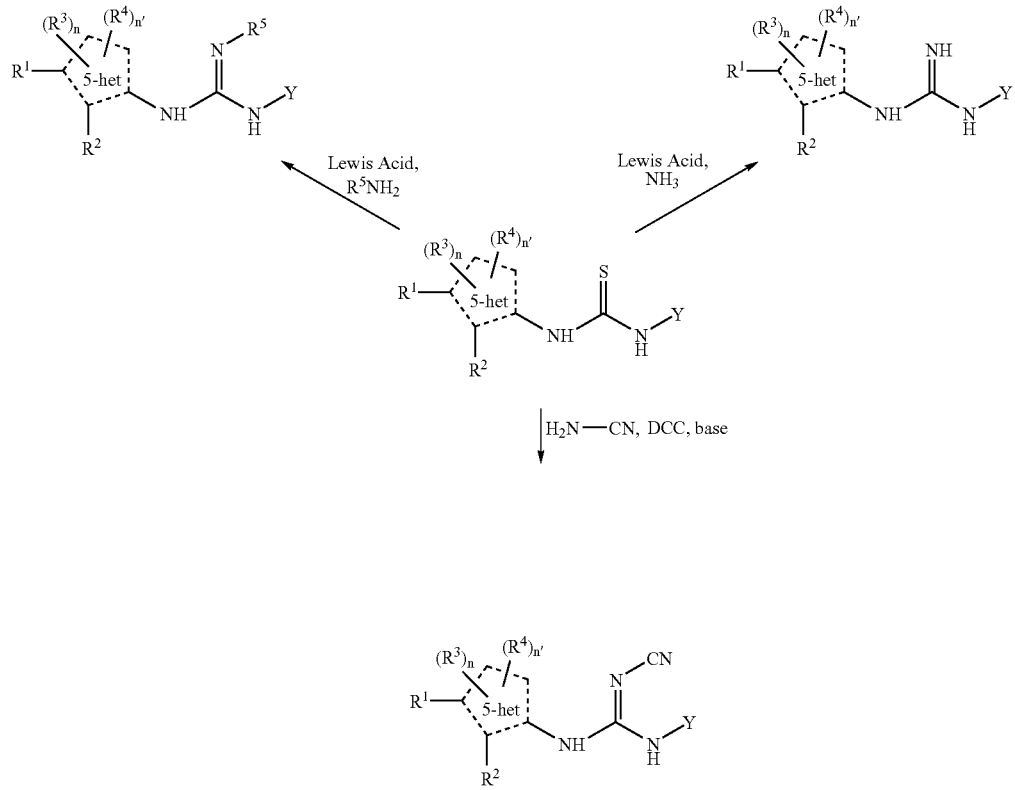

Scheme - 3

All substituents are as defined in formula (1)

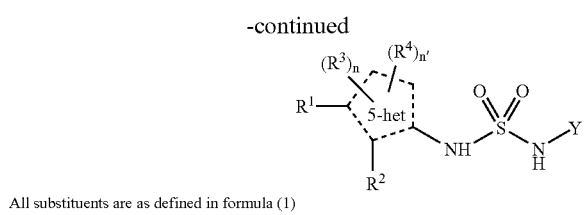

All substituents are as defined in formula (1)

The procedures of Scheme 4 can be followed to prepare the sulfamide-type compounds of formula (1) (i.e., compounds of formula (1) wherein Q is $=SO_2$), by converting the amine Y—$NH_2$ to the intermediate sulfamoyl chloride Y—$NHSO_2Cl$, and then coupling the sulfamoyl chloride with the amine 5-het-$NH_2$. The amine Y—$NH_2$ and the amine 5-het-$NH_2$ are commercially available, or can be prepared by procedures well known in the art, or can be prepared by the procedures described below.

The invention disclosed herein is exemplified by the following preparations and examples that should not be construed to limit the scope of the disclosure. Alternative mechanistic pathways and analogous structures may be apparent to those skilled in the art.

PREPARATIVE EXAMPLE 1

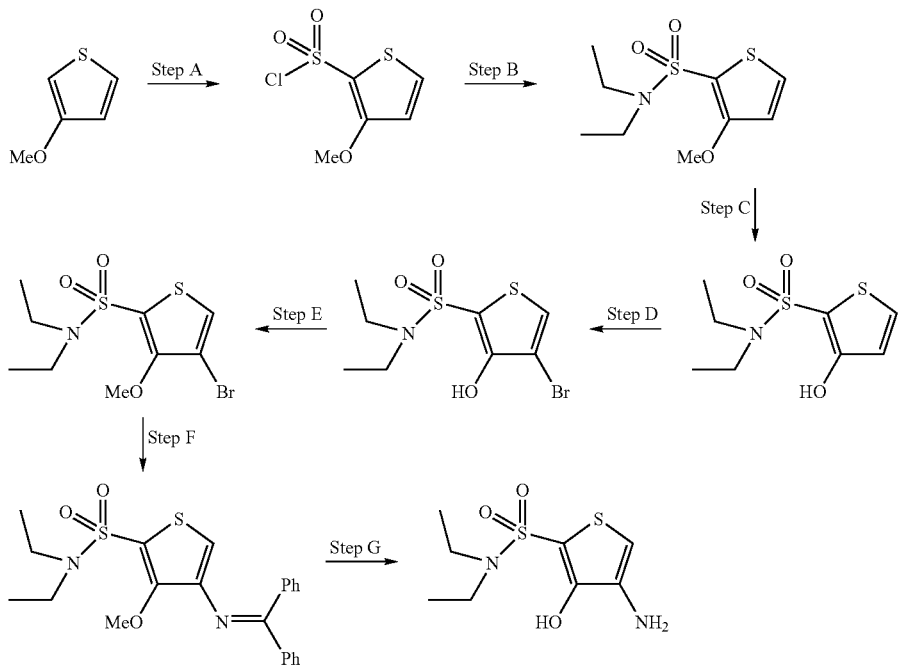

Step A

To a stirred 300 mL $CH_2Cl_2$ solution in a $-78°$ C. cooling bath was added chlorosulfonic acid (14.5 mL, 217.8 mmol). A solution of 3-methoxythiophene (10.0 g, 87.59 mmol) in 80 mL of $CH_2Cl_2$ was added slowly along the side wall of the flask. After 30 min, the cooling bath was removed. Reaction was continued at room temperature for 2 h. Stirring was stopped, the mixture was set still for approximately 10 min, and filtered directly and carefully through a 2-in silica gel pad. The green glue residue was extracted several times with $CH_2Cl_2$ and filtered. The filtrate was concentrated under reduced pressure to afford 10.75 g (58%) of thiophene-sulfonyl chloride as an off-white (trace green-grey) solid.

Step B

To a solution of thiophene-sulfonyl chloride (10.12 g, 47.58 mmol), obtained from step A, in 250 mL of $CH_2Cl_2$ at room temperature was added triethylamine (13.3 mL, 95.42 mmol) followed by diethyl amine (6.2 mL, 59.85 mmol). The mixture was stirred for 2 h, washed with $H_2O$ (50 mL), a 1.0 M HCl aqueous solution (50 mL×2), $H_2O$ (50 mL), and brine. The organic solution was dried with $Na_2SO_4$, and concentrated in vacuo to afford 11.54 g (97%) of diethyl-sulfonamide as a light wheat color solid ($MH^+=250.0$).

Step C

To a stirred solution of diethylsulfonamide (11.54 g, 46.28 mmol), available from step B above, in 230 mL of $CH_2Cl_2$ at $-78°$ C. was added dropwise along the sidewall of the flask a 1.0 M solution of boron tribromide in $CH_2Cl_2$ (58 mL, 58.0 mmol) The resulting mixture was stirred over night while temperature of the cooling bath was increased slowly from $-78°$ C. to $10°$ C. $H_2O$ (150 mL) was added. The mixture was separated. The aqueous layer was extracted with $CH_2Cl_2$ (150 mL); and the combined organic layers were washed with brine (100 mL), dried with $Na_2SO_4$, filtered, and concentrated in vacuo to give 11.16 g (crude, 100%) of the corresponding hydroxyl-thiophene as a dark brown oil ($MH^+=236.0$).

Step D

Hydroxy-thiophene (11.16 g,~46.27 mmol), from step C above, was dissolved in 230 mL of $CH_2Cl_2$, and added with potassium carbonate(16.0 g, 116.0 mmol) at room temperature. Bromine (4.75 mL, 92.7 mmol) was added drop wise. After stirred for 18 h, the solution was decanted. The solid residue was extracted with CH$_2$Cl$_2$ (100 mL). The organic fractions were combined, washed with H$_2$O (100 mL×2) and a 10% Na$_2$S$_2$O$_3$ aqueous solution (100 mL×2). The Na$_2$S$_2$O$_3$ washings were acidified to pH ~4 using a 1.0 M HCl aqueous solution, and extracted with CH$_2$Cl$_2$ (100 mL×2). All organic layers were combined, washed with brine, dried by Na$_2$SO$_4$, filtered, and concentrated in vacuo to yield 16.8 g (crude, 100%) of hydroxyl-thiophene bromide as a dark brown oil.

Step E

Hydroxyl-thiophene bromide (16.8 g, crude,~46.27 mmol), from step D above, was dissolved in 250 ml of acetone, and added with potassium carbonate (32.0 g, 232.0 mmol) followed by iodomethane (28 mL, 450 mmol). The resulting mixture was refluxed over night. After cooled to room temperature, 200 mL of CH$_2$Cl$_2$ was added, the mixture was filtered through a 1-in silica gel pad, rinsing with CH$_2$Cl$_2$. The filtrate was concentrated under reduced pressure to a dark brown oil, which was purified by flash column chromatography, eluting with hexanes, hexanes-CH$_2$Cl$_2$ (3:1, 2:1, v/v). Removal of solvents afforded 7.56 g (50%) of methoxy-thiophene bromide as a light yellow oil (M$^+$=328, M+2=330).

Step F

An oven dried two-neck round bottom flask was equipped with a magnetic stirring bar, a condenser, a stopcock, and cooled under nitrogen. Solid palladium acetate, rac-BINAP, and cesium carbonate were added. The solid mixture was degassed via house vacuum, refilled with nitrogen. This process was repeated two more times. A solution of thiophene-bromide (5.5 g, 16.8 mmol, from step E) in 100 mL of toluene was added, followed by benzophenone imine. The mixture was stirred and heated at reflux for 3.5 d. After cooled to room temperature, the mixture was diluted with ether (150 mL), filtered through a Celite pad. The filtrate was concentrated in vacuo to a dark brown oil, which was purified by flash column chromatography, eluting with hexanes, hexanes-CH$_2$Cl$_2$ (2:1, 1:1, 1:2, v/v), and CH$_2$Cl$_2$. Removal of solvents afforded 6.4 g (89%) of thiophene-imine as a dark yellow oil (MH$^+$=429.1).

Step G

To a solution of thiophene imine (6.0 g, 13.9 mmol, from Step F above) in 100 mL of CH$_2$Cl$_2$ at −78° C. was added dropwise a 1.0 M solution of boron tribromide in CH$_2$Cl$_2$ (17.2 mL, 17.2 mmol). The mixture was stirred for 4 h while temperature of the cooling bath was increased to 10° C. Cooling bath was removed, and reaction was continued for 45 min. H$_2$O (100 mL) was added. The two layers were separated after 10 min, the aqueous layer was extracted with CH$_2$Cl$_2$ (50 mL×2), and the combined organic layers were washed with brine. The organic solution was concentrated in vacuo to give a dark reddish brown oil which was used next. The aqueous layers were adjusted to pH~6 using a sat. NaHCO$_3$ aqueous solution, and extracted with CH$_2$Cl$_2$ (100 mL×2). The extracts were washed with brine, dried by Na$_2$SO$_4$, and filtered through a 0.5-in silica gel pad. The filtrate was concentrated to yield the first batch of the hydroxyl-amine product (0.27 g).

The brown oil from above was dissolved in 75 mL of methanol, and added with sodium acetate (2.7 g, 32.91 mmol) and hydroxyl amine hydrochloride (1.72 g, 24.75 mmol). The mixture was stirred at room temperature for.2.5 h, quenched with a 1.0 M NaOH aqueous solution (50 mL). The aqueous mixture was washed with ether (100 mL×3). The combined ether extracts were re-extracted with 25 mL of the 1.0 M NaOH aqueous solution. The basic aqueous layers were combined, adjusted to pH~6.0 using a 3.0 M HCl aqueous solution, and extracted with CH$_2$Cl$_2$ (100 mL×4). The organic extracts were washed with brine, dried by Na$_2$SO$_4$, and filtered through a 0.5-in silica gel pad, rinsing with CH$_2$Cl$_2$. The filtrate was concentrated in vacuo to afford 2.55 g of the hydroxyl-amine product as the second batch (total 2.82 g, 82%, MH$^+$=251.0).

PREPARATIVE EXAMPLES 2.1-2.5

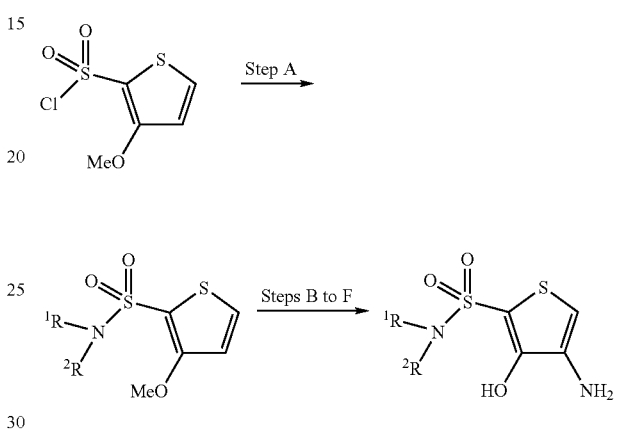

Step A

Following the procedure described in Preparative Example 1, step B, but using the amines indicated in the table below, the corresponding thiophene-sulfonamides were obtained.

Steps B to F

Following the procedures set forth in Preparative Example 1, steps C through G, and using the thiophene-sulfonamides available in Step A above, hydroxyl-thiophene-amines in Table 1 were prepared.

TABLE 1

| Prep Ex. | R$^1$R$^2$NH | Hydroxy-thiophene-amine | Yield (MH$^+$) |
|---|---|---|---|
| 2.1 | MeMeNH | ![structure] | 27% 223.0 |
| 2.2 | MeEtNH | ![structure] | 17% 237.0 |

TABLE 1-continued

| Prep Ex. | R¹R²NH | Hydroxy-thiophene-amine | Yield (MH⁺) |
|---|---|---|---|
| 2.3 | BnBnNH | ![structure] Bn-N(Bn)-SO2-thiophene(OH)(NH2) | 15% 375.1 |
| 2.4 | EtBnNH | ![structure] Et-N(Bn)-SO2-thiophene(OH)(NH2) | 23% 313.0 |
| 2.5 | iPrBnNH | ![structure] iPr-N(Bn)-SO2-thiophene(OH)(NH2) | 4% 327 |

PREPARATIVE EXAMPLE 3

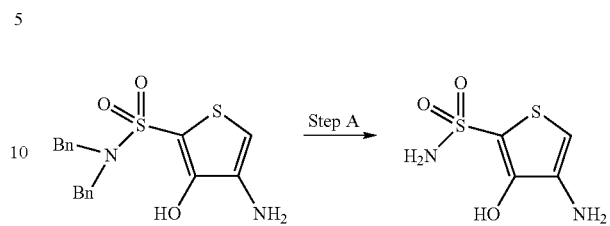

Step A

Dibenzylsulfonamide-thiophene-amine (660 mg, 1.76 mmol), available from Preparative Example 2.3, was stirred with 4 mL of concentrated sulfuric acid at room temperature for 5 h. Ice water (50 mL) was added. The aqueous mixture was adjusted to pH~5 using a 1.0 M NaOH aqueous solution, and extracted with ethyl acetate (200 mL×4). The organic extracts were washed with $H_2O$ and brine, dried over $MgSO_4$, filtered, and concentrated in vacuo to yield 237 mg of the desired sulfonamide amine (69%, MH⁺=194.23, $[M-NH_2]^+$=178).

PREPARATIVE EXAMPLE 3.1-3.2

Following the procedures set forth in Preparative Example 3, thiophene-amines listed in Table 2 below were prepared by using the precursors specified.

TABLE 2

| Prep Ex. | Precursor (prep. ex.) | Hydroxy-thiophene-amine | Yield (MH⁺) |
|---|---|---|---|
| 3.1 | Et-N(Bn)-SO2-thiophene(OH)(NH2) (2.4) | Et-NH-SO2-thiophene(OH)(NH2) | 69% 223.0 |
| 3.2 | iPr-N(Bn)-SO2-thiophene(OH)(NH2) (2.5) | iPr-NH-SO2-thiophene(OH)(NH2) | 78% 237.0 |

PREPARATIVE EXAMPLE 4

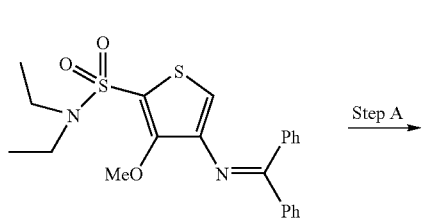

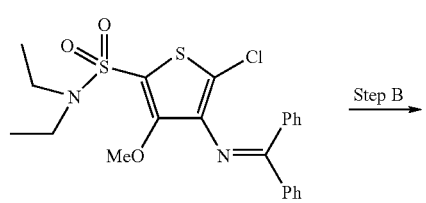

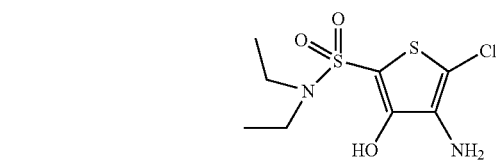

Step A

Thiophene-imine (1.5 g, 3.5 mmol), prepared in Step F of Preparative Example 1, was dissolved in 30 mL of $CH_2Cl_2$. Pyridine (0.85 mL, 10.4 mmol) was added followed by solid N-chloro-succinamide (0.94 g, 7.04 mmol). After stirred for 48 h, the mixture was diluted with $CH_2Cl_2$ (50 mL), washed with $H_2O$ (30 mL) and brine (30 mL). The organic solution was dried with $Na_2SO_4$, and evaporated under reduced pressure to a dark brown oil, which was separated by preparative TLC ($CH_2Cl_2$ as eluent) to afford 0.66 g (41%) of chloro-imine as a dark reddish yellow oil ($MH^+$=463.1).

Step B

Following the procedure described in Step G of Preparative Example 1, chloro-imine (0.61 g, 1.3 mmol) obtained in Step A above was converted to the desired hydroxy-thiophene amine (0.34 g, 92%, $MH^+$=285.1).

PREPARATIVE EXAMPLE 4.1

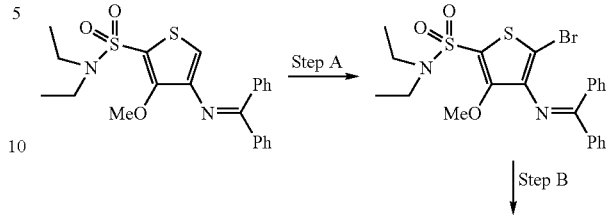

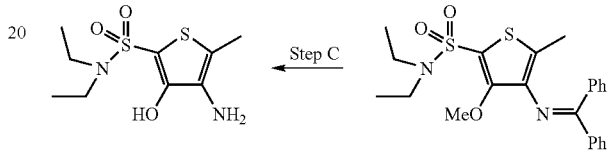

Step A

Thiophene-imine (1.5 g, 3.5 mmol), available from Step F of Preparative Example 1, was dissolved in 30 mL of $CH_2Cl_2$, and added with potassium carbonate (1.2 g, 8.70 mmol) followed by drop wise addition of bromine (0.32 mL, 6.25 mmol). After stirred for 2 d, $H_2O$ was added. The two layers were separated. The aqueous layer was extracted with $CH_2Cl_2$ (50 mL×2). The organic layers were combined, washed with a 10% $Na_2S_2O_3$ aqueous solution (40 mL×2) and brine (40 mL), dried over $Na_2SO_4$, and concentrated in vacuo to a dark brown oil. This oil was separated by preparative TLC ($CH_2Cl_2$ as eluent), to give 0.96 g (54%) of the desired bromo-imine as a bright yellow oil ($M^+$=507, M+2=509)

Step B

Bromo-imine (0.95 g, 1.87 mmol), available from Step A above, was dissolved in 15 mL of anhydrous THF, cooled in a −78° C. bath, and treated with a 2.5 M solution of n-butyl lithium in hexanes (1.2 mL, 3.0 mmol) drop wise along the side wall of the flask. After 30 min, Iodomethane (0.35 mL, 5.62 mmol) was added drop wise. Reaction was continued for 5 h, during which time the cooling bath was allowed to warm slowly to 0° C. The mixture was quenched by $H_2O$ (25 mL), and extracted with $CH_2Cl_2$ (50 mL×2). The organic extracts were washed with brine, dried with $Na_2SO_4$, and concentrated in vacuo to give 0.93 g (crude, >100%) of the desired methylated imine as a dark yellow oil ($MH^+$=443.1)

Step C

The crude methyl-imine (0.93 g), prepared in step B above, was converted to the methyl-hydroxyl-amine (0.21 g, 41%, $MH^+$=265.0) by using the procedures described in Step G of Preparative Example 1.

PREPARATIVE EXAMPLE 5

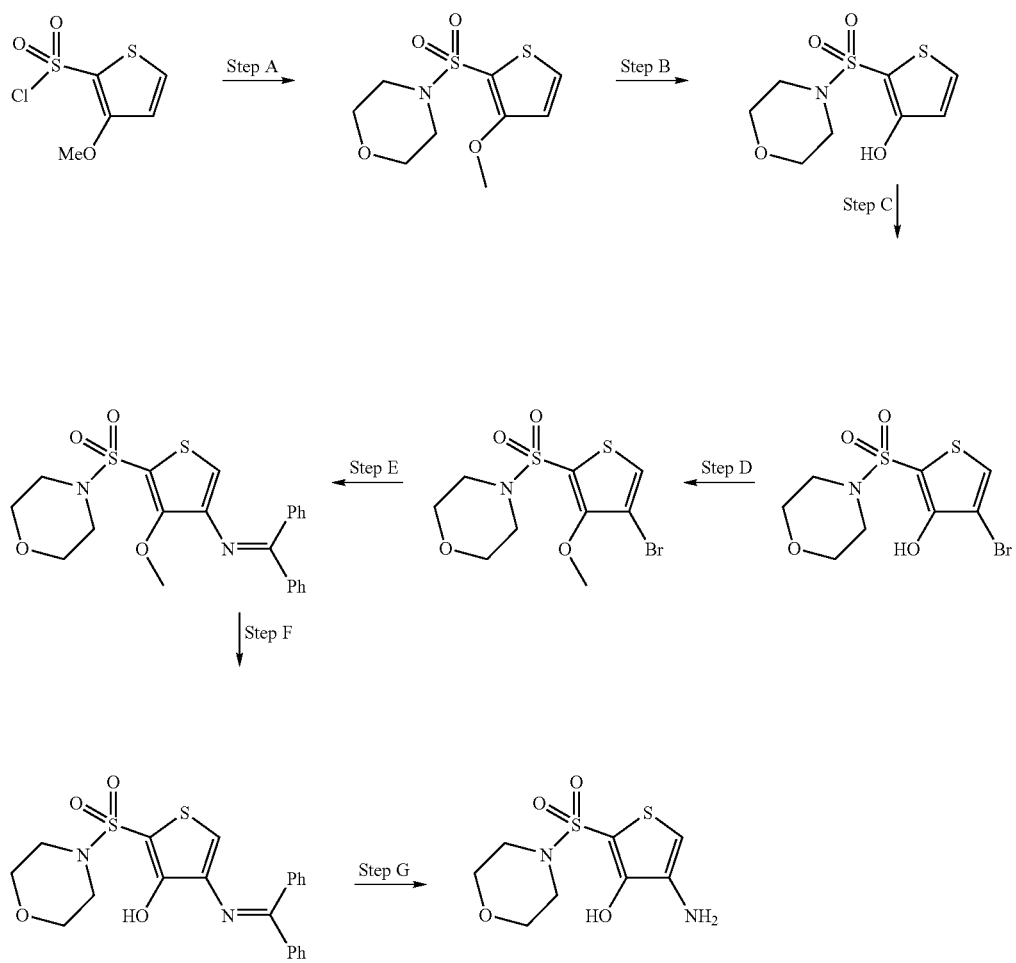

Step A Following the procedure described in Preparative Example 1, Step B, but using morpholine (4.0 g, 18.81 mmol), the desired morpholino-sulfonamide was obtained (4.84 g, 98%).

Step B

To a suspension of sodium hydride (1.4 g, 95%, 55.42 mmol) in 50 mL of N,N'-dimethylformamide (DMF) was added dropwise ethanethiol. The suspension turned to a clear solution, and was added to a stirred solution of morpholino-sulfonamide (4.84 g, 18.38 mmol), available from Step A above, in 15 mL of DMF. The resulting mixture was heated at 95° C. for 4.5 h. Upon aqueous work-up, the demethylated product was obtained (4.07 g, 89%).

Step C, D, and E

Following the procedures set forth in Preparative Example 1, Steps D, E and F, the hydroxyl-thiophene-sulfonamide (4.07 g, 16.33 mmol) available from Step B above was converted to the corresponding methoxy-thiophene-imine (3.75 g, 69%).

Step F

Applying the procedure used in Step B above, methoxy-thiophene-imine (2.75 g, 6.17 mmol) was demethylated to give the hydroxyl-thiophene-imine (2.42 g, 92%).

Step G

Following the procedure described in Preparative Example 1 Step G, hydroxyl-thiophene-imine prepared in Step F above (2.42 g, 5.65 mmol) was treated with sodium acetate and hydroxylamine hydrochloride in methanol at room temperature to afford the titled hydroxyl-amino-thiophene sulfonamide (1.06 g, 71%, MH$^+$=265.0).

PREPARATIVE EXAMPLE 5.1

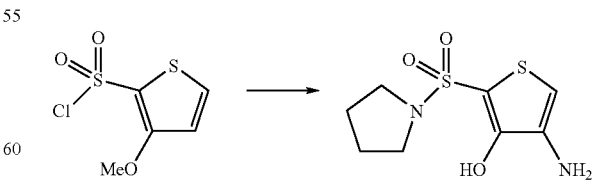

Following the procedures set forth in Preparative Example 5, except using pyrrolidine in place of morpholine, the titled hydroxyl-amino-thiophene sulfonamide was obtained (MH$^+$=249).

PREPARATIVE EXAMPLE 6

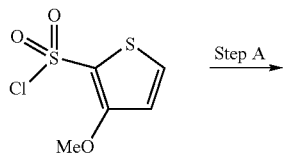

Step A

3-Methoxy-2-thiophenesulfonylchloride, available from Step A of Preparative Example 1, could be converted to methyl-3-methoxy-2-sulfone under the conditions of sodium O,O-diethylphosphorotellurite, triethylbenzylammonium chloride (cat.), and iodomethane in refluxing THF, according to the procedures described in *Synthetic Communications,* 1990, 20, 2291-2295.

Step B to F

Following the procedures set forth in Preparative Example 1, steps C through G, methyl-3-methoxy-2-thiophenesulfone obtained from Step A above, could be transformed into the desired hydroxyl-amine thiophenesulfone.

PREPARATIVE EXAMPLE 7

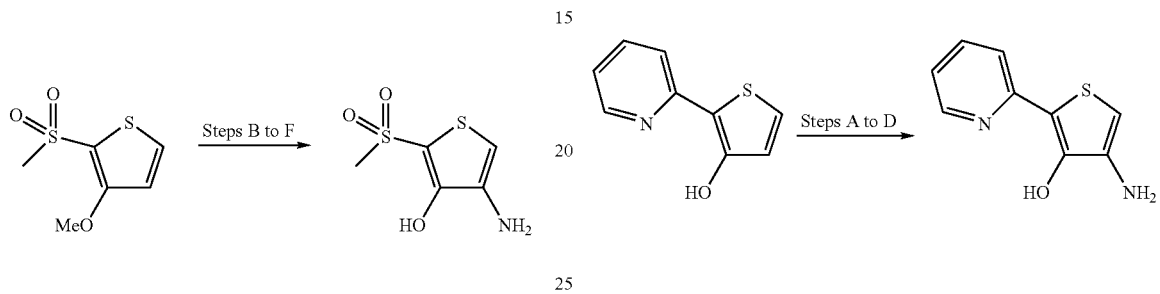

Step A to D

Hydroxy-pyridyl thiophene, prepared according to literature precedence (*Acta Chemica Scandinavica,* 1992, 46, 654-660), could be converted to the desired pyrdyl-hydroxyl-amine following the procedures set forth in Preparative Example 1, steps D through G.

PREPARATIVE EXAMPLE 8

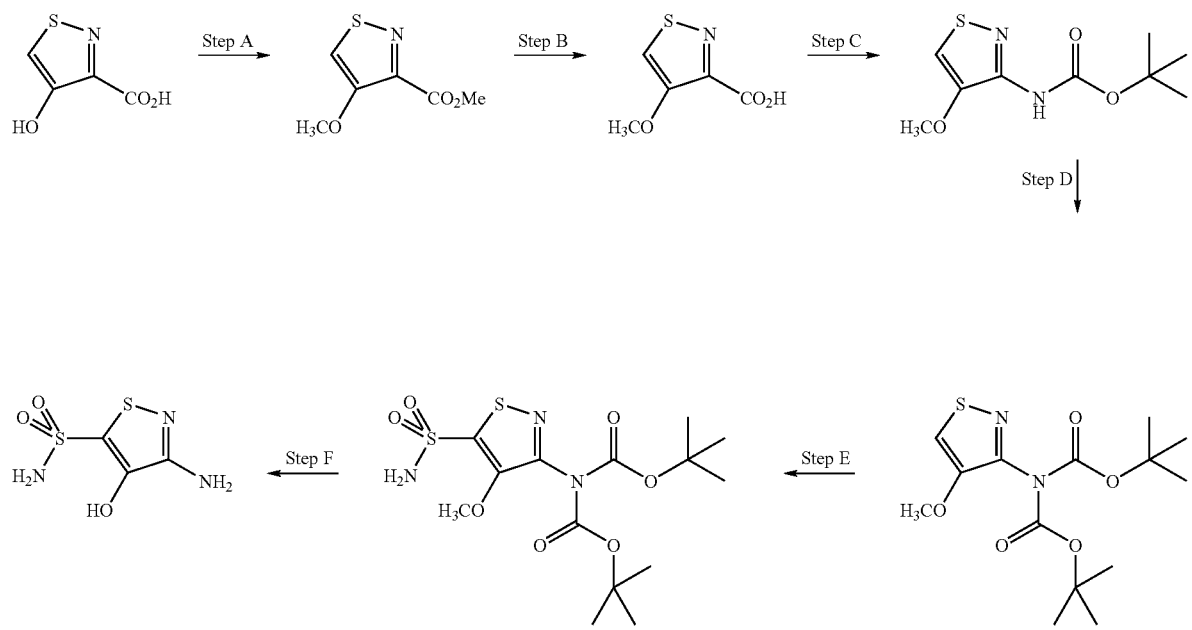

Step A

If one were to use a similar methylation procedure to that used in Preparative Example 1 step E, except using the hydroxyl acid from Bioorg. Med. Chem. Lett. 1996, 6, 1043, one would obtain the desired methoxy methyl ester.

Step B

The methoxy methyl ester, available from Step A above, could be hydrolyzed upon treatment of a 1.0 M NaOH aqueous solution at room temperature to afford the corresponding acid.

Step C

Following a similar procedure to that used in *Tetra. Lett.*, 1999, 40, 1721-1724, the acid from Step B above could be transformed into the corresponding t-butyl carbamate via Curtius rearrangement under the conditions of diphenylphosphoryl azide and triethylamine in refluxing toluene, and then t-butyl alcohol.

Step D

If mono-tert-butyl carbamate obtained in Step C above were treated with di-tertbutyidicarbonate and a suitable amine base, it would be converted to bis-tert-butyl carbamate.

Step E

Following a similar procedure to that used in *Synthesis*, 1986, 1031, except using the product from Step D above, one would obtain the desired sulfonamide compound.

Step F

Treatment of the product from Step E above with boron tribromide, and then trifluoroacetic acid in dichloromethane, the desired hydroxyl-amino-sulfonamide would be obtained.

PREPARATIVE EXAMPLE 9

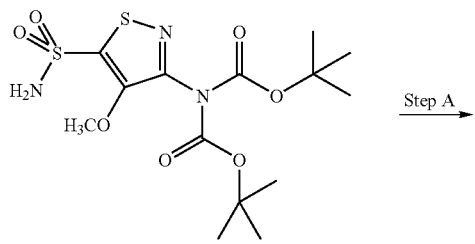

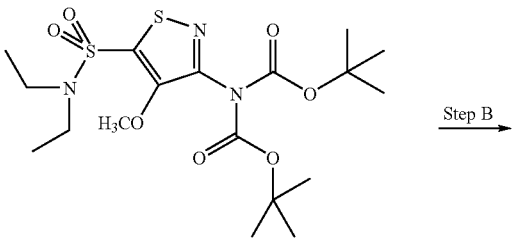

-continued

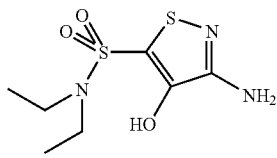

Step A

If the product from Step E of Preparative Example 8 were treated with iodoethane, potassium carbonate in refluxing acetone, the corresponding diethyl sulfonamide could be obtained.

Step B

The product from Step A above could be demethylated following the procedure described in Step C, Preparative Example 1. Further treatment of the demethylated intermediate with trifluoroacetic acid in dichloromethane should lead to the desired hydroxyl-amine product.

PREPARATIVE EXAMPLE 10

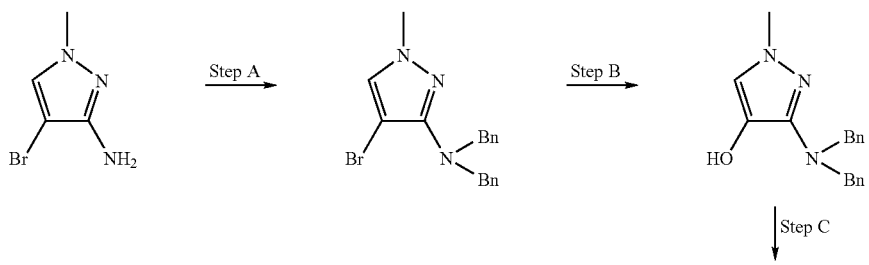

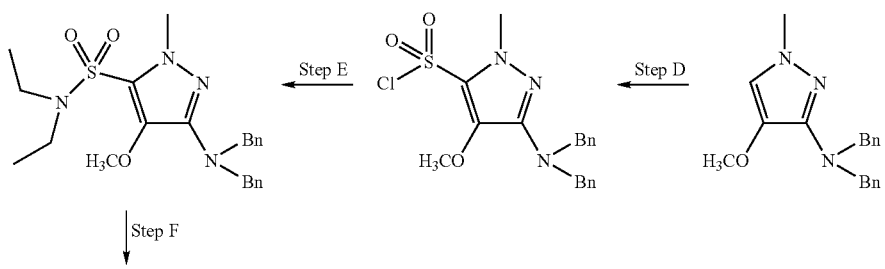

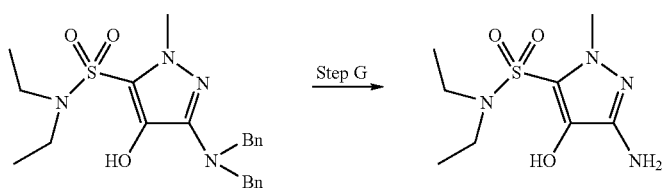

Step A

1-Methyl-4-bromo-3-aminopyrazole (commercially available) could be converted to the corresponding N,N-dibenzylaminopyrazole upon treatement with sodium hydride and benzyl bromide in N,N-dimethylformamide.

Step B

Following a similar procedure to that used in *Acta Chemica Scandinavica,* 1992, 46, 654-660, except using the product from Step A above, one would obtain the desired hydroxyl-pyrazole compound.

Step C

Following the procedure described in Step E, Preparative Example 1, except using the product from Step B above, the methylated pyrazole compound could be prepared.

Step D

Following the procedure described in Step A, Preparative Example 1, except using the product from Step C above, the desired pyrazole sulfonyl chloride could be generated.

Step E

Following the procedure described in Step B, Preparative Example 1, except using the product from Step D above, pyrazole diethylsulfonamide would be obtained.

Step F

Following the procedure described in Step C, Preparative Example 1, except using the product from Step E above, hydroxyl-pyrazole sulfonamide would be obtained.

Step G

If the product from Step F above were to be treated with 10% Palladium on carbon (cat.) in ethanol under a hydrogen atmosphere, hydroxyl-amino-pyrazole sulfonamide would be formed.

PREPARATIVE EXAMPLE 11

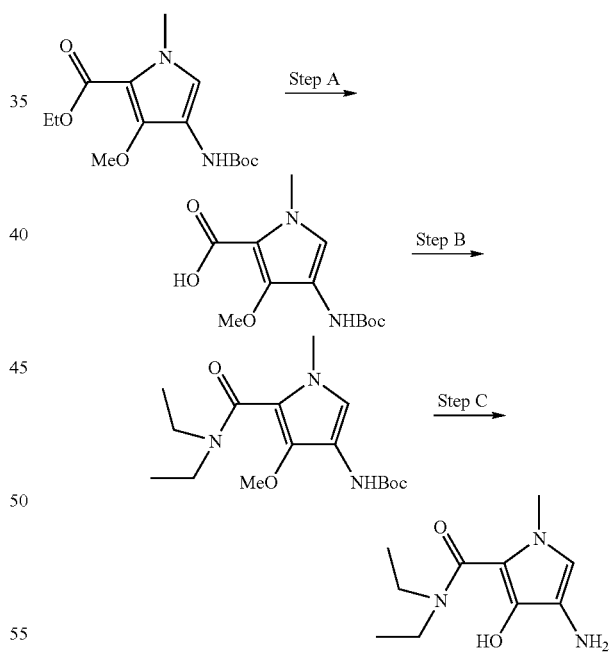

Step A

Ethyl-pyrrole-carboxylate, prepared according to known procedures described in *Synthesis,* 2000, 5, 673, could be hydrolyzed to the acid in THF upon treatment of a 1.0 M NaOH aqueous solution.

Step B

If one were to treat the acid, available from Step A above, with oxalyl chloride along with a catalytic amount of N,N'-dimethylformamide in dichloromethane at room temperature, followed 30 minutes later by solid potassium carbonate and diethyl-amine, the desired diethyl-amido-pyrrole could be obtained.

Step C

Following the procedure described in Step B, Preparative Example 9, except using the product from Step B above, the desired hydroxyl-amino-pyrrole compound would be prepared.

PREPARATIVE EXAMPLE 12

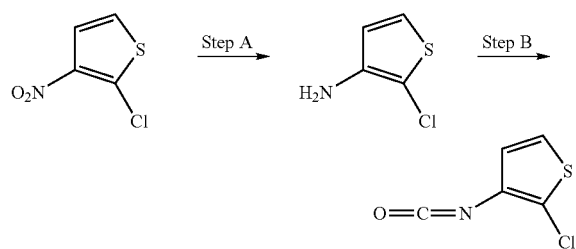

Step A

Following a similar procedure to that used in *Heterocycles* 1995, 41, 709-720, 2-chloro-3-nitrothiophene would be reduced to 2-chloro-3-aminothiophene under the conditions of FeSO$_4$.7H$_2$O in water and ethanol.

Step B

Following a similar procedure to that used in *Org. Syn.* Vol. 78, p. 220, 2-Chloro-3-amino-thiophene from Step A above could be converted to the desired isocyanate upon treatment with triphosgene in a mixture of dichloromethane and saturated sodium bicarbonate aqueous solution.

PREPARATIVE EXAMPLE 13

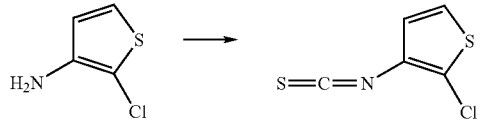

If 2-chloro-3-amino thiophene, from Step A of Preparative Example 12, were treated with thiocarbonyl dichloride, similar to the conditions and procedures used in *Chem. Pharm. Bull.* 1996, 44, 2042-2050, 2-chloro-3-thiophene-isothiocyanate would be obtained.

PREPARATIVE EXAMPLE 14

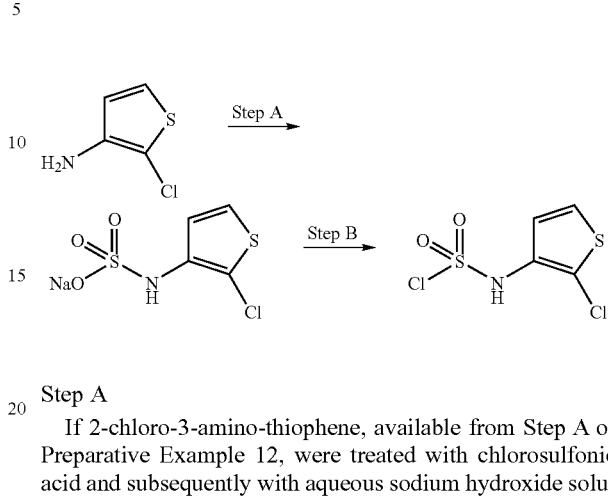

Step A

If 2-chloro-3-amino-thiophene, available from Step A of Preparative Example 12, were treated with chlorosulfonic acid and subsequently with aqueous sodium hydroxide solution in the manner as described in *J. Org. Chem.*, 1968, 33, 1295-1296, the corresponding sodium thiophene sulfamate would be generated.

Step B

If sodium thiophene sulfamate from step A above were treated with phosphorous pentachloride in refluxing benzene, similar to that used in *J. Org. Chem.*, 1976, 41, 4028-4029, the desired thiophenesulfamoyl chloride would be obtained.

PREPARATIVE EXAMPLE 15

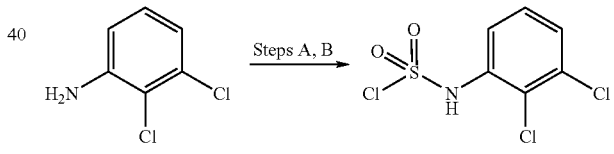

Following the procedures used in Preparative Example 14, steps A and B, 2,3-dichloroaniline could be converted to the corresponding sulfamoyl chloride.

PREPARATIVE EXAMPLE 16

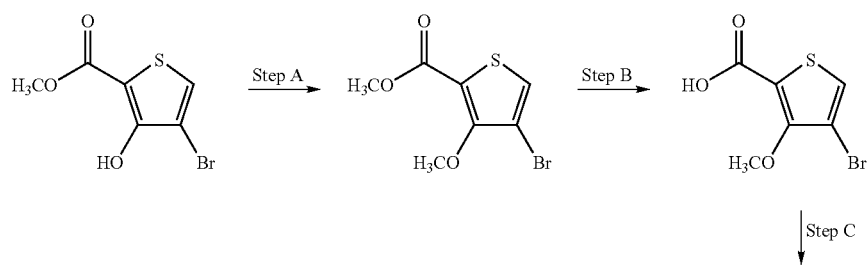

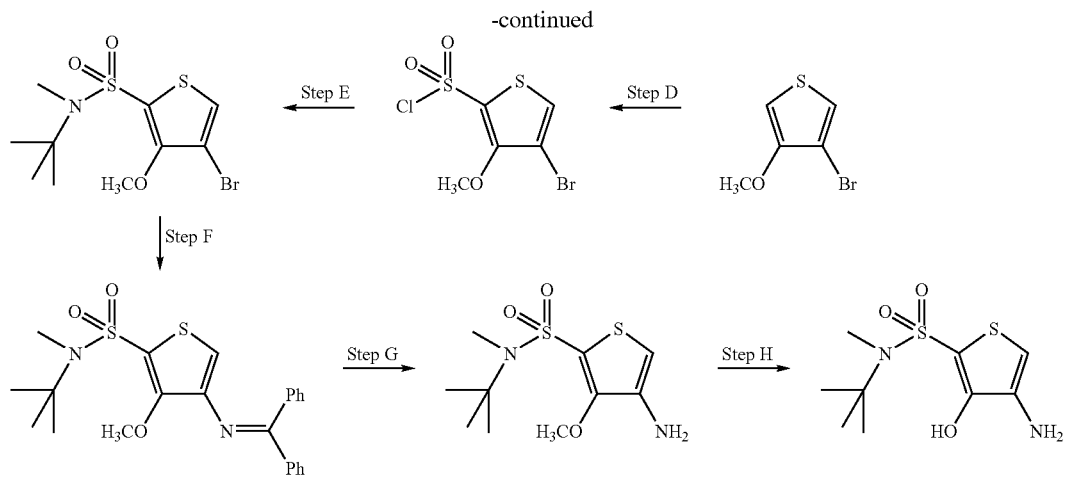

Step A

Methyl-4-bromo-3-hydroxy-2-thiophenecarboxylate (20 g, 84.36 mmol) was dissolved in 400 mL of acetone. Potassium carbonate (58 g, 420.3 mmol) was added followed by iodomethane (45 mL, 424 mmol). The resulting mixture was heated at reflux for 4.5 h. After cooling, the mixture was filtered through a thin Celite pad, rinsing with methylene chloride. The filtrate was concentrated in vacuo to give 22.5 g of methyl-4-bromo-3-methoxy-2-thiophenecarboxylate (crude, 100%, $MH^+=251.0$) as a dark green solid.

Step B

The product from Step A above (22.5 g, 84.36 mmol) was dissolved in 60 mL of tetrahydrofuran and added with 125 mL of a 1.0 M NaOH aqueous solution. The mixture was stirred at room temperature for 4 d, then washed with ether (60 mL×2), acidified to pH~2 using a 1.0 M HCl aqueous solution. Solids were precipitated out after acidification, and collected by filtration. The solid was dissolved in methylene chloride-ethyl acetate (~4:1, v/v). The organic solution was washed with $H_2O$ and brine, dried with $Na_2SO_4$, and concentrated in vacuo to a light yellow solid, further dried on hight vacuum, yielding 17.95 g of 4-bromo-3-methoxy-2-thiophene carboxylic acid (90%, $MH^+=237.0$).

Step C

The carboxylic acid (3.26 g, 13.75 mmol) available from Step B above was treated with 30 mL of concentrated sulfuric acid. The mixture was sealed in a one-neck round bottom flask, and heated at 65° C. for 4.5 h. After cooled to room temperature, the mixture was poured into 200 mL of crushed ice, and extracted with methylene chloride (100 mL×3). The organic extracts were combined, washed successively with $H_2O$ (50 mL×2), sat. $NaHCO_3$ (50 mL×3), and brine (50 mL). The organic solution was dried with $Na_2SO_4$, and concentrated in vacuo to a dark brown oil, which was purified by flash column chromatography (biotage, $SiO_2$ column) using hexanes-methylene chloride (3:1, v/v) as eluents. Removal of solvents afforded 1.83 g of 3-bromo-4-methoxy thiophene (69%) as a light yellow oil.

Step D

To a stirred solution of 3-bromo-4-methoxythiophene (550 mg, 2.85 mmol), prepared in Step C above, in 30 mL of methylene chloride at −78° C. was added dropwise along the inside wall of the flask chlorosulfonic acid (0.48 mL, 7.21 mmol). The mixture was stirred at −78° C. for 10 min, continued at room temperature for 1 h, and filtered through a 1-in silica gel pad, rinsing with methylene chloride. The filtrate was concentrated in vacuuo to give 270 mg of 4-bromo-3-methoxy-2-thiophene sulfonylchloride (33%) as a light yellow oil.

Step E

To a stirred solution of thiophene sulfonylchloride (270 mg, 0.926 mmol) prepared in Step D above in 15 mL of methylene chloride at room temperature was added triethylamine followed by N-methyl-tertbutylamine (0.25 mL, 2.094 mmol). After 20 h, the mixture was diluted with 50 mL of methylene chloride, and washed with $H_2O$ and brine. The organic solution was dried over $Na_2SO_4$, filtered, and concentrated to an oily residue, which was purified by preparative TLC (methylene chloride as eluent) to afford 73 mg of the titled bromo-sulfonamide (23%) as a near colorless oil.

Step F

A one-neck round bottom flask was charged with bromo-sulfonamide (73 mg, 0.2133 mmol, from Step E above), palladium acetate (5 mg, 0.0223 mmol), binap (0.03212 mmol), cesium carbonate (139 mg, 0.4266 mmol), and benzophenonimine (0.06 mL, 0.358 mmol). The mixture was evacuated via house vacuum, and refilled with nitrogen. A 3 mL of anhydrous toluene was added. The mixture was evacuated again, refilled with nitrogen, and heated a reflux for 2.5 d. After cooled to room temperature, methylene chloride (50 mL) was added, the mixture was filtered through a Celite pad, rinsing with methylene chloride. The filtrated was concentrated in vacuo to give 205 mg (crude, $MH^+=443.1$) of the desired imine product as a dark brown oil, used in next step without purification.

Step G

The imine from Step F above (205 mg, crude, 0.2133 mmol) was dissolved in 5 mL of methanol, and added with sodium acetate (81 mg, 0.9873 mmol) followed by hydroxylamine hydrochloride (68 mg, 0.98 mmol). The mixture was stirred at room temperature for 6.5 h, quenched with the addition of 10 mL of a 1.0 M NaOH aqueous solution. The aqueous mixture was extracted with methylene chloride (30 mL×3). The extracts were combined, washed with brine, dried by $Na_2SO_4$, and concentrated in vacuo to a dark yellow oil, which was purified by preparative TLC (methylene chloride-methanol=100:1, v/v) to give 34 mg (57% over two steps, MH⁺=279.0) of methoxy-thiophenesulfonamide amine as a light yellow oil, solidified on standing.

Step H

To a stirred suspension of sodium hydride (60%, 45 mg, 1.13 mmol) in 3 mL of anhydrous N,N'-dimethylformamide (DMF) was added dropwise ethanethiol (0.1 mL, 1.34 mmol). After 10 min, the mixture tured into a clear solution, and 1 mL of this solution was taken up in a syringe and added dropwise to a stirred solution of methoxy-thiophene-sulfonamide amine in 1 mL of DMF. The mixture was heated up to 95° C., and continued for 3.5 h. After cooling, the mixture was poured into 20 mL of a 1.0 M NaOH aqueous solution. The aqueous mixture was washed with methylene chloride (30 mL×3). The organic washings were combined, re-extracted with a 1.0 M NaOH aqueous solution (15 mL) and H₂O (15 mL). The aqueous layer and aqueous extracts were combined, adjusted to pH~6 using a 1.0 M HCl aqueous solution, and extracted with methylene chloride (75 mL×3). The organic extracts were washed with brine, dried (Na₂SO₄), and concentrated in vacuo to a dark yellow oil. This oil was dissolved in ethyl acetate (50 mL), washed with H₂O (10 mL×2) and brine (10 mL). The organic solution was dried (Na₂SO₄), and concentrated in vacuo to afford 36 mg (100%, MH⁺=265.0) of hydroxyl-thiophene sulfonamide amine as a yellow oil.

PREPARATIVE EXAMPLE 16.1

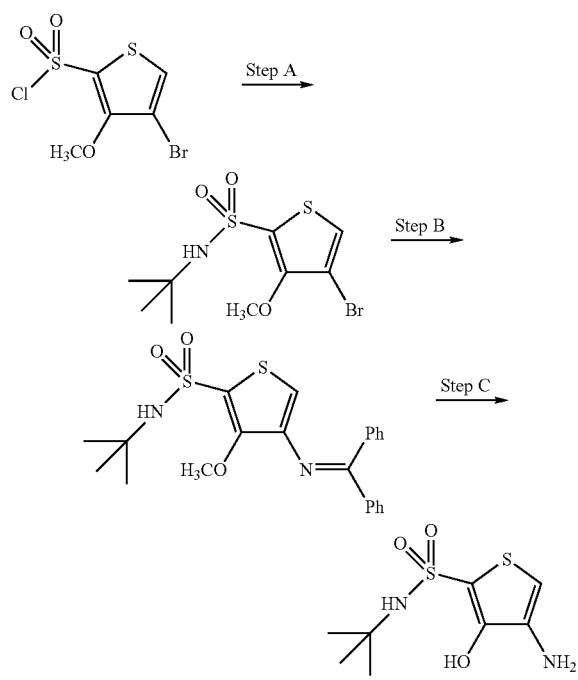

Step A

Following the procedures described in Preparative example 16 Step E, 4-bromo-3-methoxy-2-thiophene-sulfonyl chloride (190 mg, 0.65 mmol, available from Step D, Preparative example 16) was converted to the titled tert-butyl sulfonamide (56 mg, 26%, MH⁺=328.1) upon treatment of triethylamine (0.28 mL, 2.0 mmol) and tert-butylamine (0.15 mL, 1.43 mmol) in 10 mL of methylene chloride.

Step B tert-Butyl sulfonamide (98 mg, 0.3 mmol) available from Step A above was converted to the imine product (296 mg, crude, MH⁺=429.1) by using the procedure described in Step F of Preparative example 16

Step C

Following the procedures described in Preparative Example 6, Step F and G, the imine product (108 mg, crude, ~0.25 mmol) from Step B above was transformed to the desired hydroxyl-thiophene amine (25 mg, 40% over two steps, MH⁺=251.0)

PREPARATIVE EXAMPLE 16.2

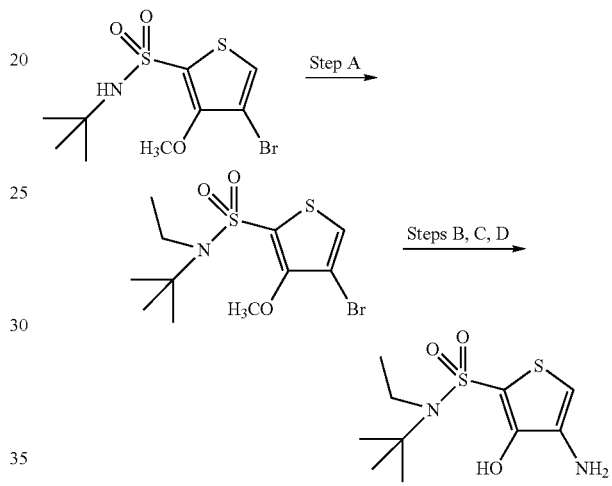

Step A tert-Butyl-thiophene sulfonamide available from Preparative Example 16.1 Step A (164 mg, 050 mmol) was treated with potassium carbonate (700 mg. 5 mmol) and iodoethane (0.4 mL 5 mmol) in acetone and refluxed for 1.5 d. The mixture was filtered, and the solid material was washed with methylene chloride. The combined filtrated and washing were concentrated purified by flash column chromatography eluting with 0 to 30% methylene chloride in hexanes. Removal of solvents afforded the ethyl-tert-butyl-sulfonamide (151 mg, 85%).

Steps B, C and D

Following the procedures described in Preparative Example 16, Steps F, G and H, ethyl-tert-butyl sulfonamide (150 mg, 0.42 mmol) from Step A above was converted to the hydroxyl-amino-thiophene (45 mg, 38%, MH⁺=279.1).

PREPARATIVE EXAMPLE 16.3

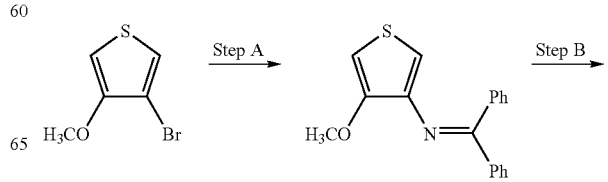

83

-continued

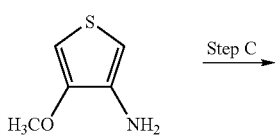

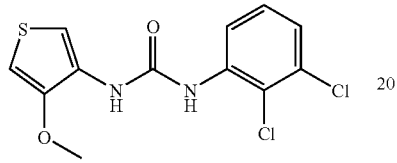

Step A

Following the procedure described in Preparative Example 1 Step F, 3-bromo-4-methoxy-thiophene (0.90 g, 4.66 mmol) available from Preparative Example 16, Step C, was converted to the corresponding imine (2.4 g, crude, before purification, MH$^+$=294.0).

Step B

The imine compound from Step A above (crude material, 2.4 g) was dissolved in methanol (40 mL) and methylene chloride (10 mL). Sodium acetate (0.92 g, 11.2 mmol) and hydroxyl amine hydrochloride (0.58 g, 8.35 mmol) were added. After stirred for 3 h at room temperature, 30 mL of a 1.0 M NaOH aqueous solution was added. The mixture was extracted with methylene chloride (75 mL×3). The organic extracts were washed with brine, dried by Na$_2$SO$_4$, and concentrated in vacuo to an oily residue. This residue was stirred with 20 mL of a 1.0 M HCl aqueous solution for 2 h, washed with ether (30 mL×3), then adjusted to pH~12 using a 1.0 M NaOH aqueous solution. The aqueous mixture was extracted with methylene chloride (50 mL×4). The organic extracts were washed with brine, dried, and concentrated to give 3-amino-4-methoxy-thiophene (0.414 g, 69% over two steps, MH$^+$=130.0).

Step C

A mixture of 3-amino-4-methoxy-thiophene (405 mg, 3.135 mmol) available from Step B above and 2,3-dichlorophenyl isocyanate (0.74 g, 3.94 mmol) in 30 mL of methylene chloride was stirred at room temperature over night. The near colorless precipitates were collected by filtration, washed with hexanes, and dried on high vacuum, yielding 795 mg of the titled urea compound (80%, MH$^+$=317.1).

PREPARATIVE EXAMPLE 17

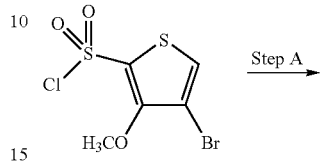

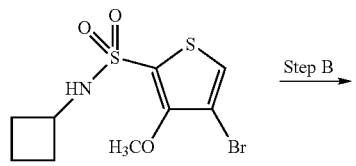

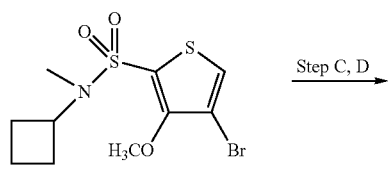

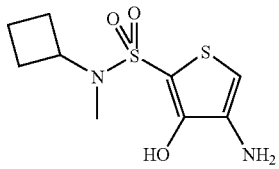

Step A

Following the procedure described in Preparative Example 16, Step E, except using cyclobutyl amine in place of N-methyl-N-tert butyl amine, the cyclobutyl-thiophene sulfonamide was prepared.

Step B

Cyclobutyl-thiophene-sulfonamide (325 mg, 0.99 mmol), available from Step A above, was methylated following a similar procedure used in Preparative Example 16.2 Step A to give the desired product (300 mg, 89%, MH$^+$=342.1).

Steps C and D

Following the procedures used in Preparative Example 1 steps F and G, the bromide from Step B above (300 mg, 0.88 mmol) was converted to the titled hydroxyl-amino-thiophene (78.5 mg, 34%, MH$^+$=263.0).

PREPARATIVE EXAMPLE 17.1

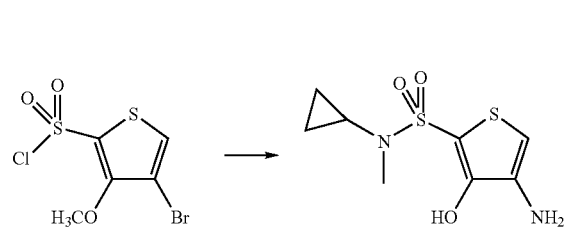

Following the procedures used for the Preparative Example 17, except using cyclopropyl amine in Step A in place of cyclobutyl mine, the titled hydroxyl-amino-thiophene was obtained (MH$^+$=249.0).

EXAMPLE 20

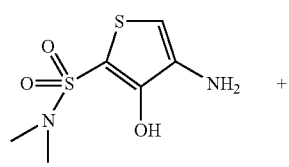 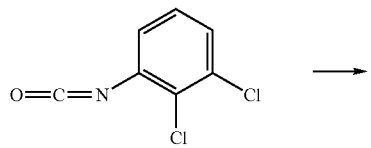

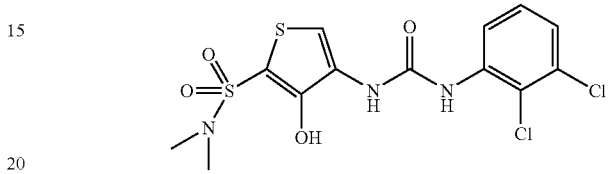

To a stirred solution of hydroxyl-amino-thiophene-dimethylsulfonamide (50 mg, 0.225 mmol), available from Preparative Example 2.1, in 2 mL of $CH_2Cl_2$ at room temperature was added 2,3-dichlorophenylisocyanate (240 mg, 1.28 mmol). After 14 h (over night), solvent was evaporated, the oily residue was separated by preparative TLC ($CH_2Cl_2$-MeOH=30:1, v/v, 2 elutions) to afford 67.5 mg (73%) of the urea product as a light yellow solid (M$^+$=410.07).

EXAMPLES 20.1-20.2

Following the procedures described in Example 20, except using the isocyanates identified and the hydroxyl-amino-thiophene-dimethylsulfonamide from Preparative Example 2.1, the urea-type of products in Table 3 below were obtained.

TABLE 3

| Ex. No. | Isocyanate | Product | 1. Yield %<br>2. MH$^+$<br>3. m.p. (° C.) |
|---|---|---|---|
| 20.1 | | ![urea product with Br substituents] | 1. 42%<br>2. 420.1<br>3. 133–135 |
| 20.2 | | ![urea product] | 1. 46%<br>2. 342.1<br>3. 71–73 |

EXAMPLES 20.3-20.21

Following the procedures described in Example 20, except using the hydroxyl-thiophene-amines prepared and the commercially available isocyantes identified, the urea-type of compounds in Table 4 below were prepared.

TABLE 4

| Ex. No. | Amine (Prep. Ex.) | Isocyanate | Product | 1. Yield %<br>2. MH+<br>3. m.p. (° C.) |
|---|---|---|---|---|
| 20.3 | (1) | | | 1. 69%<br>2. 438.1<br>3. 96–98 |
| 20.4 | (4) | | | 1. 96%<br>2. 474.0<br>3. 197–198 |
| 20.5 | (4.1) | | | 1. 72%<br>2. 452.1<br>3. 128 (decomp) |
| 20.6 | (1) | | | 1. 69%<br>2. 442.1<br>3. 87–89 |
| 20.7 | (3.1) | | | 1. 61%<br>2. 410.1<br>3. 145 (decomp) |
| 20.8 | (3.1) | | | 1. 40%<br>2. 392.1<br>3. 152 (decomp) |

TABLE 4-continued

| Ex. No. | Amine (Prep. Ex.) | Isocyanate | Product | 1. Yield %<br>2. MH+<br>3. m.p. (° C.) |
|---|---|---|---|---|
| 20.9 | Et-NH-SO2-thiophene-OH-NH2 (3.1) | OCN-Ph-Ph | EtNH-SO2-thiophene-OH-NH-C(O)-NH-Ph-Ph | 1. 18%<br>2. 418<br>3. 168.2 |
| 20.10 | Et-NH-SO2-thiophene-OH-NH2 (3.1) | OCN-Ph-Br | EtNH-SO2-thiophene-OH-NH-C(O)-NH-Ph-Br | 1. 23%<br>2. 420<br>3. 202.3–208.8 |
| 20.11 | iPr-NH-SO2-thiophene-OH-NH2 (3.2) | OCN-Ph-Cl,Cl | iPrNH-SO2-thiophene-OH-NH-C(O)-NH-Ph-Cl,Cl | 1. 35%<br>2. 424<br>3. 168–172 |
| 20.12 | iPr-NH-SO2-thiophene-OH-NH2 (3.2) | OCN-Ph-Br | iPrNH-SO2-thiophene-OH-NH-C(O)-NH-Ph-Br | 1. 52%<br>2. 434<br>3. 170–173 |
| 20.13 | tBu-NH-SO2-thiophene-OH-NH2 (16.1) | OCN-Ph-Cl,Cl | tBuNH-SO2-thiophene-OH-NH-C(O)-NH-Ph-Cl,Cl | 1. 17%<br>2. 438.1<br>3. 181–185 |
| 20.14 | tBu(Me)N-SO2-thiophene-OH-NH2 (16) | OCN-Ph-Cl,Cl | tBu(Me)N-SO2-thiophene-OH-NH-C(O)-NH-Ph-Cl,Cl | 1. 23%<br>2. 452.1<br>3. 162 (decomp) |
| 20.15 | tBu(Et)N-SO2-thiophene-OH-NH2 (16.2) | OCN-Ph-Cl,Cl | tBu(Et)N-SO2-thiophene-OH-NH-C(O)-NH-Ph-Cl,Cl | 1. 65%<br>2. 466.1 |

TABLE 4-continued
| Ex. No. | Amine (Prep. Ex.) | Isocyanate | Product | 1. Yield %<br>2. MH+<br>3. m.p. (° C.) |
|---|---|---|---|---|
| 20.16 | 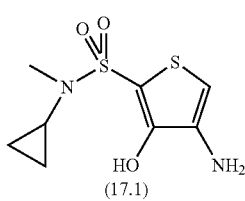<br>(17.1) | 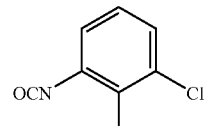 | 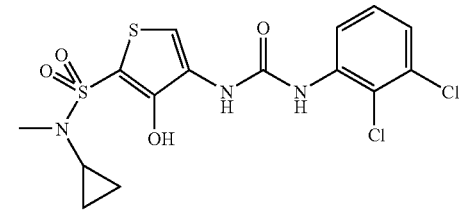 | 1. 7.4%<br>2. 436.1 |
| 20.17 | 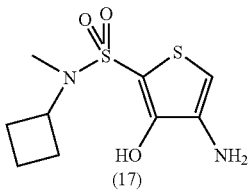<br>(17) | 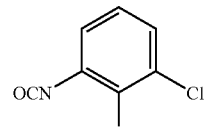 | 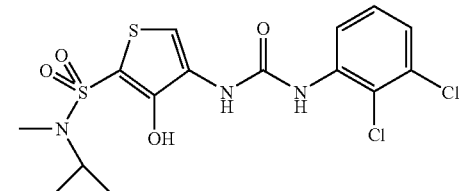 | 1. 31%<br>2. 450.1 |
| 20.18 | 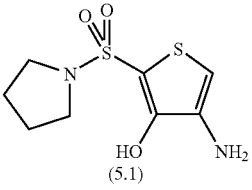<br>(5.1) | 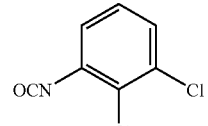 | 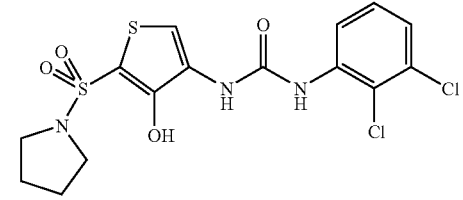 | 1. 27%<br>2. 436<br>3. 165–170 |
| 20.19 | 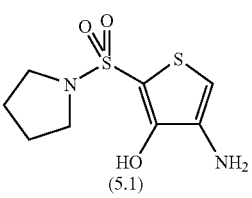<br>(5.1) | 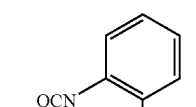 | 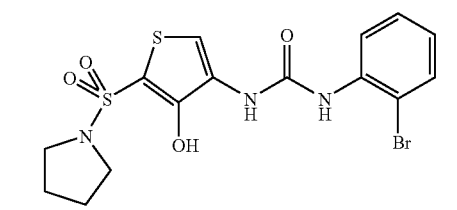 | 1. 17%<br>2. 446<br>3. 134–140 |
| 20.20 | 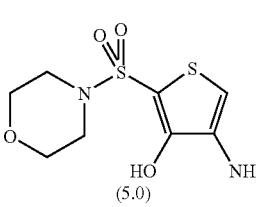<br>(5.0) | 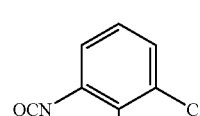 | 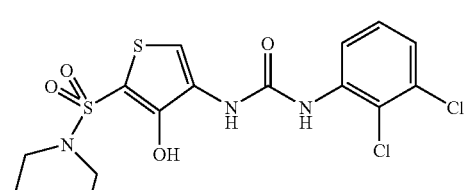 | 1. 13%<br>2. 452.1<br>3. 212 (decomp) |
| 20.21 | 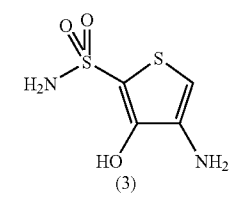<br>(3) | 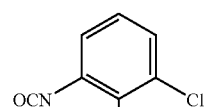 | 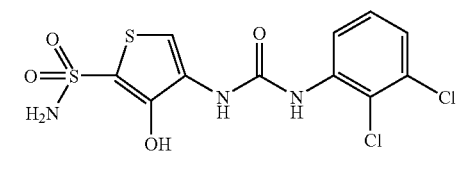 | 1. 7.6%<br>2. 382.1<br>3. 171 (decomp) |

EXAMPLE 21

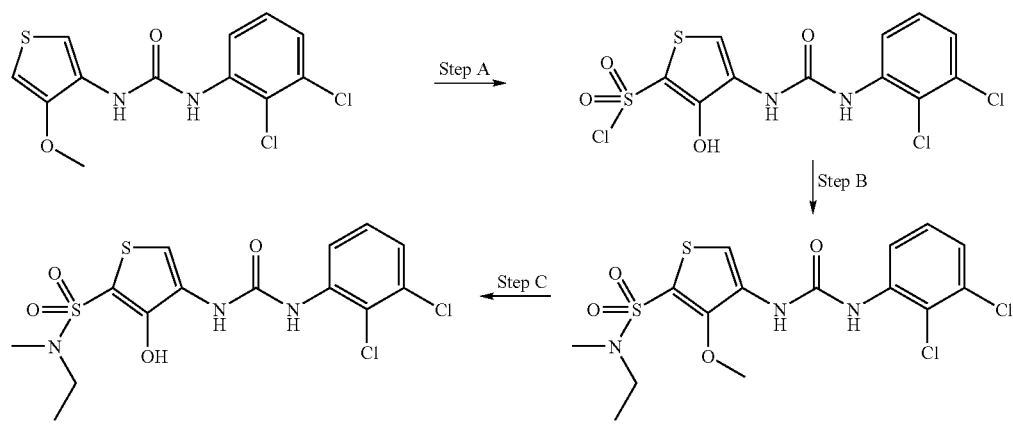

Step A

2-H-thiophene-urea (85 mg, 0.27 mmol), available from Step C of Preparative Example 16.3, was partially dissolved in methylene chloride (4 mL and added dropwise to a stirred solution of chlorosulfonic acid (0.09 mL, 1.35 mmol) in 4 mL of methylene chloride at room temperature. After 10 min, the mixture was poured into crushed ice and extracted with ethyl acetate several times. The extracts were washed with water and brine, dried with sodium sulfate, and concentrated to give the corresponding thiophene sulfonyl chloride as a greenish oil (45 mg) used in next step directly.

Step B

A mixture of thiophene sulfonyl chloride (from Step A above), N-methyl-N-ethyl amine (0.05 mL), and triethyl amine (0.16 mL) in 3 mL of methylene chloride was stirred at room temperature over night. Upon aqueous work up, an oily material was obtained, which was purified by preparative TLC to give the desired product (6 mg, 5% over two steps, MH$^+$=437.0).

Step C

The methoxy-thiophene urea compound (6 mg), available from Step B above, was dissolved in 2 mL of methylene chloride and cooled in an ice bath. A 1.0 M solution of boron tribromide in methylene chloride (0.05 mL) was added. The mixture was stirred at 0° C. for 15 min and continued at room temperature for 30 min, and quenched with water. The aqueous mixture was extracted with methylene chloride, the extracts were washed with brine, dried by Na$_2$SO$_4$, and concentrated in vacuuo to give an oily residue, which was purified by preparative TLC to afford the titled product (4 mg, 95%, MH$^+$=424).

EXAMPLES 21.1-21.14

Following the procedures described in Example 21, except using the amines indicated in Table 5, the corresponding urea compounds were synthesized.

TABLE 5

| Ex. No. | R$^1$R$^2$NH | Product | 1. Yield %<br>2. MH$^+$ |
|---|---|---|---|
| 21.1 | (structure) | (structure) | 1. 2%<br>2. 438 |
| 21.2 | (structure) | (structure) | 1. 5%<br>2. 452 |

TABLE 5-continued
| Ex. No. | R¹R²NH | Product | 1. Yield %<br>2. MH⁺ |
|---|---|---|---|
| 21.3 | 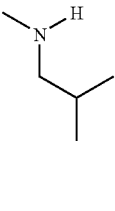 | 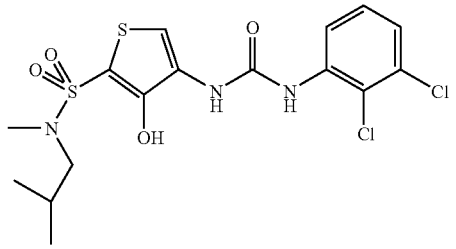 | 1. 5%<br>2. 452.1 |
| 21.4 | 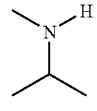 | 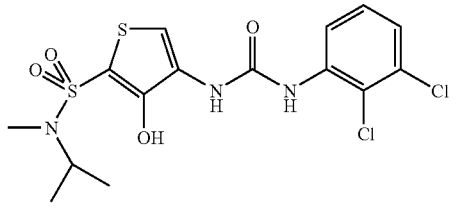 | 1. 9.4%<br>2. 438.1 |
| 21.5 | 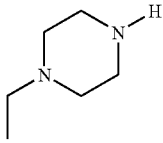 | 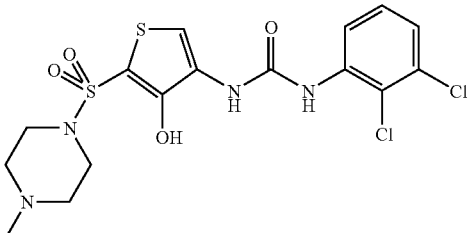 | 1. 10%<br>2. 479 |
| 21.6 | 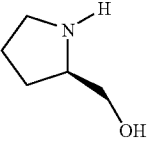 | 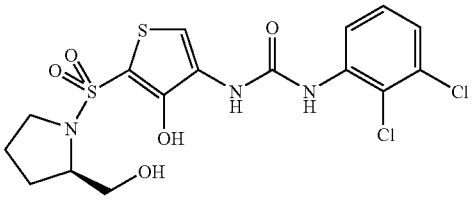 | 1. 7%<br>2. 466 |
| 21.7 | 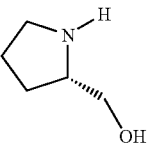 | 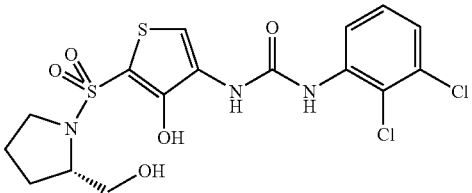 | 1. 2%<br>2. 466 |
| 21.8 | 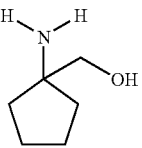 | 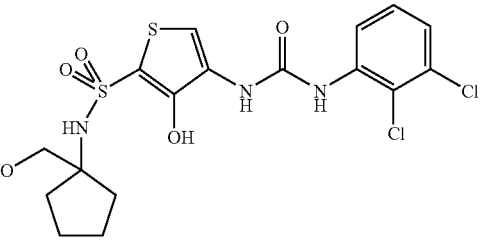 | 1. 5%<br>2. 480.1 |

TABLE 5-continued
| Ex. No. | R¹R²NH | Product | 1. Yield %<br>2. MH⁺ |
|---|---|---|---|
| 21.9 | 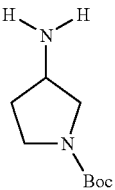 | 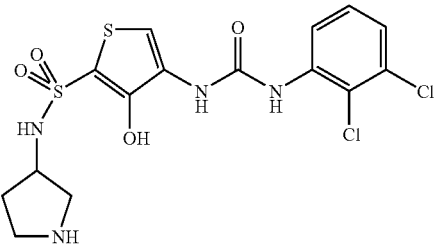 | 1. 1%<br>2. 451 |
| 21.10 | 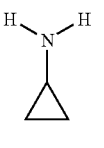 | 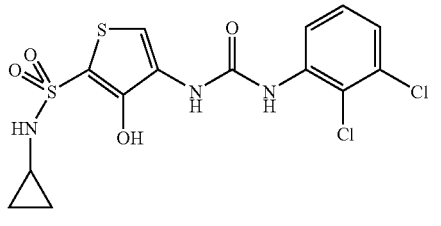 | 1. 9.3%<br>2. 422.1 |
| 21.11 | 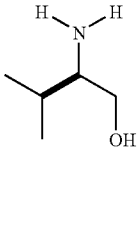 | 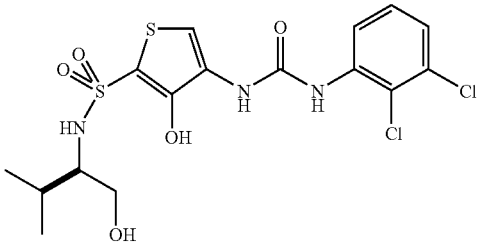 | 1. 10%<br>2. 468.1 |
| 21.12 | 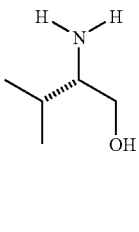 | 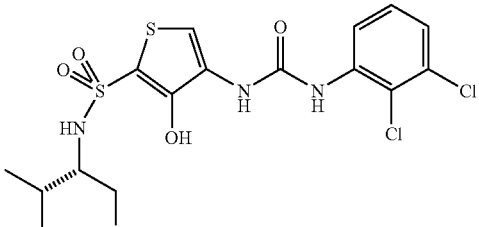 | 1. 3.3%<br>2. 468.1 |
| 21.13 | 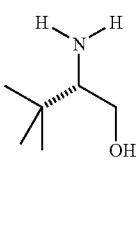 | 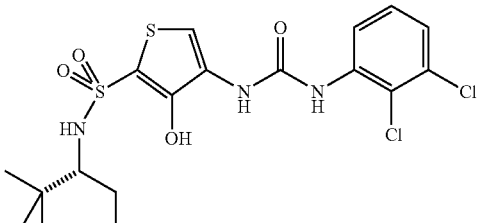 | 1. 3%<br>2. 482.1 |
| 21.14 | 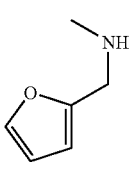 | 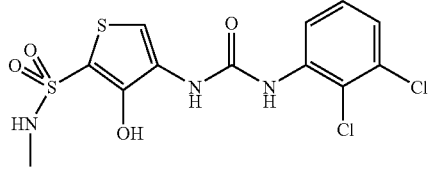 | 1. 2.5%<br>2. 396.1 |

EXAMPLE 22

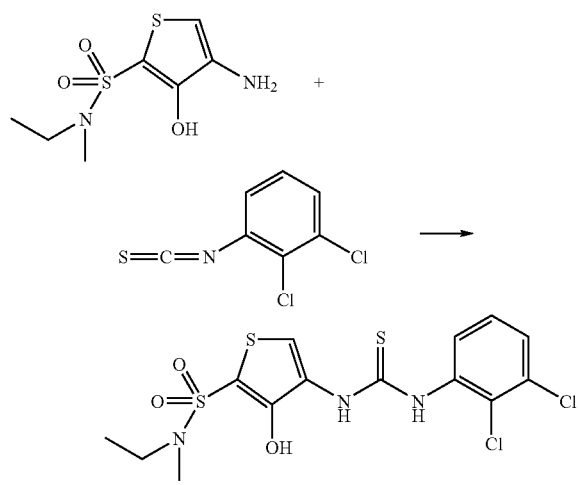

A mixture of thiophene-amine (50 mg, 0.212 mmol), available from Preparative Example 2.2, and 2,3-dichlorophenyl-isothiocyanate (90 mg, 0.441 mmol) in 2 mL of CH$_2$Cl$_2$ was stirred at room temperature for 2 d. The mixture was diluted with CH$_2$Cl$_2$ (30 mL), washed with a saturated NaHCO$_3$ aqueous solution, H$_2$O, a 1.0 N HCl aqueous solution, and brine. The organic solution was dried by Na$_2$SO$_4$, concentrated to an oily residue, and purified by preparative TLC (CH$_2$Cl$_2$-MeOH=30:1, v/v, 2 elutions) to give 10.3 mg (11%) of the desired product as a light yellow solid (MH$^+$=442.1, m.p.112-115° C.).

EXAMPLES 30.2-30.7

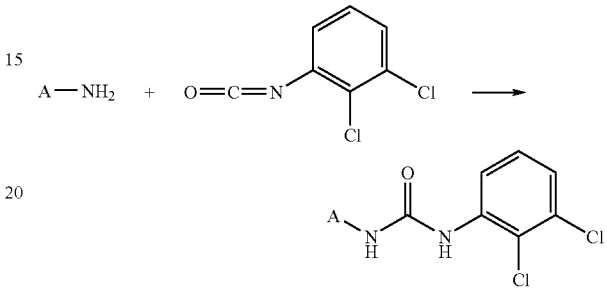

Following the procedures described in Example 20, except using the amines (A-NH$_2$) identified, the urea-type products in Table 6 below may be obtained.

TABLE 6

| Ex. No. | A-NH2 | (Prep. Ex.) | Product |
|---|---|---|---|
| 30.2 | {width=0} | (6) | |
| 30.3 | | (7) | |
| 30.4 | | (8) | |
| 30.5 | | (9) | |

TABLE 6-continued
| Ex. No. | A-NH2 | (Prep. Ex.) | Product |
|---|---|---|---|
| 30.6 | | (10) | |
| 30.7 | | (11) | |
EXAMPLES 30.8. 30.9 and 30.11-30.20
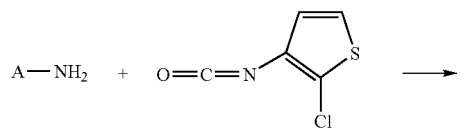
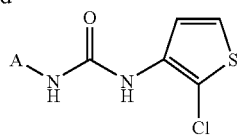
Following the procedures described in Example 20, except using the amines (A-NH$_2$) identified, and 2-chloro-3-thiophene-isocyanate from Preparative Example 12, the urea-type products in Table 7 below may be obtained.
TABLE 7
| Ex. No. | A-NH2 (Prep. Ex.) | Product |
|---|---|---|
| 30.8 | (2.1) | |
| 30.9 | (2.2) | |
| 30.11 | (16) | |

TABLE 7-continued

| Ex. No. | A-NH2 (Prep. Ex.) | | Product |
|---|---|---|---|
| 30.12 | [structure] | (17.1) | [structure] |
| 30.13 | [structure] | (5.1) | [structure] |
| 30.14 | [structure] | (3) | [structure] |

TABLE 8

| Ex. No. | A-NH2 (Prep. Ex.) | | Product |
|---|---|---|---|
| 31.1 | [structure] | (2.1) | [structure] |
| 31.2 | [structure] | (2.2) | [structure] |
| 31.3 | [structure] | (16) | [structure] |
| 31.4 | [structure] | (17.1) | [structure] |

TABLE 8-continued
| Ex. No. | A-NH2 (Prep. Ex.) | | Product |
|---|---|---|---|
| 31.5 | 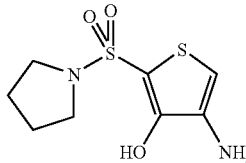 | (5.1) | 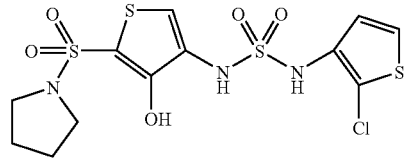 |
| 31.6 | 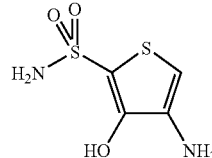 | (3) | 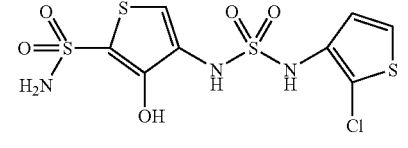 |
| 31.7 | 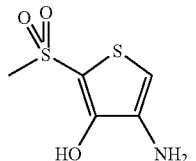 | (6) | 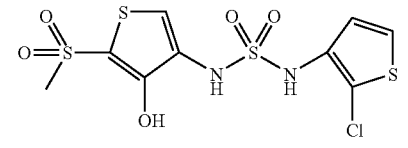 |
| 31.8 | 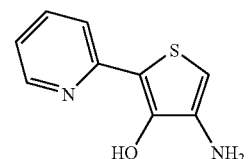 | (7) | 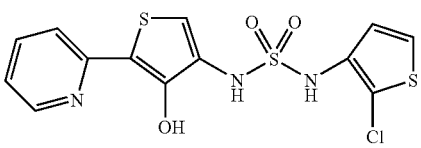 |
| 31.9 | 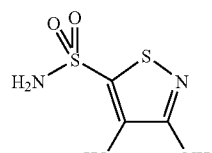 | (8) | 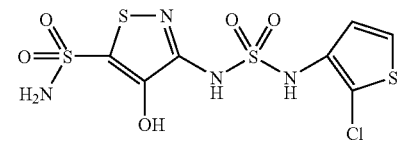 |
| 31.10 | 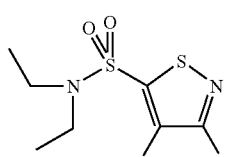 | (9) | 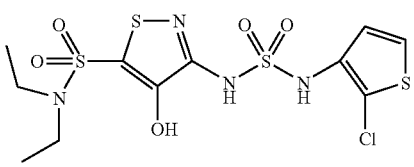 |
| 31.11 | 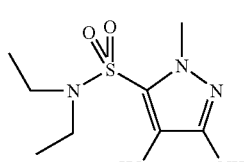 | (10) | 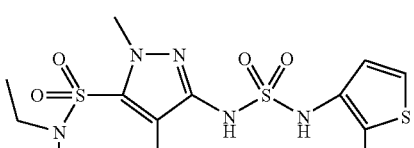 |
| 31.12 | 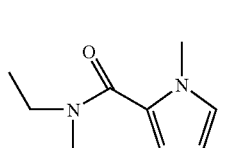 | (11) | 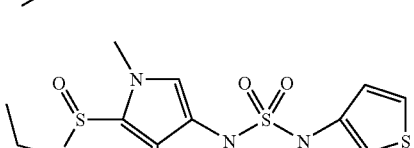 |

EXAMPLES 32.1-32.11
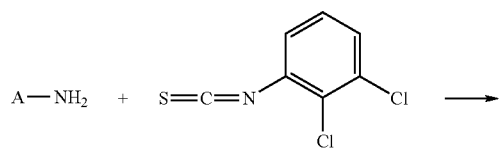
Following the procedure set forth in Example 22, except using the amines A-NH₂ identified, thiourea-products listed in Table 9 below may be prepared.
TABLE 9
| Ex. No. | A-NH2 (Prep. Ex.) | | Product |
|---|---|---|---|
| 32.1 | 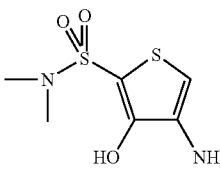 | (2.1) | 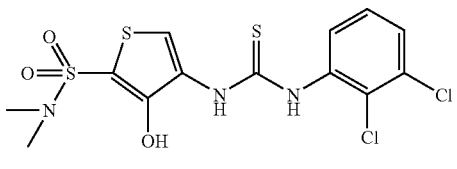 |
| 32.2 | 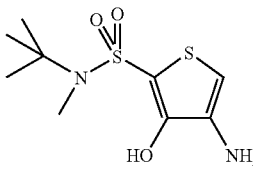 | (16) | 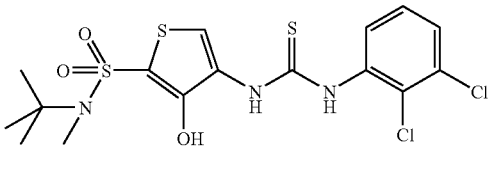 |
| 32.3 | 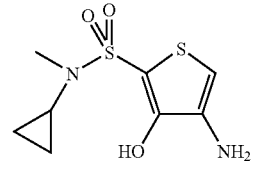 | (17.1) | 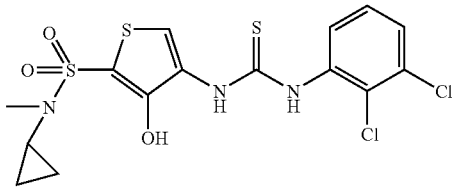 |
| 32.4 | 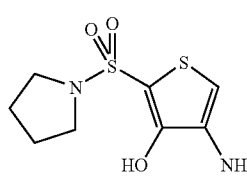 | (5.1) | 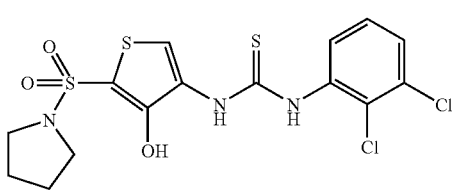 |
| 32.5 | 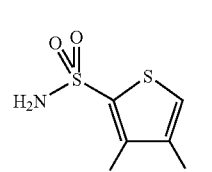 | (3) | 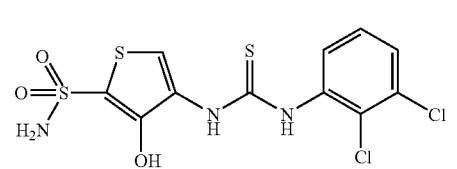 |
| 32.6 | 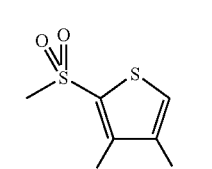 | (6) | 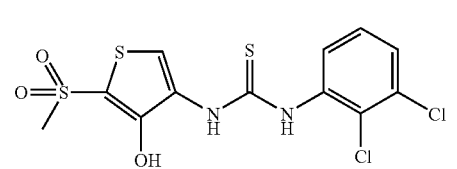 |

TABLE 9-continued

| Ex. No. | A-NH2 (Prep. Ex.) | Product |
|---|---|---|
| 32.7 | (7) | |
| 32.8 | (8) | |
| 32.9 | (9) | |
| 32.10 | (10) | |
| 32.11 | (11) | |

EXAMPLE 33

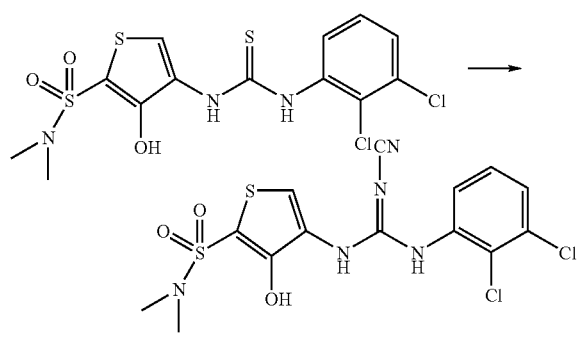

Dichloroanilino-thiourea compound, available from Example 32.1, may be directly converted to the corresponding cyanoguanidine by treatment with Lead cyanamide (PbNCN) in refluxing acetonitrile-DMF solution (See: *Bioorg. Med. Chem. Lett.,* 2000, 10, 265-268; *J. Med. Chem.,* 1977, 20, 90 1).

EXAMPLE 33.1-33.11

Following the procedure used in Example 33, cyanoguanidine compounds listed in Tabel 10 below may be prepared from their corresponding thiourea precursors.

TABLE 10

| Ex. No. | Thioureas | (Prep. Ex.) | Product |
|---|---|---|---|
| 33.1 | | (21) | |
| 33.2 | | (32.2) | |
| 33.3 | | (32.3) | |
| 33.4 | | (32.4) | |
| 33.5 | | (32.5) | |

TABLE 10-continued

| Ex. No. | Thioureas | (Prep. Ex.) | Product |
|---|---|---|---|
| 33.6 | | (32.6) | |
| 33.7 | | (32.7) | |
| 33.8 | | (32.8) | |
| 33.9 | | (32.9) | |
| 33.10 | | (32.10) | |
| 33.11 | | (32.11) | |

The compounds of the present invention are useful in the treatment of CXC-chemokine mediated conditions and diseases. This utility is manifested in their ability to inhibit IL-8 and GRO-α chemokine as demonstrated by the following in vitro assays.

Receptor Binding Assays:

CXCR1 SPA Assay

For each well of a 96 well plate, a reaction mixture of 2.2 μg hCXCR1-CHO overexpressing membranes (Biosignal) and 100 μg/well WGA-SPA beads (Amersham) in 160 μl was prepared in CXCR1 assay buffer (25 mM HEPES, pH 7.8, 2 mM $CaCl_2$, 1 mM $MgCl_2$, 125 mM NaCl, 0.1% BSA) (Sigma). A 0.5 nM stock of ligand, [125I]-IL-8 (NEN) was prepared in the CXCR1 assay buffer. 10× stock solutions of test compounds were prepared in 10% DMSO (Sigma). The above solutions were added to a 96-well assay plate (PerkinElmer) as follows: 20 μl test compound or DMSO, 160 μl of reaction mixture, 20 μl of ligand stock (Final [Ligand]= 0.05 nM). The assay plates were shaken for 5 minutes on plate shaker, then incubated for 12 hours before cpm/well were determined in Microbeta Trilux counter (PerkinElmer). % Inhibition of Total binding-NSB (250 nM IL-8) was determined for $IC_{50}$ values.

For the CXCR1 assay, the compounds of Examples 20, 20.1, 20.3, 20.4, 20.5, 20.6, 20.7, 20.8, 20.9, 20.10, 20.11, 20.12, 20.13, 20.14, 20.15, 20.16, 20.17, 20.18, 20.19, 20.20, 20.21, 21, 21.1, 21.2, 21.3, 21.4, 21.5, 21.6, 21.7, 21.8, 21.9, 21.10, 21.11, 21.12, 21.13, 21.14, and 22 had a $K_i$ of within the range of 0.652 µM to >29 µM.

For the CXCR1 assay, the compounds of Examples 20.3, 20.11, 20.13, 20.14, 20.15, 20.16, 20.18, 20.19, 21.5, 21.6, 21.7, 21.10, and 21.14 had a $K_i$ of within the range of 0.652 µM to 1.92 µM.

The compound of Example 20.14 had a $K_i$ of 0.652 µM

CXCR2 SPA Assay

For each well of a 96 well plate, a reaction mixture of 2.5 µg hCXCR2-CHO overexpressing membranes (Biosignal) and 200 µg/well WGA-SPA beads (Amersham) in 160 µl was prepared in CXCR2 assay buffer (25 mM HEPES, pH 7.4, 2 mM CaCl$_2$, 1 mM MgCl$_2$). A 1 nM stock of ligand, [125I]-IL-8 (NEN), was prepared in the CXCR2 assay buffer. 10× stock solutions of test compounds were prepared in DMSO (Sigma). The above solutions were added to a 96-well assay plate (PerkinElmer or Corning) as follows: 20 µl test compound or DMSO, 160 µl of reaction mixture, 20 µl of ligand stock (Final [Ligand]=0.1 nM). The assay plates were shaken for 5 minutes on a plate shaker, then incubated for 12 hours before cpm/well were determined in Microbeta Trilux counter (PerkinElmer).

For the CXCR2 assay, the compounds of Examples Examples 20, 20.1, 20.3, 20.4, 20.5, 20.6, 20.7, 20.8, 20.9, 20.10, 20.11, 20.12, 20.13, 20.14, 20.15, 20.16, 20.17, 20.18, 20.19, 20.20, 20.21, 21, 21.1, 21.2, 21.3, 21.4, 21.5, 21.6, 21.7, 21.8, 21.9, 21.10, 21.11, 21.12, 21.13, 21.14, and 22 had a $K_i$ of within the range of 5 nM to 14800 nM.

For the CXCR2 assay, the compounds of Examples Examples 20, 20.1, 20.3, 20.7, 20.10, 20.12, 20.15, 20.16, 20.17, 20.18, 20.19, 20.21, 21, 21.1, 21.2, 21.3, 21.4, 21.5, 21.6, 21.7, 21.8, 21.10, 21.12, 21.14 and 22 had a $K_i$ of within the range of 5 nM to 91 nM.

For the CXCR2 assay, the compounds of Examples Examples 20.16, 21.1, 21.4, 21.6, 21.7 and 21.14, had a $K_i$ of within the range of 5 nM to 10 nM.

For the CXCR2 assay, the compound of Example 20.16 had a $K_i$ of 6 nM.

Calcium Fluorescence Assay (FLIPR)

HEK 293 cells stably transfected with hCXCR2 and Gαζ/q could be plated at 10,000 cells per well in a Poly-D-Lysine Black/Clear plate (Becton Dickinson) and could be incubated 48 hours at 5% CO$_2$, 37° C. The cultures could then be incubated with 4 mM fluo-4, AM (Molecular Probes) in Dye Loading Buffer (1% FBS, HBSS w. Ca & Mg, 20 mM HEPES (Cellgro), 2.5 mM Probenicid (Sigma) for 1 hour. The cultures could be washed with wash buffer (HBSS w Ca, & Mg, 20 mM HEPES, Probenicid (2.5 mM)) three times, then 100 µl/well wash buffer could be added.

During incubation, compounds could be prepared as 4× stocks in 0.4% DMSO (Sigma) and wash buffer and could be added to their respective wells in the first addition plate. IL-8 or GRO-α (R&D Systems) concentrations could be prepared 4× in wash buffer +0.1% BSA and could be added to their respective wells in second addition plate.

Culture plate and both addition plates could then be placed in the FLIPR imaging system to determine change in calcium fluorescence upon addition of compound and then ligand. Briefly, 50 µl of compound solutions or DMSO solution could be added to respective wells and change in calcium fluorescence measured by the FLIPR for 1 minute. After a 3 minute incubation within the instrument, 50 µl of ligand could then be added and the change in calcium fluorescence measured by the FLIPR instrument for 1 minute. The area under each stimulation curve could be determined and values could be used to determine % Stimulation by compound (agonist) and % Inhibition of Total Calcium response to ligand (0.3 nM IL-8 or GRO-α) for IC50 values of the test compounds.

Chemotaxis Assays for 293-CXCR2

A chemotaxis assay is setup using Fluorblok inserts (Falcon) for 293-CXCR2 cells (HEK-293 cells overexpressing human CXCR2). The standard protocol used at present is as follows:

1. Inserts are coated with collagenIV (2 µg/ml) for 2 hrs at 37° C.

2. The collagen is removed and inserts are allowed to air dry overnight.

3. Cells are labeled with 10 µM calcein AM (Molecular Probes) for 2 hrs. Labeling is done in complete media with 2% FBS.

4. Dilutions of compound are made in minimal media (0.1% BSA) and placed inside the insert which is positioned inside the well of a 24 well plate. Within the well is IL-8 at a concentration of 0.25 nM in minimal media. Cells are washed and resuspended in minimal media and placed inside the insert at a concentration of 50,000 cells per insert.

5. Plate is incubated for 2 hrs and inserts are removed and placed in a new 24 well. Fluorescence is detected at excitation=485 nM and emission=530 nM.

Cytotoxicity Assays

A cytotoxicity assay for CXCR2 compounds could be conducted on 293-CXCR2 cells. Concentrations of compounds could be tested for toxicity at high concentrations to determine if they could be used for further evaluation in binding and cell based assays. The protocol could be as follows:

1. 293-CXCR2 cells could be plated overnight at a concentration of 5000 cells per well in complete media.

2. Dilutions of compound could be made in minimal media w/0.1% BSA. Complete media could be poured off and the dilutions of compound could be added. Plates are incubated for 4, 24 and 48 hrs. Cells could be labeled with 10 µM calcein AM for 15 minutes to determine cell viability. Detection method could be the same as above.

Soft Agar Assay 10,000 SKMEL-5 cells/well could be placed in a mixture of 1.2% agar and complete media with various dilutions of compound. Final concentration of agar could be 0.6%. After 21 days viable cell colonies could be stained with a solution of MTT (1 mg/ml in PBS). Plates could then be scanned to determine colony number and size. IC$_{50}$ could be determined by comparing total area vs. compound concentration.

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

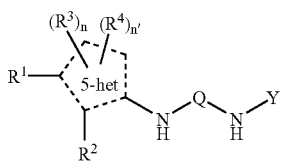

(1)

and the pharmaceutically acceptable salts and solvates thereof, wherein:

Y is selected from the group consisting of:

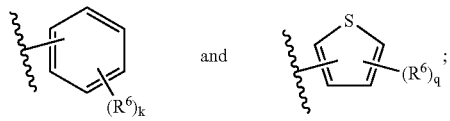

Q is selected from the group consisting of:

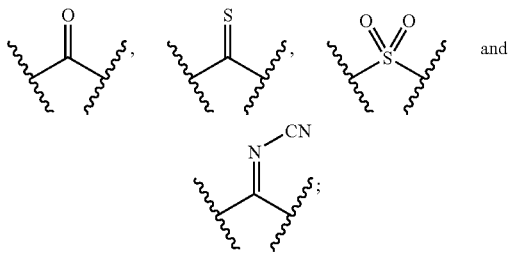

the ring of the 5-het moiety is a heteroaryl selected from the group consisting of:

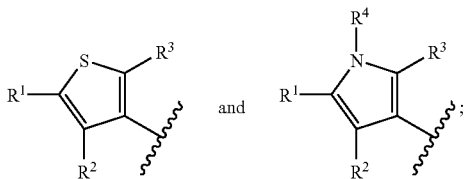

$R^1$ is selected from the group consisting of: hydrogen, halogen, unsubstituted alkyl, substituted alkyl, unsubstituted alkoxy, substituted alkoxy, —OH, —OCF$_3$, —CF$_3$, —CN, —NO$_2$, —C(O)R$^{11}$, —C(O)OR$^{11}$, —C(O)NR$^{11}$R$^{12}$, —SO$_{(t)}$NR$^{11}$R$^{12}$, —SO$_{(t)}$R$^{11}$, —C(O)NR$^{11}$OR$^{12}$, unsubstituted aryl, substituted aryl, unsubstituted heteroaryl, and substituted heteroaryl;

$R^2$ is selected from the group consisting of: —OH, —OC(O)NHR$^{16}$, —NHC(O)R$^{16}$ and —NHS(0)$_2$R$^{16}$;

$R^3$ is selected from the group consisting of: halogen, cyano, —CF$_3$, substituted alkyl, unsubstituted alkyl, substituted aryl, unsubstituted aryl, substituted heteroaryl and unsubstituted heteroaryl;

$R^4$ is selected from the group consisting of: substituted alkyl, unsubstituted alkyl, substituted aryl, unsubstituted aryl, substituted heteroaryl, unsubstituted heteroaryl, —COOR$^{17}$ and —OR$^{17}$;

$R^6$ is independently selected from the group consisting of: —OH, halogen, cyano, —CF$_3$, —OCF$_3$, —NR$^{11}$R$^{12}$, —NR$^{11}$(CO)NR$^{11}$R$^{12}$, —C(O)NR$^{11}$R$^{12}$, —CO$_2$R$^{11}$, —OR$^{11}$, —SO$_{(t)}$NR$^{11}$R$^{12}$, —NR$^{11}$SO$_{(t)}$R$^{12}$, —COR$^{11}$, substituted aryl, unsubstituted aryl, substituted alkyl, unsubstituted alkyl, substituted alkoxy, unsubstituted alkoxy, substituted aryalkyl, unsubstituted arylalkyl, substituted heteroalryl, unsubstituted heteroalryl, substituted aryloxy, unsubstituted aryloxy, substituted heteroalkyl, unsustituted heteroalalkyl, substituted heteroalalkoxy, unsubstituted heteroarylalkoxy, substituted heterocycloalkyl, unsubstituted heterocycloalkyl, substituted hydroxyalkyl, and unsubstituted hydroxyalkyl;

wherein the substituted $R^6$ groups are substituted with 1-6 substitutes, and each substituted on said substituted $R^6$ group is independently selected from the group consisting of: $R^{11}$, halogen, —CF$_3$, —OR$^{11}$, —OR$^{11}$, —NR$^{11}$R$^{12}$, —NO$_2$, —CN, —SO$_2$R$^{11}$, —SO$_2$NR$^{11}$R$^{12}$, —NR$^{11}$C(O)R$^{12}$, —C(O)NR$^{11}$R$^{12}$, —NR$^{11}$CO$_2$R$^{12}$, and —CO$_2$R$^{11}$;

$R^{11}$ and $R^{12}$ are independently selected from the group consisting of: hydrogen, unsubstituted alkyl, substituted alkyl, unsubstituted aryl, substituted aryl, unsubstituted alkylaryl, substituted alkylaryl, unsubstituted arylalkyl, substituted arylalkyl, unsubstituted cycloalkyl, substituted cycloalkyl, carboxyalkyl, aminoalkyl, unsubstituted heteroaryl, substituted heteroaryl, unsubstituted heteroarylalkyl, substituted heteroarylalkyl, unsubstituted heterocycloalkylalkyl, substituted heterocycloalkylalkyl, unsubstituted cycloalkylalkyl, substituted cycloalkylalkyl, unsubstituted heterocyclic, substituted heterocyclic, unsubstituted fluoroalkyl, and substituted fluoroalkyl; or $R^{11}$ and $R^{12}$, together with the nitrogen atom to which they are bound to in the groups —C(O)NR$^{11}$R$^{12}$ and —SO$_{(t)}$NR$^{11}$R$^{12}$, form an unsubstituted or substituted saturated heterocyclic ring, said ring optionally containing 1 to 3 additional heteroatoms wherein said optional heteroatoms are selected from the group consisting of O, S and —N(R$^{15}$), wherein there are optionally 1 to 3 substituents on the substituted cyclized $R^{11}$ and $R^{12}$ groups and each substituent is independently selected from the group consisting of alkyl, aryl, hydroxy, cyano, hydroxyalkyl, alkoxy, alkoxyalkyl, arylalkyl, fluoroalkyl, cycloalkyl, cycloalkylalkyl, heteroaryl, heteroarylalkyl, amino, aminoalkyl, —C(O)OR$^{13}$, —C(O)NR$^{13}$R$^{14}$, —S(O)$_t$NR$^{13}$R$^{14}$, —C(O)R$^{13}$, —SO$_2$R$^{13}$, —NHC(O)NR$^{13}$R$^{14}$, —NHC(O)OR$^{13}$, halogen, and —N(R$^{15}$)$_2$ wherein each $R^{15}$ is independently selected;

$R^{13}$ and $R^{14}$ independently selected from the group consisting of: H, unsubstituted alkyl, substituted alkyl, unsubstituted aryl, substituted aryl, unsubstituted arylalkyl, substituted arylalkyl, unsubstituted heteroaryl, substituted heteroaryl, unsubstituted cycloalkyl, substituted cycloalkyl, unsubstituted heteroarylalkyl, and substituted heteroarylalkyl;

$R^{15}$ is selected from the group consisting of: H, unsubstituted alkyl, substituted alkyl, unsubstituted fluoroalkyl, substituted fluoroalkyl, unsubstituted aryl, substituted aryl, unsubstituted heteroaryl, substituted heteroaryl, unsubstituted arylalkyl, substituted arylalkyl —C(O)$_2$R$^{13}$, —C(O)NR$^{13}$R$^{14}$, —S(O)$_t$NR$^{13}$R$^{14}$, —C(O)R$^{13}$ and —SO$_2$R$^{13}$;

$R^{16}$ is selected from the group consisting of: substituted alkyl, unsubstituted alkyl, substituted fluoroalkyl, unsubstituted fluoroalkyl, substituted aryl, unsubstituted aryl, substituted heteroaryl and unsubstituted heteroaryl;

$R^{17}$ is selected from the group consisting of: alkyl, substituted alkyl, unsubstituted alkyl, substituted aryl, unsubstituted aryl, substituted heteroaryl, unsubstituted heteroaryl, unsubstituted fluoroalkyl, substituted fluoroalkyl, unsubstituted arylalkyl, substituted arylalkyl, unsubstituted heteroarylalkyl, substituted heteroarylalkyl, substituted cycloalkyl and unsubstituted cycloalkyl;

wherein when said substituted $R^1$, $R^3$, $R^4$, $R^{11}$, $R^{12}$, $R^{13}$, $R^{14}$, $R^{15}$, $R^{16}$, and $R^{17}$ groups are other than substituted alkyl, then the substituents for said substituted $R^1$, $R^3$, $R^4$, $R^{11}$, $R^{12}$, $R^{13}$, $R^{14}$, $R^{15}$, $R^{16}$, and $R^{17}$ groups are independently selected from the group consisting of: alkyl, —$CF_3$, —OH, alkoxy, hydroxyalkyl, aryl, arylalkyl, aminoalkyl, fluoroalkyl, fluoroalkoxy, cycloalkyl, cycloalkylaryl, heteroaryl, heteroarylalkyl, halogen, —$C(O)_2R^{13a}$, —$C(O)NR^{13a}R^{14a}$, —$S(O)_tNR^{13a}R^{14a}$, —$C(O)R^{13a}$, —$SO_2R^{13a}$, and —$N(R^{15a})_2$, wherein each $R^{13a}$, $R^{14a}$, and $R^{15a}$ is independently selected from the group consisting of unsubstituted alkyl, unsubstituted aryl, halo substituted aryl, unsubstituted arylalkyl, halo substituted arylalkyl, and unsubstituted cycloalkyl, except that the cyclized $R^{11}$ and $R^{12}$ are optionally substituted as provided above;

wherein when said substituted $R^1$, $R^3$, $R^4$, $R^{11}$, $R^{12}$, $R^{13}$, $R^{14}$, $R^{15}$, $R^{16}$, and $R^{17}$ groups are substituted alkyl, then the substituents for said substituted $R^1$, $R^3$, $R^4$, $R^{11}$, $R^{12}$, $R^{13}$, $R^{14}$, $R^{15}$, $R^{16}$, and $R^{17}$ groups are independently selected from the group consisting of: —$CF_3$, —OH, alkoxy, hydroxyalkyl, aryl, arylalkyl, aminoalkyl, fluoroalkyl, fluoroalkoxy, cycloalkyl, cycloalkylaryl, heteroaryl, heteroarylalkyl, halogen, —$C(O)_2R^{13a}$, —$C(O)NR^{13a}R^{14a}$, —$S(O)_tNR^{13a}R^{14a}$, —$C(O)R^{13a}$, —$SO_2R^{13a}$, and —$N(R^{15a})_2$, wherein each $R^{13a}$, $R^{14a}$, and $R^{15a}$ is independently selected from the group consisting of unsubstituted alkyl, unsubstituted aryl, halo substituted aryl, unsubstituted arylalkyl, halo substituted arylalkyl, and unsubstituted cycloalkyl, except that the cyclized $R^{11}$ and $R^{12}$ are optionally substituted as provided above;

k=0 to 5;
q=0 to 3; and
t is 1 or 2.

2. The compound according to claim 1 wherein 5-het is:

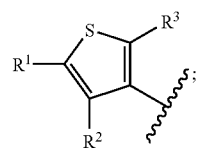

Q is selected from the group consisting of:

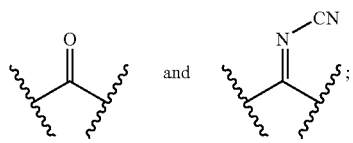

Y is:

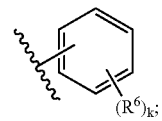

$R^1$ is selected from the group consisting of —$SO_{(t)}NR^{11}R^{12}$ and —$SO_{(t)}R^{11}$;

$R^2$ is selected from the group consisting of: —OH and —$OC(O)NHR^{16}$;

$R^3$ is selected from the group consisting of: H, alkyl halogen and —$CF_3$;

$R^6$ is selected from the group consisting of: halogen and alkyl and k is 2 and each $R^6$ is independently selected.

3. The compound according to claim 2 wherein:

$R^1$ is —$SO_2NR^{11}R^{12}$;

$R^3$ is selected from the group consisting of: H, Cl and —$CF_3$;

$R^{11}$ is selected from the group consisting of: H, unsubstituted alkyl, substituted alkyl, unsubstituted cycloalkyl, and substituted cycloalkyl;

$R^{12}$ is selected from the group consisting of: H, unsubstituted alkyl, substituted alkyl, unsubstituted cycloalkyl, and substituted cycloalkyl;

$R^2$ is selected from the group consisting of: —OH and —$OC(O)NHR^{16}$;

$R^{16}$ is selected from the group consisting of: alkyl, aryl and heteroaryl; and Y is

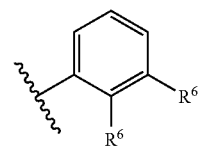

wherein each $R^6$ is independently selected.

4. The compound of claim 1 in an isolated and pure form.

5. The compound of claim 1 selected from the group consisting of:

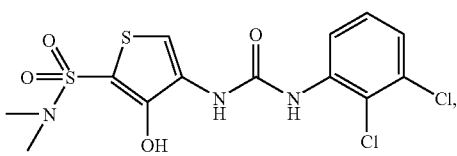

-continued
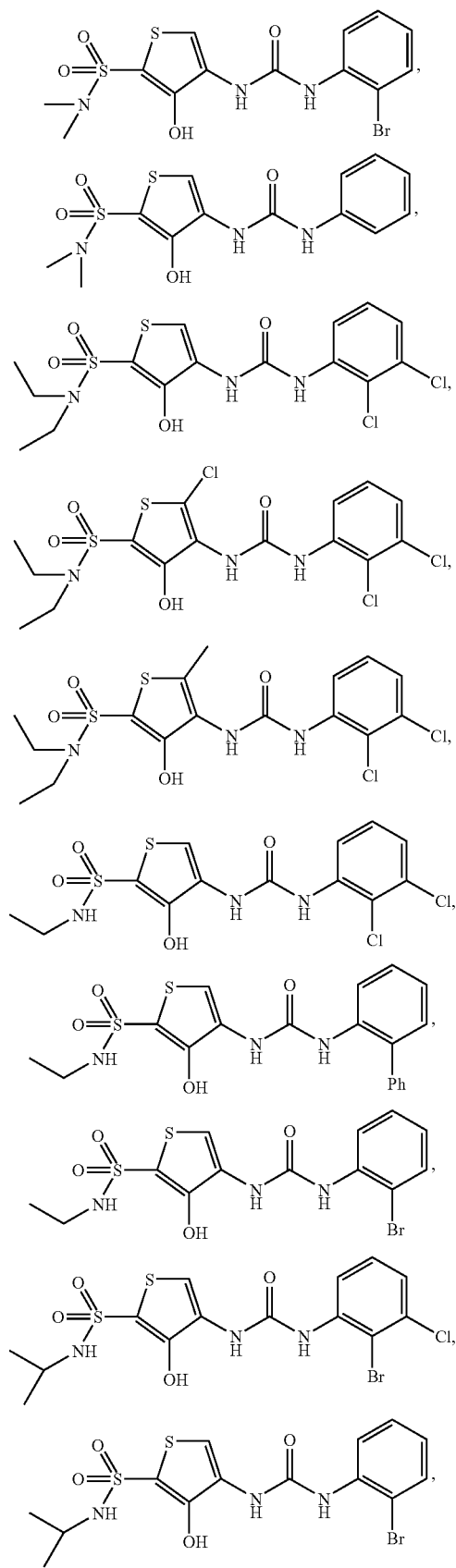
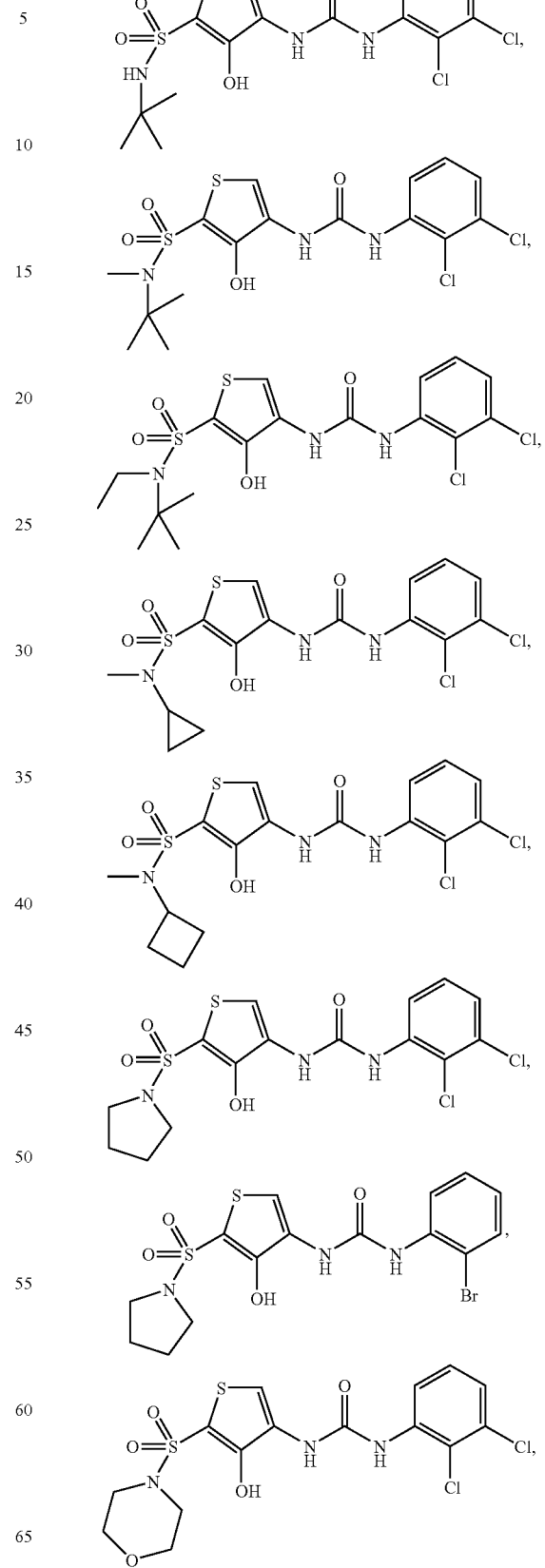

-continued
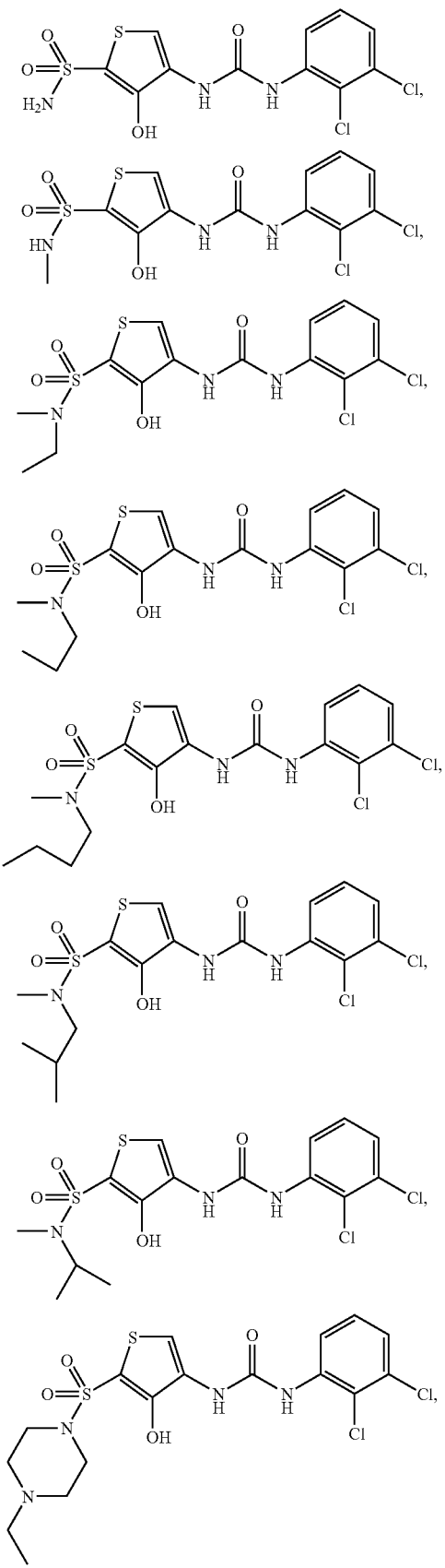
-continued
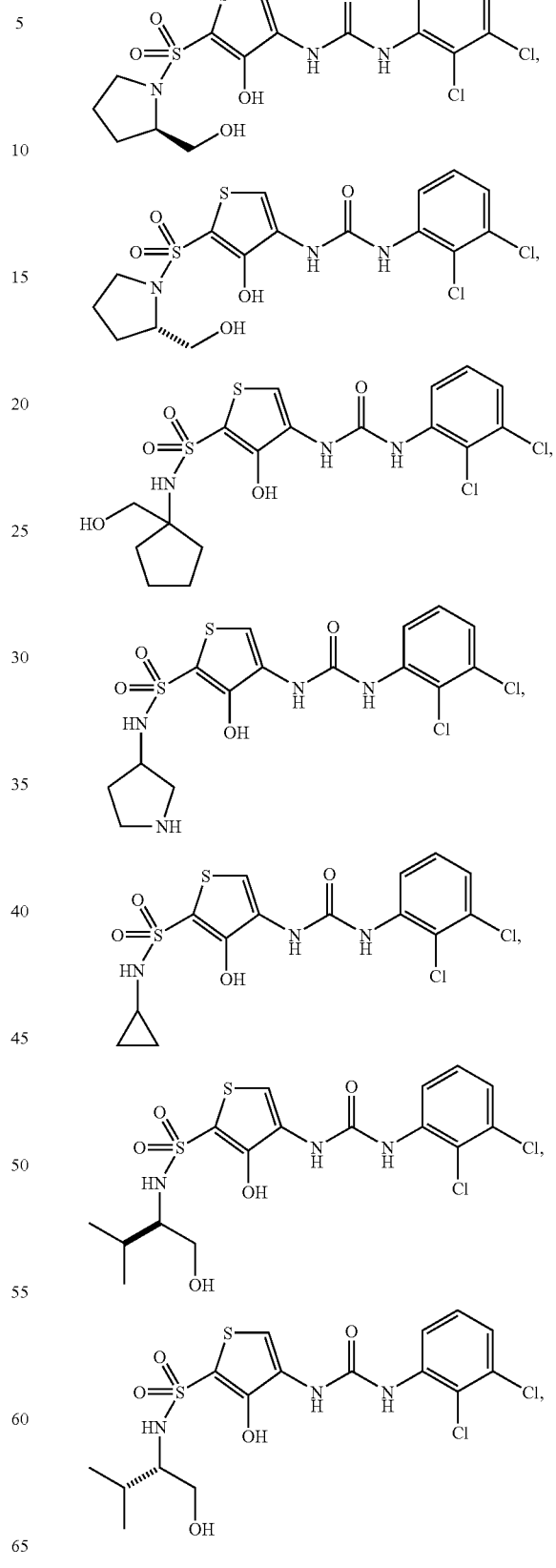

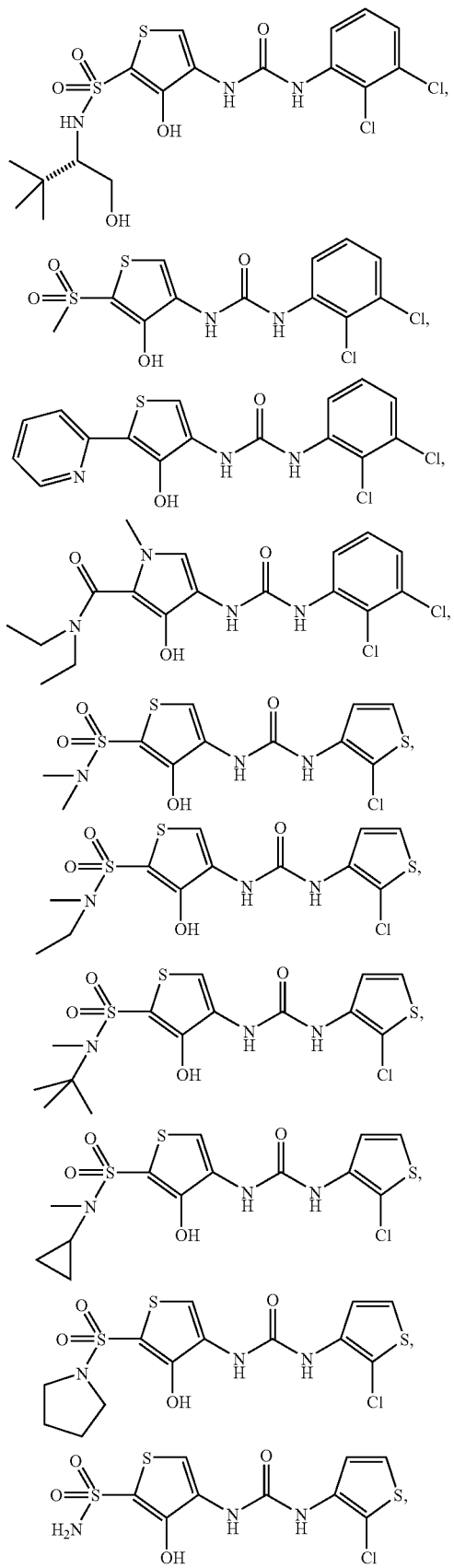
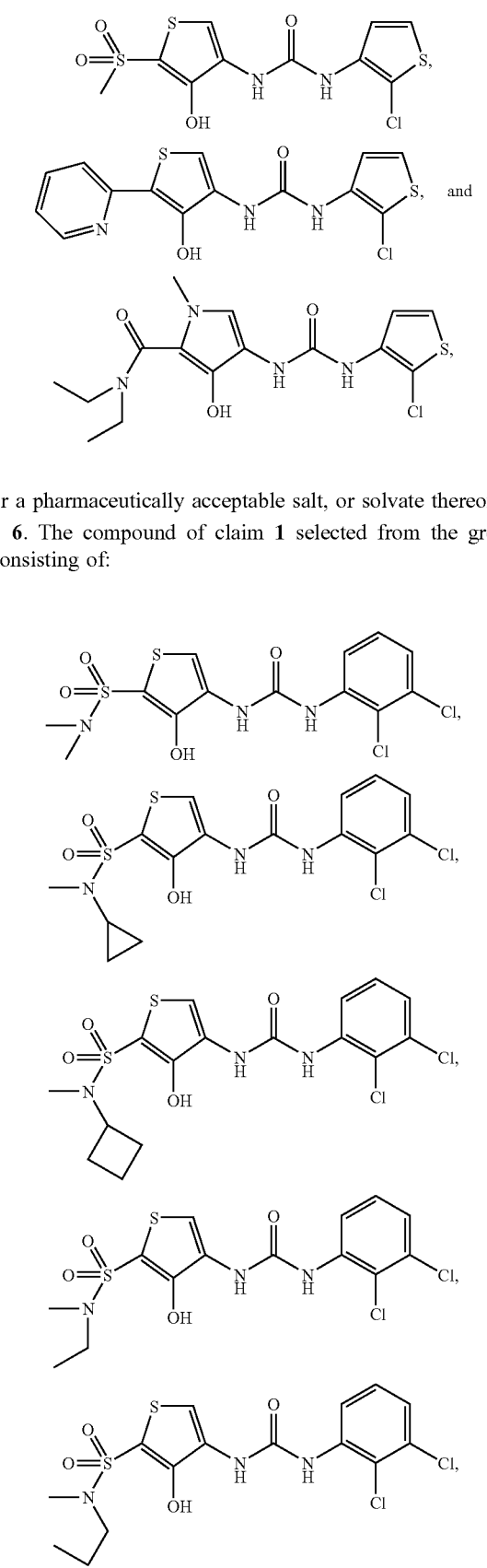
or a pharmaceutically acceptable salt, or solvate thereof.
6. The compound of claim 1 selected from the group consisting of:

-continued
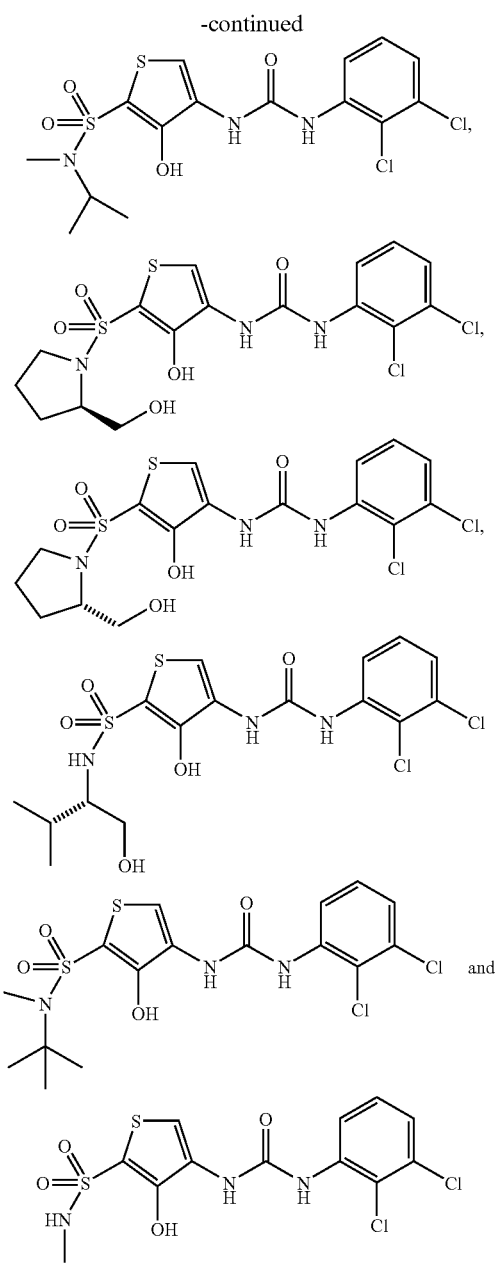
or a pharmaceutically acceptable salt, or solvate thereof.
7. The compound of claim 1 selected from the group consisting of:
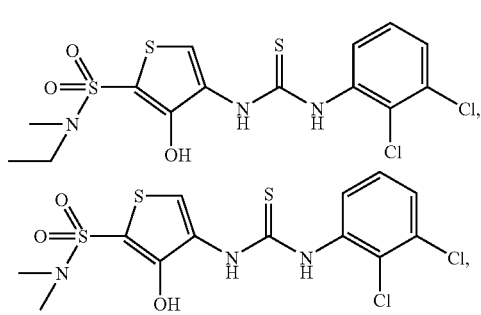
-continued
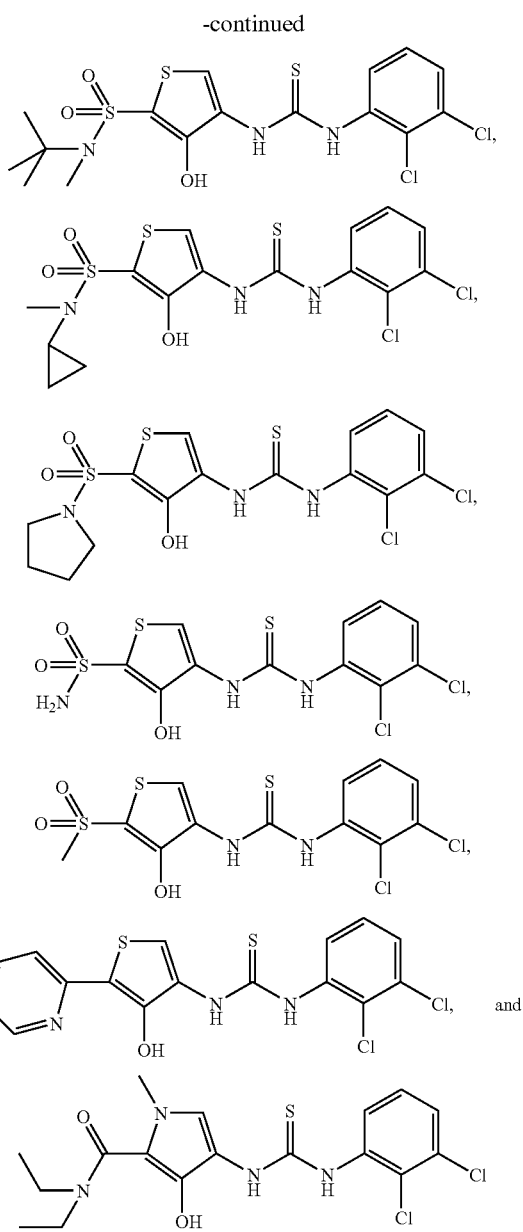
or a pharmaceutically acceptable salt, or solvate thereof.
8. The compound of claim 1 selected from the group consisting of:
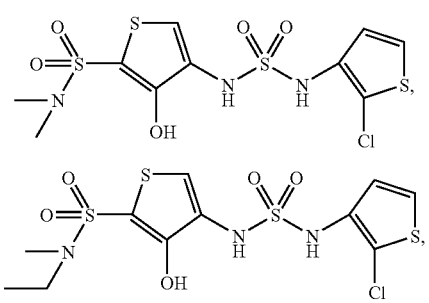

-continued
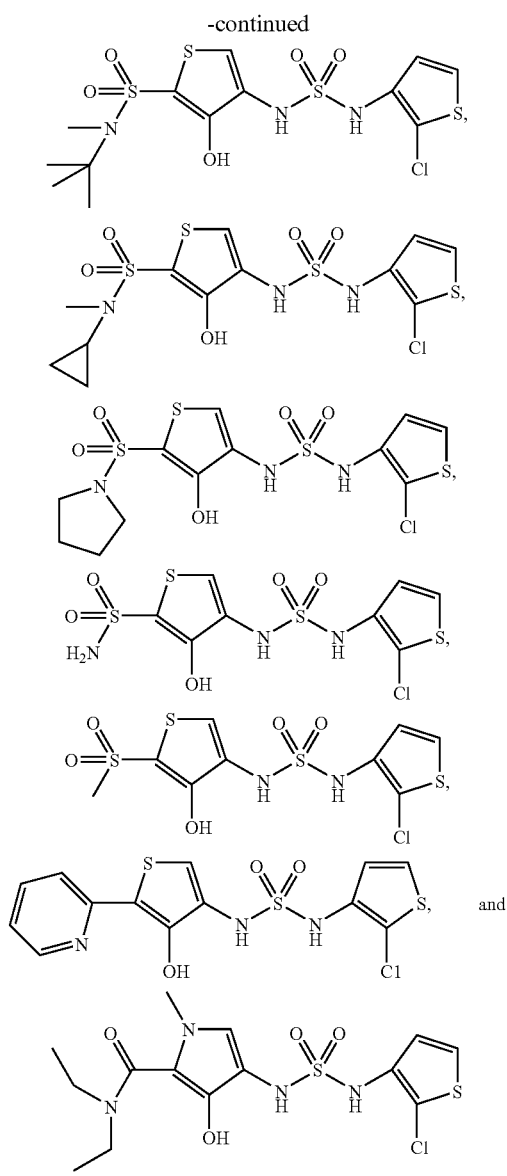
or a pharmaceutically acceptable salt, or solvate thereof.
9. The compound of claim 1 selected from the group consisting of:
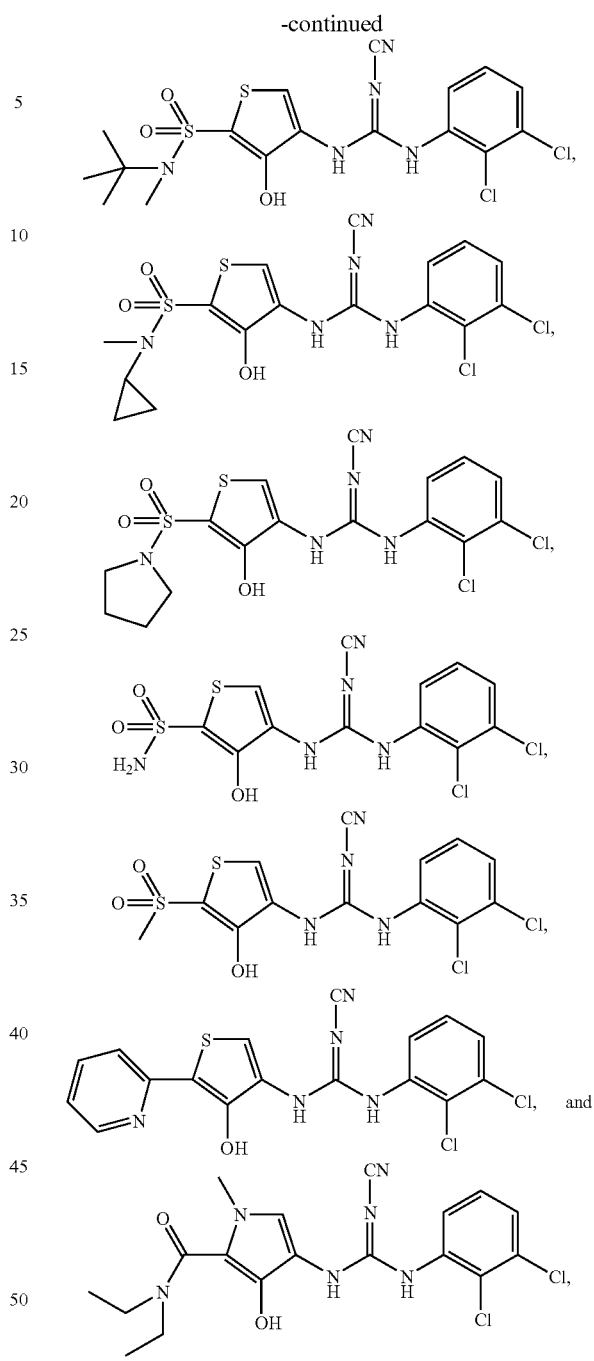
or a pharmaceutically acceptable salt, or solvate thereof.
10. The compound of claim 1 having the formula:
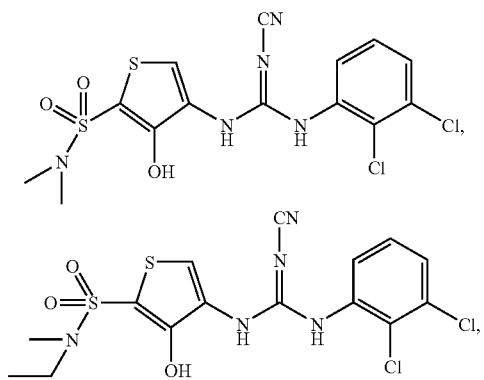
or a pharmaceutically acceptable salt, or solvate thereof.

11. A compound of the formula:
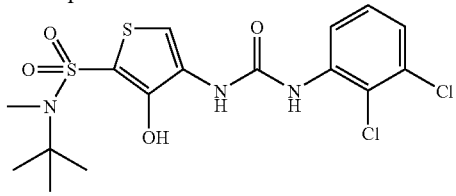
or a pharmaceutically acceptable salt, or solvate thereof.
12. A pharmaceutical composition comprising at least one compound of claim 1, or a pharmaceutically acceptable salt or solvate thereof, in combination with a pharmaceutically acceptable carrier.
13. The compound of claim 1 wherein $R^2$ is —OH.
* * * * *